US011453715B2

(12) United States Patent
Torres et al.

(10) Patent No.: US 11,453,715 B2
(45) Date of Patent: Sep. 27, 2022

(54) **CELLULAR FACTORS INVOLVED IN THE CYTOTOXICITY OF *STAPHYLOCOCCUS AUREUS* LEUKOCIDINS: NOVEL THERAPEUTIC TARGETS**

(71) Applicant: NEW YORK UNIVERSITY, New York, NY (US)

(72) Inventors: Victor J. Torres, New York, NY (US); Tamara Reyes-Robles, New York, NY (US); Francis Alonzo, III, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 16/894,500

(22) Filed: Jun. 5, 2020

(65) Prior Publication Data
US 2021/0009664 A1 Jan. 14, 2021

Related U.S. Application Data

(60) Continuation of application No. 16/393,249, filed on Apr. 24, 2019, now abandoned, which is a division of application No. 14/899,977, filed as application No. PCT/US2014/043021 on Jun. 18, 2014, now Pat. No. 10,301,378.

(60) Provisional application No. 61/836,516, filed on Jun. 18, 2013.

(51) Int. Cl.
| | |
|---|---|
| C07K 16/12 | (2006.01) |
| A61K 38/16 | (2006.01) |
| A61K 38/19 | (2006.01) |
| A61K 39/085 | (2006.01) |
| A61K 39/40 | (2006.01) |
| A61K 31/255 | (2006.01) |
| A61K 31/341 | (2006.01) |
| A61K 31/44 | (2006.01) |
| A61K 31/505 | (2006.01) |
| C07K 16/28 | (2006.01) |
| A61K 45/06 | (2006.01) |

(52) U.S. Cl.
CPC ........ *C07K 16/1271* (2013.01); *A61K 31/255* (2013.01); *A61K 31/341* (2013.01); *A61K 31/44* (2013.01); *A61K 31/505* (2013.01); *A61K 38/164* (2013.01); *A61K 38/195* (2013.01); *A61K 39/085* (2013.01); *A61K 39/40* (2013.01); *A61K 45/06* (2013.01); *C07K 16/2896* (2013.01); *C07K 2317/76* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 8,846,609 B2 | 9/2014 | Torres et al. | |
| 9,091,689 B2 | 7/2015 | Torres et al. | |
| 10,301,378 B2* | 5/2019 | Torres | A61K 38/164 |
| 2009/0270318 A1 | 10/2009 | Gordon et al. | |
| 2009/0306225 A1 | 12/2009 | Lighter et al. | |
| 2012/0093850 A1 | 4/2012 | Bagnoli et al. | |
| 2013/0017203 A1 | 1/2013 | Torres et al. | |
| 2013/0143757 A1* | 6/2013 | Zhong | G01N 33/6893 506/9 |
| 2015/0056163 A1 | 2/2015 | Torres et al. | |
| 2015/0274814 A1 | 10/2015 | Torres et al. | |

FOREIGN PATENT DOCUMENTS

| | | |
|---|---|---|
| WO | 2007/145689 A1 | 12/2007 |
| WO | 2010/119343 A1 | 10/2010 |
| WO | 2013/082558 A1 | 6/2013 |

OTHER PUBLICATIONS

Uniprot Accession #Q2FXB1 Oct. 31, 2012.*
PIR_80 database accession # S75021 Apr. 25, 1997.*
PIR_80 database accession # S32419 Mar. 19, 1997.*
Uniprot Accession #D3K2W1 Mar. 23, 2010.*
Uniprot Accession # Q8NVL8 Aug. 21, 2007.*
International Search Report and Written Opinion for PCT/US2014/043021 (dated Feb. 6, 2015).
Tikhonov et al., "Down-Regulation of CXCR1 and CXCR2 Expression on Human Neutrophils Upon Activation of Whole Blood by *S. aureus* is Mediated by TNF-alpha," Clin. Exp Immunol. 125:414-422 (2001).
Reyes-Robles et al., "*Staphylococcus aureus* Leukotoxin ED Targets the Chemokine Receptors CXCR1 and CXCR2 to Kill Leukocytes and Promote Infection," Cell Host Microbe. 14(4):1-15 (2013).
Supplementary European Search Report for Corresponding European Application No. 14813300.2 (dated Dec. 2, 2016).
Alonzo et al., "CCR5 is a Receptor for *Staphylococcus aureus* Leukotoxin ED" Nature 493:51-54 + 2 Supplemental Pages (Jan. 2013).
Alonzo et al., "Bacterial Survival Amidst an Immune Onslaught: The Contribution of the *Staphylococcus aureus* Leukotoxins" PLOS Pathogens 9(2)e 1003143 (Feb. 2013).
Konrad et al., "CXCR2 in Acute Lung Injury" Mediators of Inflammation 2012:740987 (2012).
Lin et al., "New Insights Into the Prevention of Staphylococcal Infections and Toxic Shock Syndrome," Expert Rev Clin Pharmacol. 3(6):753-767 (2010).

(Continued)

*Primary Examiner* — Oluwatosin A Ogunbiyi
(74) *Attorney, Agent, or Firm* — Troutman Pepper Hamilton Sanders LLP (Rochester)

(57) ABSTRACT

The present invention relates to methods for treating and preventing *Staphylococcus aureus* infection and/or a condition resulting from a *S. aureus* infection in a subject that involves administering compositions that inhibit *S. aureus* interaction with CXCR1/CXCR2 and DARC cellular receptors. The present invention further relates to novel compositions for carrying out these and other methods.

7 Claims, 17 Drawing Sheets

Specification includes a Sequence Listing.

(56) References Cited

OTHER PUBLICATIONS

Watkins et al., "Current Concepts on the Virulence Mechanisms of Methicillin-Resistant *Staphylococcus aureus*," J Med Microbiol. 61 (Pt 9):1179-93 (2012).
English Translation and Notice of Reasons for Rejection for Japanese Patent Application No. 2016-521554 (dated Mar. 8, 2018).
Luo et al., "Deletion of the Murine Duffy Gene (Dfy) Reveals that the Duffy Receptor is Functionally Redundant," Molecular and Cellular Biology 20(9):3097-3101 (2000).
Guillet et al., "Crystal Structure of Leucotoxin S Component: New Insight Into the Staphylococcal Beta-Barrel Pore-Forming Toxins," Journal of Biological Chemistry 279(39):41028-41037 (2004).
Extended European Search Report for European Application No. 18193473.8 (dated Dec. 14, 2018).
English translation and Examination Report for Chinese Application No. 201480045452.7 (dated Oct. 15, 2018).
Office Action for U.S. Appl. No. 14/899,977 (dated Jun. 12, 2017).
Office Action for U.S. Appl. No. 14/899,977 (dated Nov. 20, 2017).
Office Action for U.S. Appl. No. 14/899,977 (dated Mar. 20, 2018).
Office Action for U.S. Appl. No. 14/899,977 (dated Sep. 28, 2018).
Office Action for Japanese Patent Application No. 2016-521554 (dated Feb. 4, 2019).
Extended European Search Report for European Application No. 20187045.8 (dated Jun. 10, 2021).

\* cited by examiner

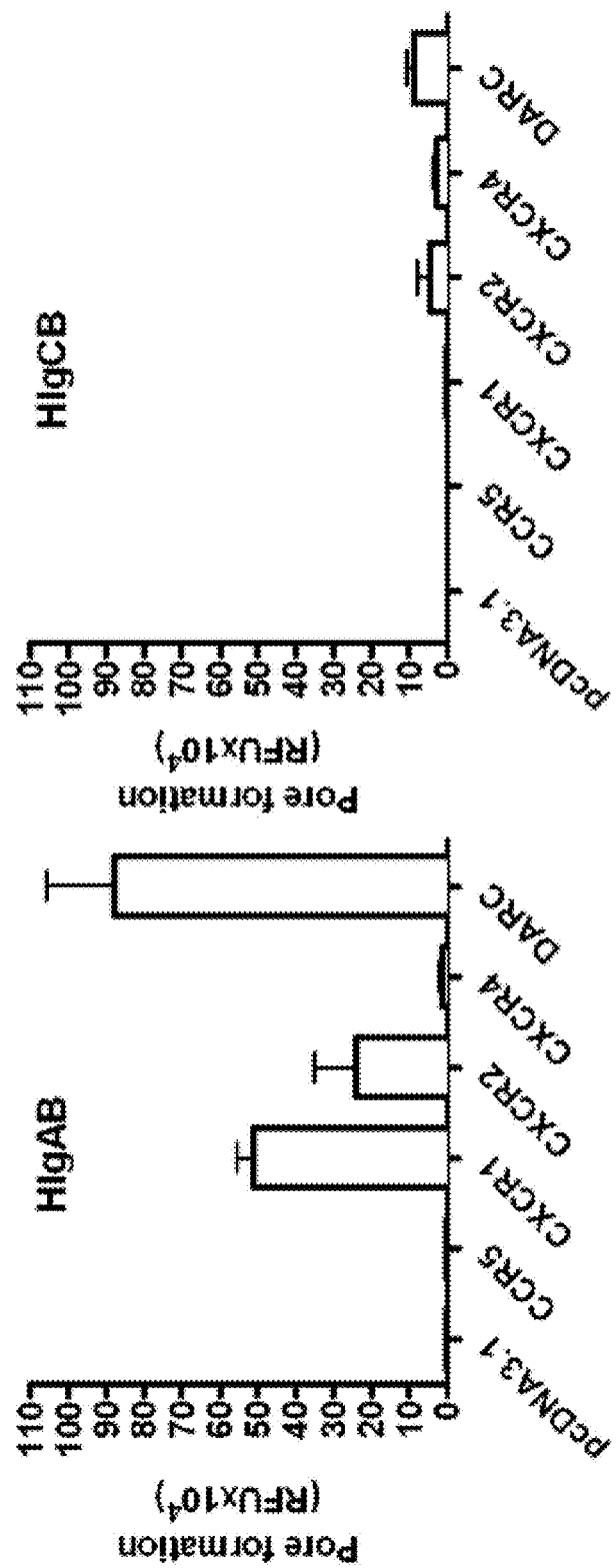

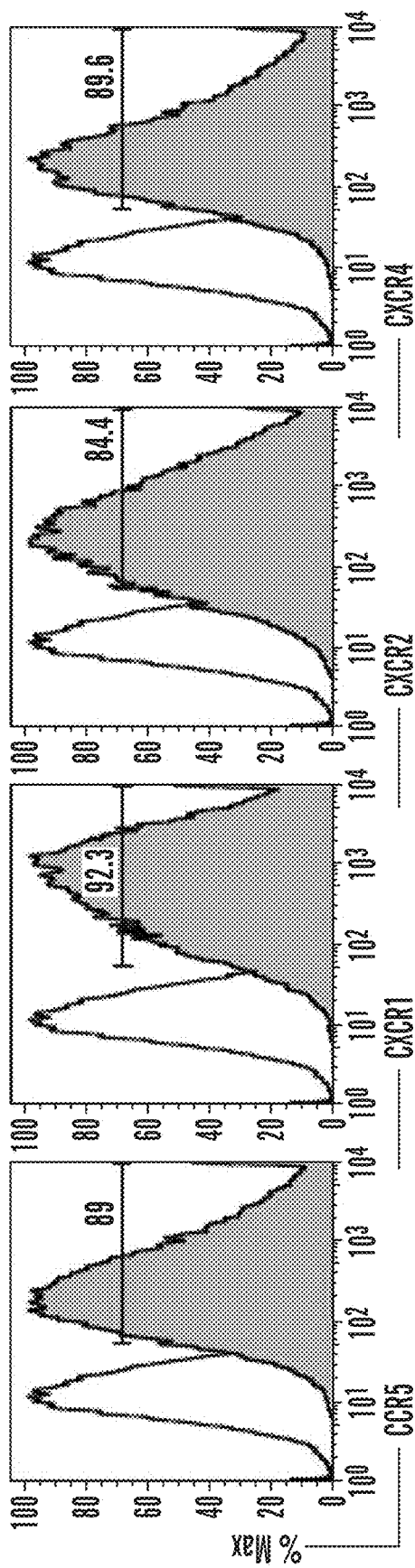
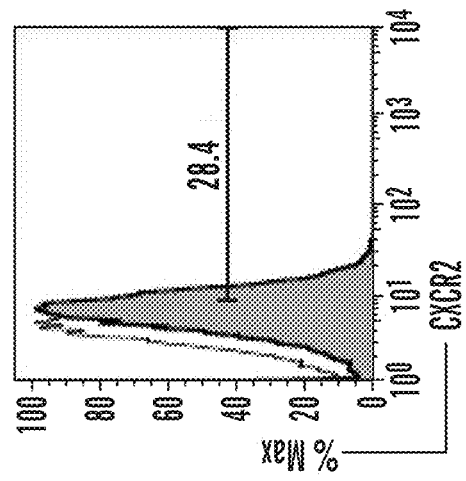
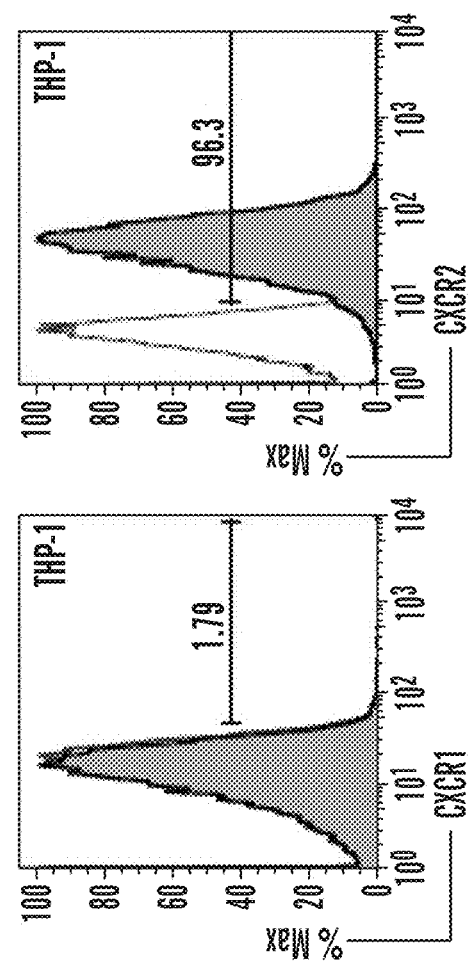
Figure 5A
Figure 5B
Figure 5C

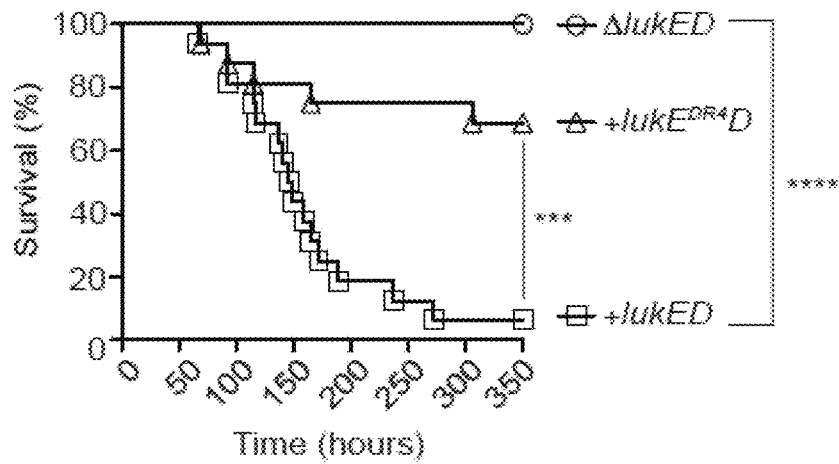
Figure 12C
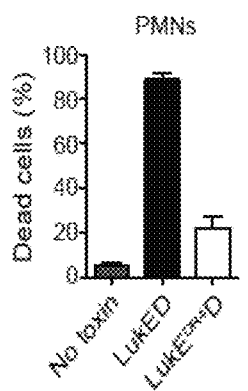 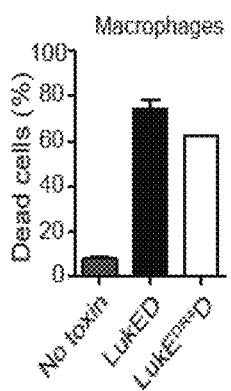
Figure 13A
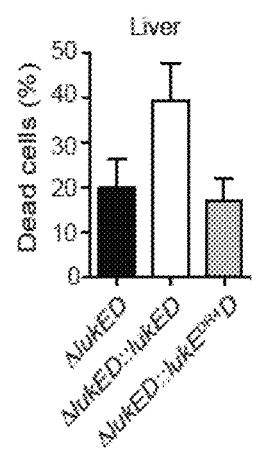 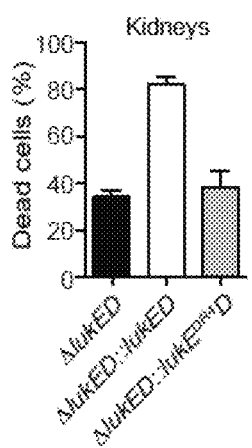
Figure 13B

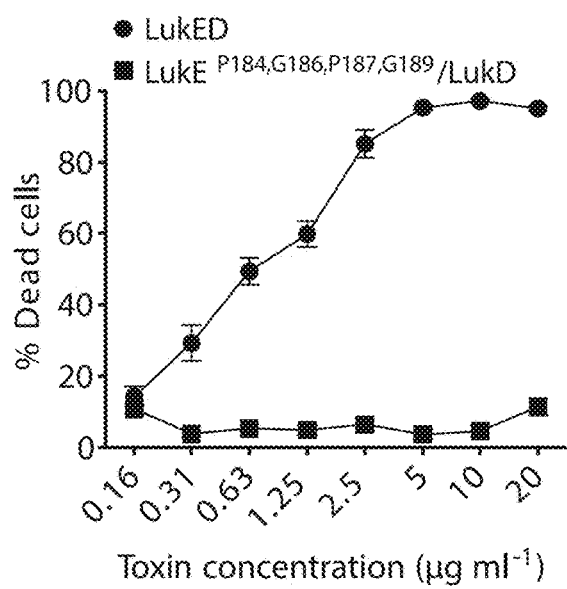
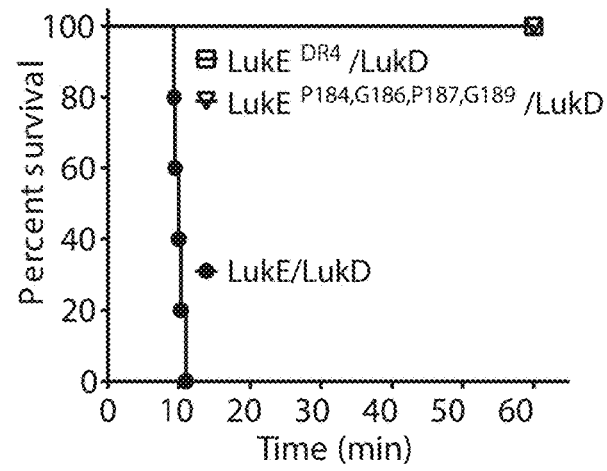
Figure 15A
Figure 15B

CELLULAR FACTORS INVOLVED IN THE CYTOTOXICITY OF *STAPHYLOCOCCUS AUREUS* LEUKOCIDINS: NOVEL THERAPEUTIC TARGETS

This application claims the benefit of U.S. Provisional Patent Application Ser. No. 61/836,516, filed Jun. 18, 2013, which is hereby incorporated by reference in its entirety.

FIELD OF THE INVENTION

This invention relates to methods of treating and preventing *Staphylococcus aureus* infections, and to methods of identifying novel therapeutics for the treatment and prevention of *Staphylococcus aureus* infections.

BACKGROUND OF THE INVENTION

*Staphylococcus aureus* (*S. aureus*) is a bacterium that commensally colonizes more than 25% of the human population. Upon gaining access to the bloodstream, *S. aureus* disseminates resulting in a wide range of diseases. *S. aureus* is the leading cause of nosocomial infections, is the most common etiological agent of infectious endocarditis as well as skin and soft tissue infections, and is one of the four leading causes of food-borne illness. Altogether, *S. aureus* is estimated to infect more than 1.2 million patients per year in USA hospitals. The threat of *S. aureus* to human health is further highlighted by the emergence of antibiotic-resistant strains (i.e., MRSA strains), including strains that are resistant to vancomycin, an antibiotic considered the last line of defense against *S. aureus* infection. These facts highlight the importance of developing novel therapeutics against this important pathogen.

The success of *S. aureus* as a human pathogen is in part due to the ability of this bacterium to disarm the host's immune system by producing an arsenal of virulence factors that are secreted into the extracellular milieu (Foster, T. J. "Immune Evasion by Staphylococci," *Nat. Rev. Microbiol.* 3:948-58 (2005)). Among these, the bicomponent, pore-forming leukotoxins are of particular interest because they target and kill a variety of immune cells involved in infection-control (Vandenesch et al., "*Staphylococcus aureus* Hemolysins, Bi-Component Leukocidins, and Cytolytic Peptides: A Redundant Arsenal of Membrane-Damaging Virulence Factors?" *Front. Cell. Infect. Microbiol.* 2:12 (2012); Alonzo & Torres, "Bacterial Survival Amidst an Immune Onslaught: The Contribution of the *Staphylococcus aureus* Leukotoxins. *PLoS Pathog.* 9:e1003143 (2013)). Among these immune cells, leukotoxins kill polymorphonuclear cells also known as "PMNs", which act as the initial barrier to infection by means of phagocytic killing of the intruding microorganism (Rigby & DeLeo, "Neutrophils in Innate Host Defense Against *Staphylococcus aureus* Infections," *Semin. Immunopathol.* 34:237-59 (2012)).

Each leukotoxin is composed of two subunits, the "S" and "F" type, which act in concert to form octameric pores in target cell membranes (Yamashita et al., "Crystal Structure of the Octameric Pore of Staphylococcal Gamma-Hemolysin Reveals the Beta-Barrel Pore Formation Mechanism by Two Components," *Proc. Nat'l. Acad. Sci. U.S.A.* 108: 17314-9 (2011)), ultimately leading to cell death. Clinically relevant strains of *S. aureus* can produce up to five different bicomponent leukotoxins: Panton-Valentine leukocidin (PVL or LukFS-PV), leukocidin E/D (LukED), γ-hemolysin (HlgAB and HlgCB), and leukocidin A/B (LukAB; also known as LukGH) (Vandenesch et al., "*Staphylococcus aureus* Hemolysins, Bi-Component Leukocidins, and Cytolytic Peptides: A Redundant Arsenal of Membrane-Damaging Virulence Factors?" *Front. Cell. Infect. Microbiol.* 2:12 (2012); Alonzo & Torres, "Bacterial Survival Amidst an Immune Onslaught: The Contribution of the *Staphylococcus aureus* Leukotoxins. *PLoS Pathog.* 9:e1003143 (2013)). These toxins are each capable of targeting and killing human PMN, but they also exhibit tropism towards additional leukocytes (Alonzo & Torres, "Bacterial Survival Amidst an Immune Onslaught: The Contribution of the *Staphylococcus aureus* Leukotoxins. *PLoS Pathog.* 9:e1003143 (2013); Gravet et al., "Characterization of a Novel Structural Member, LukE-LukD, of the Bi-Component Staphylococcal Leucotoxins Family," *FEBS Lett.* 436: 202-8 (1998); Morinaga et al., "Purification, Cloning and Characterization of Variant LukE-LukD With Strong Leukocidal Activity of Staphylococcal Bi-Component Leukotoxin Family," *Microbiol. Immunol.* 47:81-90 (2003); Perret et al., "Cross-Talk Between *Staphylococcus aureus* Leukocidins-Intoxicated Macrophages and Lung Epithelial Cells Triggers Chemokine Secretion in an Inflammasome-Dependent Manner," *Cell. Microbiol.* 14:1019-36 (2012)), suggesting that *S. aureus* uses leukotoxins to deplete the immune cells responsible for protecting the body from infection. In addition to leukocytes, HlgAB, HlgCB and LukED can also lyse red blood cells (RBC) (Morinaga et al., "Purification, Cloning and Characterization of Variant LukE-LukD With Strong Leukocidal Activity of Staphylococcal Bi-Component Leukotoxin Family," *Microbiol. Immunol.* 47:81-90 (2003)), which could contribute to *S. aureus* growth in vivo by releasing hemoglobin from RBC for use as an iron source (Torres et al., "*Staphylococcus aureus* Fur Regulates the Expression of Virulence Factors That Contribute to the Pathogenesis of Pneumonia," *Infect. Immun.* 78:1618-28 (2010)).

Despite more than one hundred years of investigation into the cytotoxic activity of *S. aureus* leukotoxins, the cellular receptors that dictate the tropism of leukotoxins to immune cells and RBC remain incompletely defined.

The present invention is directed to overcoming these and other limitations in the art.

SUMMARY OF THE INVENTION

A first aspect of the present invention is directed to a method of preventing or treating *Staphylococcus aureus* infection and/or a condition resulting from a *S. aureus* infection in a subject. This method involves selecting a subject having or at risk of having *S. aureus* infection and administering, to the selected subject, a composition that inhibits *S. aureus* interaction with CXCR1 and CXCR2, under conditions effective to prevent or treat *S. aureus* infection and/or a condition resulting from a *S. aureus* infection in the subject.

Another aspect of the present invention is directed to a method of preventing or treating *Staphylococcus aureus* infection and/or a condition resulting from a *S. aureus* infection in a subject. This method involves selecting a subject having or at risk of having *S. aureus* infection and administering, to the selected subject, a composition that inhibits *S. aureus* interaction with Duffy antigen receptor for chemokines (DARC), under conditions effective to prevent or treat *S. aureus* infection and/or a condition resulting from a *S. aureus* infection in the subject.

Another aspect of the present invention is directed to a method of treating a subject having a *S. aureus* infection. This method involves obtaining a sample from the subject having *S. aureus* infection and quantifying expression levels of CXCR1, CXCR2, DARC, or a combination thereof in the sample. The method further involves administering a treatment for the subject based on the quantified expression levels.

Another aspect of the present invention is directed to an isolated Leukocidin E (LukE) antibody, or antibody binding fragment thereof, wherein said antibody or binding fragment thereof, binds an epitope corresponding to amino acid residues 182-196 of SEQ ID NO:4.

Another aspect of the present invention is directed to an isolated HlgA antibody, or antibody binding fragment thereof, wherein said antibody or binding fragment thereof, binds an epitope corresponding to amino acid residues 180-192 of SEQ ID NO:6.

Another aspect of the present invention is directed to a composition comprising an isolated Leukocidin E (LukE) protein or polypeptide thereof having a non-functional CXCR1/CXCR2 binding domain and a pharmaceutically acceptable carrier.

Another aspect of the present invention is directed to a composition comprising an isolated HlgA protein or polypeptide thereof having a non-functional CXCR1/CXCR2 binding domain and a pharmaceutically acceptable carrier.

*S. aureus* infects more than 1.2 million patients per year in USA hospitals, with around 40,000 deaths per year in the USA. This bacterium is the leading cause of nosocomial and community acquired infections; is the most common etiological agent of infectious endocarditis, skin, and soft tissue infections; and is one of the four leading causes of foodborne illness. The threat of *S. aureus* to human health is further compounded by the emergence of antibiotic-resistant strains, including methicillin-resistant *S. aureus* (MRSA). These facts highlight the importance of identifying new targets for the development of novel therapeutics. The present invention relates to the discovery that CXCR1, CXCR2, and DARC are human cellular receptors for the *S. aureus* virulence factors leukocidin ED (LukED) and γ-hemolysin AB (HlgAB). This information has tremendous therapeutic implications for the treatment of *S. aureus* infections. CXCR1/CXCR2 are mainly found on the surface of PMNs, which are the first responders involved in the control of *S. aureus* infections. The importance of PMNs in avoidance of *S. aureus* infections is best evidenced by the observation that humans harboring genetic defects in PMN functions are highly susceptible to *S. aureus* infections (Rigby & DeLeo, "Neutrophils in Innate Host Defense Against *Staphylococcus aureus* Infections," *Semin. Immunopathol.* 34:237-59 (2012), which is hereby incorporated by reference in its entirety). The methods and compositions for blocking LukED and HlgAB interaction with CXCR1/CXCR2 of the present invention will prevent LukED and HlgAB-mediated killing of these cells, which in turn will increase the ability of the host's immune system to combat *S. aureus* infection. In addition, CXCR1, CXCR2, and DARC are also found on the surface of the endothelium, and LukED- and HlgAB-mediated injury of endothelial cells is likely to facilitate endovascular permeability resulting in septic shock, a common outcome of *S. aureus* bloodstream infection that results in sepsis. Therefore, blockade of LukED and HlgAB-mediated effects on endothelial cells using the methods and compositions of the present invention will likewise facilitate the treatment and prevention of *S. aureus* infection.

BRIEF DESCRIPTION OF THE DRAWINGS

In FIG. 1A, peripheral blood mononuclear cells (PBMCs) isolated from a Δ32Ccr5 donor were incubated with PBS or LukED (75 nM) and gated for CD14 and CD3 positivity. FIG. 1B shows the viability of primary human neutrophils (PMNs) isolated from a Ccr5$^+$ or a Δ32Ccr5 donor in the presence of LukE, LukD or LukED (75 nM). FIG. 1C shows the bacterial burden (CFUs) from livers of Ccr5$^{+/+}$ mice systemically infected with isogenic *S. aureus* WT (N=14), ΔlukED (N=15) or ΔlukED::lukED (N=15) strains, and Ccr5-mice systemically infected with *S. aureus* WT (N=10) or ΔlukED (N=11). FIG. 1D is a graph showing viability of HEK293T cells transfected with the indicated chemokine receptors and incubated with LukED or LukSF-PV (600 nM). FIGS. 1E-1F show CXCR1 and CXCR2 levels on the surface of PMNs (FIG. 1E) or monocytes (FIG. 1F) as determined by flow cytometry. FIG. 1G shows the viability of THP-1 cells transduced with non-target or Cxcr2 shRNA treated with LukED. *P<0.05 by one-way analysis of variance (FIG. 1C). Means±s.e.m. are shown (n=3).

FIGS. 4A-4B show that HlgAB uses CXCR1, CXCR2, and DARC to target and kill mammalian cells. HEK293T cells were transfected with plasmids containing the cDNA encoding the indicated chemokine receptors. Cells were then exposed to 20 g/ml of HlgAB (FIG. 4A) or HlgCB (FIG. 4B) as indicated and toxin-mediated pores measured by ethidium bromide permeability.

FIGS. 5A-5C show surface levels of several tested chemokine receptors on transiently transfected HEK293T and THP-1 cells. FIG. 5A shows the surface levels of CCR5, CXCR1, CXCR2, and CXCR4 on transiently transfected HEK293T cells as evaluated by flow cytometry. FIG. 5B shows CXCR1 and CXCR2 surface levels on THP-1 cells as evaluated by flow cytometry. FIG. 5C shows CXCR2 levels on Cxcr2 shRNA-transduced THP-1 cells as determined by flow cytometry.

FIG. 6A shows binding of GFP-LukE or GFP-LukD to the surface of PMNs evaluated by flow cytometry. FIG. 6B shows binding of GFP-LukE (300 nM) to PMNs in the presence of unlabeled LukE or LukS-PV as determined by flow cytometry. FIG. 6C shows viability of PMNs challenged with a lethal dose of LukED (75 nM) in the presence of CXCL8 or CXCL1. FIG. 6D shows binding of GFP-LukE (300 nM) to the surface of PMNs in the presence of CXCL8. FIG. 6E are immunoblots showing the interaction of His-LukE or His-LukD with cell lysates containing HA-tagged CXCR1 or CXCR2. Immunoblots are representative of at least three independent experiments. Means±s.e.m. are shown (n=3).

FIG. 9A shows that the structures of LukE and LukS-PV differ primarily in the rim domain surface as indicated by a color ramp in which highly divergent residues are colored in dark blue, identical residues are colored in red, and conservative substitutions have an intermediate color. FIG. 9B is a structural alignment of LukE (3ROH, light blue) and LukS (1T5R, light green) with DRs 1-5 amino acids highlighted as follows: DR1 (yellow, 57-75), DR2 (grey, 139-150), DR3 (orange, 164-178), DR4 (blue, 182-196) and DR5 (red, 237-271). FIG. 9C shows the viability of PMNs treated with WT and LukE$^{DR}$ hybrids (DRs 1-5, 300 nM). Insert is a coomassie blue-stained gel of purified LukE$^{DR}$ hybrids. FIG. 9D shows the viability of CCR5$^+$ cells treated with the indicated toxins (300 nM). FIG. 9E shows binding of GFP-LukE (300 nM) in the presence of unlabeled LukE or LukE$^{DR4}$ as determined by flow cytometry. FIG. 9F depicts the LukE$^{DR4}$ (blue) structure with residues that differ between LukE and LukS-PV shown as sticks. The graphs of FIGS. 9G and 9H show ex vivo infection of PMNs (FIG. 9G) or HUT-R5 (FIG. 9H) with the indicated S. aureus strains at a multiplicity of infection of 10. *P<0.05; **P≤0.0001 by one-way analysis of variance (d, g). Means±s.e.m. are shown (n=3).

FIG. 11B shows LukE, LukE$^{DR4}$, and LukD levels on S. aureus ΔlukED integration strains or strains complemented with plasmids encoding lukED or lukE$^{DR4}$D as evaluated by immunoblot. As a negative control, a strain lacking lukED and hlgACB (ΔlukED ΔhlgACB) was used. LukE$^{DR4}$ levels produced by lukE$^{DR4}$D appear to be reduced compared to LukE levels produced by lukED. However, comparable levels of LukE and LukE$^{DR4}$ are observed by coomassie blue gel staining on the immunoblot of FIG. 11A, indicating that the apparent reductions in protein level are due to suboptimal antibody recognition of LukE$^{DR4}$ compared to LukE.

FIGS. 12A-12C show that LukED-mediated killing of CXCR1$^+$ and CXCR2$^+$ cells contributes to S. aureus pathogenesis in mouse models of systemic infection. FIG. 12A shows viability of peritoneal elicited murine PMNs (CXCR2$^+$) or macrophages (CCR5$^+$) in the presence of PBS (No Toxin), LukED, or LukE$^{DR4}$D (300 nM). FIG. 12B shows cell death in murine PMNs isolated from the liver (top panel) and kidneys (bottom panel) of mice systemically infected with isogenic S. aureus ΔlukED, ΔlukED::lukED or ΔlukED::lukE$^{DR4}$D strains. FIG. 12C shows 'survival' of mice infected with isogenic S. aureus ΔlukED (n=10), ΔlukED::lukED (+lukED, n=16) or ΔlukED::lukE$^{DR4}$D (+lukE$^{DR4}$D, n=16) strains. FACS plots are representative of one of 3 mice per treatment (FIG. 12A) or one of 10 infected mice per strain (FIG. 12B). Statistical analysis for ΔlukED v+lukED, **p<0.0001; ΔlukED v +lukE$^{DR4}$D, p=0.0577; +lukED v+lukE$^{DR4}$D, *p<0.0003 by one-way analysis of variance (Mantel-Cox test) (FIG. 12C).

FIGS. 13A-13B show ex vivo and in vivo effects of LukED and LukE$^{DR4}$D.

FIG. 13A shows the viability of PMNs or macrophages isolated from murine PECs upon treatment with PBS (no toxin), LukED or LukE$^{DR4}$D. FIG. 13B shows viability of PMNs isolated from liver or kidneys of mice infected with isogenic S. aureus ΔlukED, ΔlukED::lukED or ΔlukED::lukE$^{DR4}$D.

FIGS. 15A-15B demonstrate that LukE's amino acids P184, G186, P187, and G189 within the DR4 domain are required for LukED targeting of CXCR1 and CXCR2+ cells and for the observed lethality of LukED in mice. FIG. 15A shows the viability of hPMNs treated with WT LukED (LukE/LukD) or the LukE$^{P184, G186, P187, G189}$/LukD toxins. Results represent the means and s.e.m. from different human donors (n=8). FIG. 15B shows "survival" of mice upon bloodstream administration of 10 g of each LukE variant in combination with 10 g LukD. Mice (n=5) were treated with an intravenous injection containing the indicated toxin and the time to death recorded and presented as a Kaplan-Meier survival plot.

FIG. 16A shows the susceptibility of RBCs isolated from nine independent human donors. FIG. 16B depicts the data presented in FIG. 16A where the donors were divided into DARC+ and DARC−. Results represent the means and s.e.m. from different human donors (n=5 for DARC+ and 4 for DARC−). FIG. 16C shows that LukED-mediated lysis of RBCs is inhibited by increasing concentrations of purified DARC. Results represent the means and s.e.m. from different human donors (n=3). FIG. 16D shows that LukED-mediated lysis of RBCs is inhibited with a mouse IgG2A anti-DARC monoclonal antibody (clone #358307). Results represent the means and s.e.m. from different human donors (n=3). Statistical significance was determined by Student's t test.

DETAILED DESCRIPTION OF THE INVENTION

Figure 1A:
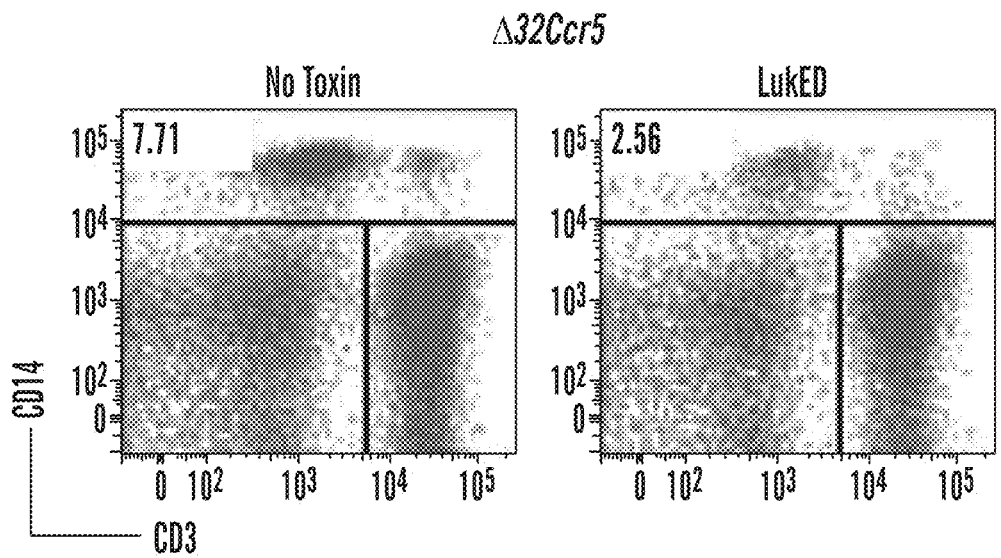
FIGS. 1A-1G demonstrate that LukED targets CXCR1 and CXCR2 to kill monocytes and PMNs.
Figure 1B:
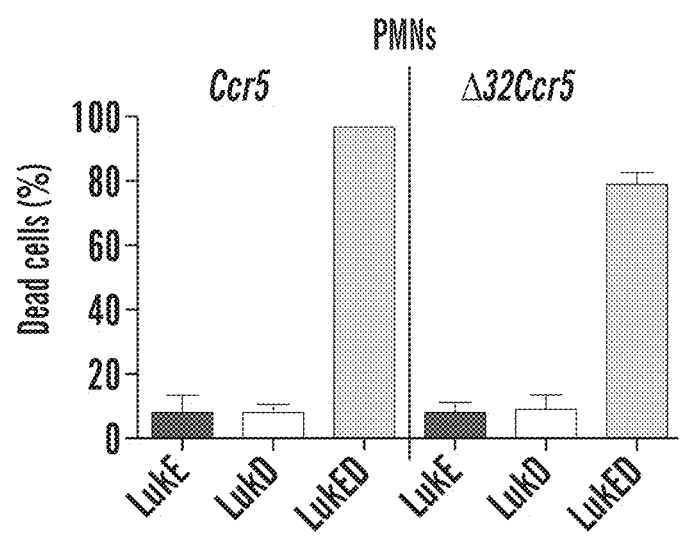

A first aspect of the present invention is directed to a method of preventing or treating Staphylococcus aureus infection and/or a condition resulting from a S. aureus infection in a subject. This method involves selecting a subject having or at risk of having S. aureus infection and administering, to the selected subject, a composition that inhibits S. aureus interaction with CXCR1 and CXCR2 (i.e., by inhibiting CXCR1/CXCR2's interaction with LukE and/or HlgA), under conditions effective to prevent or treat S. aureus infection and/or a condition resulting from a S. aureus infection in the subject.

To date, the majority of *S. aureus* infections are due to MRSA (Moran et al., "Methicillin-Resistant *S. aureus* Infections Among Patients in the Emergency Department," *The New England Journal of Medicine* 355:666-674 (2006), which is hereby incorporated by reference in its entirety). Previously, the majority of MRSA infections were thought to be of nosocomial origin (HA-MRSA), however infections are now occurring in otherwise healthy individuals who have not had exposure to healthcare facilities, i.e., community-associated MRSA (CA-MRSA) (Klevens et al., "Invasive Methicillin-Resistant *Staphylococcus aureus* Infections in the United States," *Jama* 298:1763-1771 (2007) and Klevens et al., "Changes in the Epidemiology of Methicillin-Resistant *Staphylococcus aureus* in Intensive Care Units in US Hospitals, 1992-2003," *Cln. Infect. Dis.* 42:389-391 (2006), which are hereby incorporated by reference in their entirety). These CA-MRSA associated infections are more severe and result in higher mortality rates compared to HA-MRSA infections (Deleo et al., "Community-Associated Methicillin-Resistant *Staphylococcus aureus*," *Lancet* 375:1557-1568 (2010), which is hereby incorporated by reference in its entirety). Recent reports have suggested that the increased virulence of strains associated with CA-MRSA infections compared to those associated with HA-MRSA infections is primarily due to the enhanced ability of CA-MRSA-associated strains to evade neutrophil (PMNs)-mediated killing (Voyich et al., "Insights into Mechanisms Used by *Staphylococcus aureus* to Avoid Destruction by Human Neutrophils," *J. Immunol.* 175:3907-3919 (2005); Wang et al., "Identification of Novel Cytolytic Peptides as Key Virulence Determinants for Community-Associated MRSA," *Nat. Med.* 13:1510-1514 (2007); Li et al., "Evolution of Virulence in Epidemic Community-Associated Methicillin-Resistant *Staphylococcus aureus*," *Proc. Nat'l Acad. Sci. U.S.A.* 106:5883-5888 (2009); Dumont et al., "Characterization of a New Cytotoxin That Contributes to *Staphylococcus aureus* Pathogenesis," *Mol. Microbiol.* 79:814-825 (2011); and Alonzo III et al., "*Staphylococcus aureus* Leucocidin ED Contributes to Systemic Infection by Targeting Neutrophils and Promoting Bacterial Growth in Vivo," *Mol. Microbiol.* 83:423-435 (2012), which are hereby incorporated by reference in their entirety). *S. aureus* avoids PMN-mediated killing by targeting and killing PMNs with a collection of cytotoxins and cytolytic peptides (Wang et al., "Identification of Novel Cytolytic Peptides as Key Virulence Determinants for Community-Associated MRSA," *Nat. Med.* 13:1510-1514 (2007); Dumont et al., "Characterization of a New Cytotoxin That Contributes to *Staphylococcus aureus* Pathogenesis," *Mol. Microbiol.* 79:814-825 (2011); Alonzo III et al., "*Staphylococcus aureus* Leucocidin ED Contributes to Systemic Infection by Targeting Neutrophils and Promoting Bacterial Growth in Vivo," *Mol. Microbiol.* 83:423-435 (2012); Loffler et al., "*Staphylococcus aureus* Panton-Valentine Leukocidin is a Very Potent Cytotoxic Factor for Human Neutrophils," *PLoS Pathog.* 6:e1000715 (2010); and Ventura et al., "Identification of a Novel *Staphylococcus aureus* Two-Component Leukotoxin Using Cell Surface Proteomics," *PLoS One* 5:e11634 (2010), which are hereby incorporated by reference in their entirety). Clinically relevant strains of *S. aureus* can produce up to five different bicomponent leukotoxins: Panton-Valentine leukocidin (PVL or LukFS-PV), leukocidin E/D (LukED), γ-hemolysin (HlgAB and HlgCB), and leukocidin A/B (LukAB; also known as LukGH) (Vandenesch et al., "*Staphylococcus aureus* Hemolysins, Bi-Component Leukocidins, and Cytolytic Peptides: A Redundant Arsenal of Membrane-Damaging Virulence Factors?" *Front. Cell. Infect. Microbiol.* 2:12 (2012), and Alonzo & Torres, "Bacterial Survival Amidst an Immune Onslaught: The Contribution of the *Staphylococcus aureus* Leukotoxins. *PLoS Pathog.* 9:e1003143 (2013), which are hereby incorporated by reference in their entirety). These toxins are each capable of targeting and killing human PMN, but they also exhibit tropism towards additional leukocytes (Alonzo & Torres, "Bacterial Survival Amidst an Immune Onslaught: The Contribution of the *Staphylococcus aureus* Leukotoxins. *PLoS Pathog.* 9:e1003143 (2013); Gravet et al., "Characterization of a Novel Structural Member, LukE-LukD, of the Bi-Component Staphylococcal Leucotoxins Family," *FEBS Lett.* 436:202-8 (1998); Morinaga et al., "Purification, Cloning and Characterization of Variant LukE-LukD With Strong Leukocidal Activity of Staphylococcal Bi-Component Leukotoxin Family," *Microbiol. Immunol.* 47:81-90 (2003); and Perret et al., "Cross-Talk Between *Staphylococcus aureus* Leukocidins-Intoxicated Macrophages and Lung Epithelial Cells Triggers Chemokine Secretion in an Inflammasome-Dependent Manner," *Cell. Microbiol.* 14:1019-36 (2012), which are hereby incorporated by reference in their entirety), suggesting that *S. aureus* uses leukotoxins to deplete the immune cells responsible for protecting the body from infection. In addition to leukocytes, HlgAB, HlgCB and LukED can also lyse red blood cells (RBC) (Morinaga et al., "Purification, Cloning and Characterization of Variant LukE-LukD With Strong Leukocidal Activity of Staphylococcal Bi-Component Leukotoxin Family," *Microbiol. Immunol.* 47:81-90 (2003), which is hereby incorporated by reference in its entirety), which could contribute to *S. aureus* growth in vivo by releasing hemoglobin from RBC for use as an iron source (Torres et al., "*Staphylococcus aureus* Fur Regulates the Expression of Virulence Factors That Contribute to the Pathogenesis of Pneumonia," *Infect. Immun.* 78:1618-28 (2010), which is hereby incorporated by reference in its entirety).

Given the large number of individuals who contract MRSA annually, it is likely that a substantial proportion of these infections will be refractory to traditional courses of antibiotic treatment. An innovative approach to treat such infections is to inhibit *S. aureus* virulence factors, such as LukED and HlgAB, which kill PMNs, the most critical innate immune cell involved in defense against *S. aureus* infection, and lyse red blood cells (RBCs), which provide critical nutrients for bacterial growth. As described herein, applicants have identified CXCR1 and CXCR2, also known as the interleukin 8 receptor α and β chains, respectively, as the cellular receptors for LukED and HlgAB on human PMNs. Additionally, applicants have identified the Duffy antigen receptor for chemokines (DARC) as the cellular receptor for LukED and HlgAB on human RBCs. Binding of LukED and HlgAB to these cellular receptors leads to leukotoxin oligomerization and pore formation leading to cell death. Therefore, agents and compositions which inhibit *S. aureus* LukED and HlgAB interaction with CXCR1/CXCR2 and/or DARC are clinically useful for blocking *S. aureus* cytotoxicity, in turn preventing depletion of PMNs and promoting the natural clearance of *S. aureus* by the innate immune system.

In accordance with this aspect of the present invention, a suitable composition for inhibiting *S. aureus* interaction with CXCR1 and CXCR2 comprises an agent that inhibits both CXCR1 and CXCR2 (referred to as a CXCR1/CXCR2 inhibitor or antagonist). Suitable agents that inhibit both CXCR1 and CXCR2 include inhibitor proteins and peptides, antibodies, and small molecules that are well known in the art and described in more detail below.

Suitable peptide inhibitors of CXCR1/CXCR2 include those derived from the CXCR1 and CXCR2 receptor ligand, CXC chemokine ligand 8 (CXCL8; also known as interleukin 8) as described by Li et al., "CXCL8$_{(3-74)}$K11R/G31P Antagonizes Ligand Binding to the Neutrophil CXCR1 and CXCR2 Receptors and Cellular Responses to CXCL8/IL-8," *Biochem. Biophys. Res. Comm.* 293(3): 939-944 (2002); U.S. Pat. No. 8,039,429 to Gordon, and U.S. Pat. No. 7,201,895 to Gordon et al., which are hereby incorporated by reference in their entirety. Exemplary peptide inhibitors derived from CXCL8 include, without limitation CXCL8$_{(3-74)}$K11R/G31P having an amino acid sequence of SEQ ID NO:1 as shown below.

```
Thr Glu Leu Arg Cys Gln Cys Ile Arg Thr His Ser Thr
1               5                   10

Pro Phe His Pro Lys Phe Ile Lys Glu Leu Arg Val Ile
    15              20                  25

Glu Ser Pro Pro His Cys Glu Asn Ser Glu Ile Ile Val
            30                  35

Lys Leu Thr Asn Gly Asn Glu Val Cys Leu Asn Pro Lys
40              45                      50

Glu Lys Trp Val Gln Lys Val Val Gln Val Phe Val Lys
        55              60                      65

Arg Ala Glu Lys Gln Asp Pro
                70
```

Analogues of CXCL8$_{(3-74)}$K11R/G31P, such as CXCL8$_{(3-74)}$K11R/G31P/P32G having an amino acid sequence of SEQ ID NO:2 (shown below) and CXCL8$_{(3-74)}$K11R/T12S/H13F/G31P having an amino acid sequence of SEQ ID NO:3 (shown below) are also suitable for use in the methods of the present invention.

```
CXCL8 (3-74) K11R/G31P/P32G
                                       SEQ ID NO: 2
Thr Glu Leu Arg Cys Gln Cys Ile Arg Thr His Ser Thr
1               5                   10

Pro Phe His Pro Lys Phe Ile Lys Glu Leu Arg Val Ile
    15              20                  25

Glu Ser Gly Gly His Cys Glu Asn Ser Glu Ile Ile Val
            30                  35

Lys Leu Thr Asn Gly Asn Glu Val Cys Leu Asn Pro Lys
40              45                      50

Glu Lys Trp Val Gln Lys Val Val Gln Val Phe Val Lys
        55              60                      65

Arg Ala Glu Lys Gln Asp Pro;
                70

CXCL8 (3-74) K11R/T12S/H13F/G31P
                                       SEQ ID NO: 3
Thr Glu Leu Arg Cys Gln Cys Ile Arg Ser Pro Ser Thr
1               5                   10

Pro Phe His Pro Lys Phe Ile Lys Glu Leu Arg Val Ile
    15              20                  25

Glu Ser Pro Pro His Cys Glu Asn Ser Glu Ile Ile Val
            30                  35

Lys Leu Thr Asn Gly Asn Glu Val Cys Leu Asn Pro Lys
40              45                      50

Glu Lys Trp Val Gln Lys Val Val Gln Val Phe Val Lys
        55              60                      65

Arg Ala Glu Lys Gln Asp Pro;
                70
```

Other CXCL8 derived peptides that similarly function as inhibitors of CXCR1/CXCR2 disclosed in U.S. Pat. No. 8,039,429 to Gordon and U.S. Pat. No. 7,201,895 to Gordon et al., which are hereby incorporated by reference in their entirety, are also suitable for use in accordance with this aspect of the present invention.

Other suitable peptide inhibitors of CXCR1/CXCR2 include recombinant peptides comprising the *S. aureus* CXCR1/CXCR2 receptor binding domain sequence. As described herein, applicants have identified the regions of *S. aureus* LukE and HlgA toxins that bind to CXCR1 and CXCR2. Consequently, peptides comprising these amino acid residues constitute suitable CXCR1/CXCR2 inhibitory peptides. Therefore, in one embodiment of the present invention, a suitable peptide inhibitor of CXCR1/CXCR2 comprises an amino acid sequence corresponding to amino acid residues 182-196 of the soluble LukE protein (*S. aureus* Newman strain; SEQ ID NO:4, shown below).

```
Asn Thr Asn Ile Glu Asn Ile Gly Asp Gly Ala Glu Val
1               5                   10

Ile Lys Arg Thr Glu Asp Val Ser Ser Lys Lys Trp Gly
    15                  20                  25

Val Thr Gln Asn Val Gln Phe Asp Phe Val Lys Asp Lys
            30                  35                  40

Lys Tyr Asn Lys Asp Ala Leu Ile Val Lys Met Gln Gly
                    45                  50

Phe Ile Asn Ser Arg Thr Ser Phe Ser Asp Val Lys Gly
        55                  60                  65

Ser Gly Tyr Glu Leu Thr Lys Arg Met Ile Trp Pro Phe
                70                  75

Gln Tyr Asn Ile Gly Leu Thr Thr Lys Asp Pro Asn Val
    80                  85                  90

Ser Leu Ile Asn Tyr Leu Pro Lys Asn Lys Ile Glu Thr
            95                  100

Thr Asp Val Gly Gln Thr Leu Gly Tyr Asn Ile Gly Gly
105                 110                 115

Asn Phe Gln Ser Ala Pro Ser Ile Gly Gly Asn Gly Ser
        120                 125                 130

Phe Asn Tyr Ser Lys Thr Ile Ser Tyr Thr Gln Lys Ser
                135                 140

Tyr Val Ser Glu Val Asp Lys Gln Asn Ser Lys Ser Val
    145                 150                 155

Lys Trp Gly Val Lys Ala Asn Glu Phe Val Thr Pro Asp
            160                 165

Gly Lys Lys Ser Ala His Asp Arg Tyr Leu Phe Val Gln
170                 175                 180

Ser Pro Asn Gly Pro Thr Gly Ser Ala Arg Glu Tyr Phe
        185                 190                 195

Ala Pro Asp Asn Gln Leu Pro Pro Leu Val Gln Ser Gly
                200                 205

Phe Asn Pro Ser Phe Ile Thr Thr Leu Ser His Glu Lys
    210                 215                 220

Gly Ser Ser Asp Thr Ser Glu Phe Glu Ile Ser Tyr Gly
            225                 230

Arg Asn Leu Asp Ile Thr Tyr Ala Thr Leu Phe Pro Arg
235                 240                 245

Thr Gly Ile Tyr Ala Glu Arg Lys His Asn Ala Phe Val
        250                 255                 260

Asn Arg Asn Phe Val Val Arg Tyr Glu Val Asn Trp Lys
                265                 270

Thr His Glu Ile Lys Val Lys Gly His Asn
    275                 280
```

A CXCR1/CXCR2 peptide inhibitor comprising at least the amino acid sequence of QSPNGPTGSAREYFA (SEQ ID NO:5; i.e., residues 182-196 of SEQ ID NO:4), may contain additional amino acid residues at its N- or C-terminus that do not alter its ability to bind to CXCR1 or CXCR2, but function to enhance stability or target delivery of the inhibitory peptide.

In another embodiment of the present invention, a suitable peptide inhibitor of CXCR1/CXCR2 comprises an amino acid sequence corresponding to amino acid residues 180-192 of the soluble HlgA protein (S. aureus Newman strain; SEQ ID NO:6, shown below).

```
Glu Asn Lys Ile Glu Asp Ile Gly Gln Gly Ala Glu Ile
1               5                   10
Ile Lys Arg Thr Gln Asp Ile Thr Ser Lys Arg Leu Ala
        15              20              25
Ile Thr Gln Asn Ile Gln Phe Asp Phe Val Lys Asp Lys
                30              35
Lys Tyr Asn Lys Asp Ala Leu Val Val Lys Met Gln Gly
40              45              50
Phe Ile Ser Ser Arg Thr Thr Tyr Ser Asp Leu Lys Lys
            55              60              65
Tyr Pro Tyr Ile Lys Arg Met Ile Trp Pro Phe Gln Tyr
                70              75
Asn Ile Ser Leu Lys Thr Lys Asp Ser Asn Val Asp Leu
80              85              90
Ile Asn Tyr Leu Pro Lys Asn Lys Ile Asp Ser Ala Asp
                95              100
Val Ser Gln Lys Leu Gly Tyr Asn Ile Gly Gly Asn Phe
105             110             115
Gln Ser Ala Pro Ser Ile Gly Gly Ser Gly Ser Phe Asn
        120             125             130
Tyr Ser Lys Thr Ile Ser Tyr Asn Gln Lys Asn Tyr Val
                135             140
Thr Glu Val Glu Ser Gln Asn Ser Lys Gly Val Lys Trp
        145             150             155
Gly Val Lys Ala Asn Ser Phe Val Thr Pro Asn Gly Gln
                160             165
Val Ser Ala Tyr Asp Gln Tyr Leu Phe Ala Gln Asp Pro
170             175             180
Thr Gly Pro Ala Ala Arg Asp Tyr Phe Val Pro Asp Asn
            185             190             195
Gln Leu Pro Pro Leu Ile Gln Ser Gly Phe Asn Pro Ser
                200             205
Phe Ile Thr Thr Leu Ser His Glu Arg Gly Lys Gly Asp
    210             215             220
Lys Ser Glu Phe Glu Ile Thr Tyr Gly Arg Asn Met Asp
            225             230
Ala Thr Tyr Ala Tyr Val Thr Arg His Arg Leu Ala Val
235                 240             245
Asp Arg Lys His Asp Ala Phe Lys Asn Arg Asn Val Thr
        250             255             260
Val Lys Tyr Glu Val Asn Trp Lys Thr His Glu Val Lys
                265             270
Ile Lys Ser Ile Thr Pro Lys
    275             280
```

A CXCR1/CXCR2 peptide inhibitor comprising at least the amino acid sequence of QDPTGPAARDYFV (SEQ ID NO:7; i.e., residues 180-192 of SEQ ID NO:6), may contain additional amino acid residues at its N- or C-terminus that do not alter its ability to bind to CXCR1 or CXCR2, but function to enhance stability or target delivery of the inhibitory peptide.

Compositions suitable for use in the methods of the present invention may alternatively comprise a small molecule that inhibits both CXCR1 and CXCR2. Numerous small molecule inhibitors or antagonists of CXCR1/CXCR2 are known in the art and are suitable for use in the methods of the present invention.

A first class of exemplary small molecule CXCR1/CXCR2 inhibitors suitable for use in the methods of the present invention include (2R)-2-phenylpropanamides bearing a 4-sulfonylamino substituent at position four of the phenyl group (see U.S. Pat. Nos. 7,652,169 and 7,868,046 to Allegretti et al. (Dompe S. P. A.), which is hereby incorporated by reference in its entirety). This class of compounds has a general formula of Formula I below:

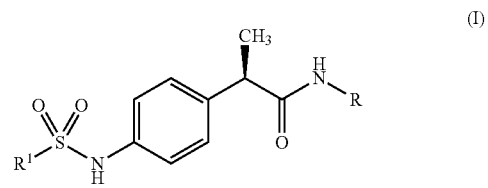

(I)

wherein

R of Formula I is selected from

H, OH, $C_1$-$C_5$-alkyl, $C_3$-$C_6$-cycloalkyl, $C_2$-$C_5$-alkenyl, $C_1$-$C_5$-alkoxy and phenyl;

an heteroaryl group selected from substituted and unsubstituted pyrrole, thiophene, furane, indole, imidazole, thiazole, oxazole, pyridine and pirimidine;

a residue of formula —$CH_2$—$CH_2$—O—($CH_2$—$CH_2$)nR", wherein R" is H or $C_1$-$C_5$-alkyl, n is an integer from 0 to 2;

or R of Formula I, together with the NH group to which is coupled, is a radical group of primary amides of natural amino acids such as (2S)-2-aminopropanamide, (2S)-2-amino-3-phenylpropanamide, (2S)-2-amino-3-hydroxypropanamide, (2S)-2-amino-3-carboxypropanamide, (2S)-2,6-diaminoexanamide. The NH group mentioned above, as a part of a radical group of primary amides of natural amino acids, represents the amino group of the natural amino acid.

R' of Formula I is selected from linear or branched $C_1$-$C_5$-alkyl, $C_3$-$C_6$-cycloalkyl, $C_2$-$C_5$-alkenyl and trifluoromethyl;

substituted or unsubstituted phenyl;

substituted or unsubstituted benzyl;

an heteroaryl group selected from substituted and unsubstituted pyridine, pirimidine, pyrrole, thiophene, furane, indole, thiazole and oxazole.

Exemplary (2R)-2-phenylpropanamides compounds suitable for use in the methods of the present invention include, without limitation, (2R)-2-{4-[(isopropylsulfonyl]amino}phenyl)propanamide; (2R)-2-{4 [(isopropylsulfonyl]amino}phenyl)propanamide sodium salt; (2R)-2-{4-{[(2-chlorophenyl)sulfonyl]amino}phenyl)propanamide; (2R)-2-{4-{[(2,6-dichlorophenyl)sulfonyl]amino}phenyl) propanamide; (2R)-2-{4-[(methylsulfonyl)amino]phenyl}propanamide; (2R)-2-{4-[(phenylsulfonyl)amino]phenyl}propanamide; (2R)-2-{4-{[(4-methylphenyl)sulfonyl]amino}phenyl)propanamide; (2R)-2-{4-{[(4- methoxylphenyl)sulfonyl]amino}phenyl)propanamide; (2R)-2-(4-[(benzylsulfonyl]amino}phenyl)propanamide; (2R)-2-(4-{[(4-chlorophenyl)sulfonyl]amino}phenyl)propanamide; (2R)-2-(4-{[(4-(trifluoromethyl)phenyl]sulfonyl}amino)phenyl]propanamide; (2R)-2-{4-[(thien-2ylsulfonyl)amino]phenyl}propanamide; (2R)-2-{4-[(cyclopentylsulfonyl)amino]phenyl}propanamide; (2R)-2-(4-{[(trifluoromethyl)sulfonyl]amino}phenyl)propanamide; (2R)-2-{4-[(isopropylsulfonyl]amino}phenyl)-N-methyl-propanamide; (2R)—N-[(1S)-2-amino-1-methyl-2-oxoethyl]-2-{4-[(isopropylsulfonyl]amino}phenyl)propanamide; (2R)-2-{4-[(isopropylsulfonyl]amino}phenyl)-N-[4-(trifluoromethyl)-1,3-thiazol-2-yl]propanamide; (2R)-2-{4-{[(2-chlorophenyl)sulfonyl]amino}phenyl)-N-[4-(trifluoromethyl)-1,3-thiazol-2-yl]propanamide; (2R)-2-{4-{[(2-chlorophenyl)sulfonyl]amino}phenyl)-N-[2-(2-hydroxyethoxy)ethyl]propanamide; (2R)-2-{4-{[(2-chlorophenyl)sulfonyl]amino}phenyl)-N-cyclopropyl propanamide.

Another class of exemplary small molecule CXCR1/CXCR2 inhibitors suitable for use in the methods of the present invention include those described in U.S. Patent Publication No. 20120202884 to Piemonti et al. (Dompe S. P. A), which is hereby incorporated by reference in its entirety, having a general formula of Formula II as shown below:

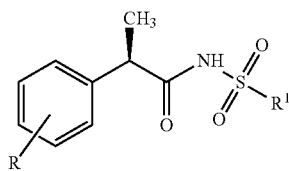

(II)

wherein R of Formula II is selected from linear or branched 4-($C_1$-$C_6$)alkyl, 4-trifluoromethanesulfonyloxy or 3-benzoyl and R of Formula II is linear or branched ($C_1$-$C_6$)alkyl.

Exemplary compounds of Formula II suitable for use in the methods of the present invention include, without limitation, R(−)-2-[(4-isobutylphenyl)propionyl]-methanesulfonamide (also known as Repertaxin or Reparixin), R(−)-2-[(4'-trifluoromethanesulfonyloxy)phenyl]propionyl-methanesulfonamide (also known as Meraxin).

Another class of exemplary small molecule CXCR1/CXCR2 inhibitors suitable for use in the methods of the present invention include derivatives of 2-arylphenylpropionic acids as described by Bertini et al. "Noncompetitive Allosteric Inhibitors of the Inflammatory Chemokine Receptors CXCR1 and CXCR2: Prevention of Reperfusion Injury," *Proc Natl Acad Sci USA*. 101:11791-11796 (2004); Bizzarri et al., "ELR+ CXC Chemokines and Their Receptors (CXC Chemokine Receptor 1 and CXC Chemokine Receptor 2) as New Therapeutic Targets," *Pharmacol Ther.* 112:139-149 (2006); and Souza et al., "Repertaxin, A Novel Inhibitor of Rat CXCR2 Function, Inhibits Inflammatory Responses that Follow Intestinal Ischaemia and Reperfusion Injury," *Br J Pharmacol.* 143:132-142 (2004), which are hereby incorporated by reference in their entirety). An exemplary compound in this class of CXCR1/CXCR2 inhibitors includes 4-[(1R)-2-amino-1-methyl-2-oxoethyl] phenyl trifluoromethane sulfonate (DF 2162) having the structure of Formula III below and derivatives thereof.

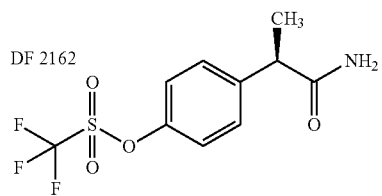

(III)

Another class of exemplary small molecule CXCR1/CXCR2 inhibitors include pyridine- and pyrimidinecarboxamide compounds as disclosed in U.S. Patent Publication No. 2010/0210593 to Maeda et al. (Syntrix Biosystems), which is hereby incorporated by reference in its entirety, which have the formulas of Formula IV and V as shown below:

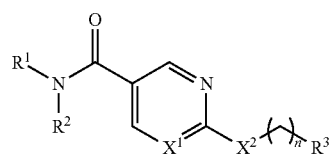

(IV)

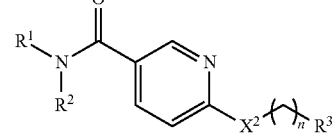

(V)

wherein $R^1$ and $R^2$ of Formula IV and V are independently selected from the group consisting of hydrogen, 2- or 3- or 4-halo-phenyl, heteroalkyl, alkyl, aryl, arylalkyl, heteroaryl, heteroarylalkyl, cycloalkyl, cycloalkylalkyl, heterocyclyl, and heterocyclylalkyl;

wherein $R^3$ of Formula IV and V is selected from —B($R^4R^5$), —$R^6$—B($R^4R^5$), $R^6$, —C(O)—$R^6$, —O—$R^6$, —S(O)$_y$—$R^6$ (wherein y=0, 1, or 2), —P(O)—($R^4R^5$) and —N($R^7R^8$);

wherein $R^6$ of Formula IV and V is selected from alkyl, aryl, arylalkyl, cycloalkyl, heteroaryl, heteroarylalkyl, heterocyclyl and heterocyclylalkyl;

wherein $R^4$ and $R^5$ of Formula IV and V are independently hydrogen, hydroxyl, aryloxy, or alkoxy, or wherein $R^4$ and $R^5$ together form a cyclic ester, or an acid anhydride (either mixed or symmetrical);

wherein $R^7$ and $R^8$ of Formula IV and V are independently selected from hydrogen, alkyl, haloalkyl, aryl, cycloalkyl, arylalkyl, heteroalkyl, heterocyclyl and heterocyclylalkyl; $R^7$ and $R^8$ are both oxygen to form a nitro group; or $R^7$ and $R^8$ together with the nitrogen to which they are attached, form a heterocyclyl; and wherein $X^1$ of Formula IV and V is carbon or nitrogen; $X^2$ of Formula IV and V is —S(O)$_y$— (wherein y=0, 1, or 2), nitrogen, or oxygen; and n Formula IV and V is an integer between 0 and 8

Other well known small molecule CXCR1/CXCR2 inhibitors include, without limitation, 2-hydroxy-N,N,-dimethyl-3-[[2-[[1(R)-(5-methyl-2-furanyl)propyl]amino]-3,4-dioxo-1-cyclobuten-1-yl]amino]benzamide (SCH-527123) (see U.S. Pat. No. 8,183,287 to Kou et al., which is hereby incorporated by reference in its entirety), N-(2-hydroxy-3-dimethylsulfonylamido-4-chlorophenyl)-N'-(2-bromophenyl)-N"-cyanoguanidine (SCH468477), SCH-479833, and derivatives thereof (see Singh et al., "Small-Molecule Antagonists for CXCR2 and CXCR1 Inhibit Human Melanoma Growth by Decreasing Tumor Cell Proliferation, Survival, and Angiogenesis," *Clin. Cancer Res.* 15: 2380 (2009), which is hereby incorporated by reference in its entirety). Additional small molecule CXCR1/CXCR2 inhibitors that are suitable for use in the present invention include those described in U.S. Pat. No. 7,326,729 to Chao et al., which is hereby incorporated by reference in its entirety.

In another embodiment of this aspect of the present invention, a suitable composition for inhibiting *S. aureus* interaction with CXCR1 and CXCR2 comprises an agent that inhibits CXCR1 and an agent that inhibits CXCR2. Suitable CXCR2 inhibitors include, without limitation, N-(2-hydroxy-4-nitrophenyl)-N'-(2-bromophenyl)urea (SB 225002) (White et al., "Identification of a Potent, Selective Non-Peptide CXCR2 Antagonists That Inhibits Interleukin-8-Induced Neutrophil Migration," *J. Biol. Chem.* 273: 10095-10098 (1998), which is hereby incorporated by reference in its entirety), N-(3-(aminosulfonyl)-4-chloro-2-hydroxyphenyl)-N'-(2,3-dichlorophenyl) urea (Podolin et al, "A Potent and Selective Nonpeptide Antagonist of CXCR2 Inhibits Acute and Chronic Models of Arthritis in the Rabbit," *J. Immunology* 169(11):6435-6444 (2002), which is hereby incorporated by reference in its entirety), N-(2-hydroxy-3-sulfamyl-4-chlorophenyl)-N'-(2,3 dichlorophenyl)urea (SB-332235), SB-656933, aminopyridine and amino pyrimidine carboxamides as disclosed in WO2012027289 to Maeda et al., which is hereby incorporated by reference in it entirety, thiazolo (4,5-D) pyrimidine compounds as disclosed is WO2001/025242 to Willis et al., which is hereby incorporated by reference in its entirety, and squaramide derivatives as disclosed in U.S. Patent Publication Nos. US 2010029670 to Baettig et al. and US20100152205 to Hunt et al., which are hereby incorporated by reference in their entirety. Additional small molecule CXCR2 inhibitors that are suitable for use in the present invention include those described in U.S. Pat. No. 7,579,342 to Bonnert et al. and U.S. Patent Publication No. 20050272750 to Brough et al., which is hereby incorporated by reference in its entirety.

In another embodiment of this aspect of the present invention, the composition comprises one or more antibodies that inhibit *S. aureus* interaction with CXCR1 and CXCR2. Suitable antibodies include a CXCR1 blocking antibody or antibody binding portion thereof (see e.g., Ginestier et al., "CXCR1 Blockade Selectively Targets Human Breast Cancer Stem Cells In Vitro and In Xenografts," *J. Clin. Invest.* 120(2): 485-497 (2010), which is hereby incorporated by reference in its entirety), a CXCR2 blocking antibody or antibody binding portion thereof (see e.g., Nemzek et al., "Functional Contribution of CXCR2 to Lung Injury After Aspiration of Acid and Gastric Particulates," *Am. J. Physiol. Lung Cell Mol. Physiol.* 298(3):L382-L391 (2010), which is hereby incorporated by reference in its entirety), or a combination of CXCR1 and CXCr2 antibodies. Alternatively suitable antibodies include those that bind to the regions of *S. aureus* LukE and HlgA proteins that interact with CXCR1 and CXCR2. An exemplary antibody of this type includes an antibody, or antibody binding portion thereof, that recognizes and binds to an epitope of *S. aureus* LukE comprising an amino acid sequence of SEQ ID NO:5 (QSPNGPTGSAREYFA), corresponding to amino acid residues 182-196 of SEQ ID NO:4. Another exemplary antibody of this type includes an antibody, or antibody binding portion thereof, that recognizes and binds to an epitope of *S. aureus* HlgA comprising an amino acid sequence of SEQ ID NO:7 (QDPTGPAARDYFV), corresponding to amino acid residues 180-192 of SEQ ID NO:6. Antibodies that bind to CXCR1/CXCR2 receptor binding regions of LukE and HlgA are described in more detail below.

Another aspect of the present invention is directed a method of preventing or treating *Staphylococcus aureus* infection and/or a condition resulting from a *S. aureus* infection in a subject. This method involves selecting a subject having or at risk of having *S. aureus* infection and administering, to the selected subject, a composition that inhibits *S. aureus* interaction with Duffy antigen receptor for chemokines (DARC) (i.e., by inhibiting DARC's interaction with LukE and/or HlgA), under conditions effective to prevent or treat *S. aureus* infection and/or a condition resulting from a *S. aureus* infection in the subject.

Suitable compositions for inhibiting *S. aureus* interaction with DARC include DARC inhibitors or antagonists. An exemplary DARC inhibitor for use in the methods of the present invention is a DARC blocking antibody (see e.g., Patterson et al., "Expression of the Duffy Antigen/Receptor for Chemokines (DARC) by the Inflamed Synovial Endothelium," J. Pathol. 197(1):108-116 (2002), which is hereby incorporated by reference in its entirety).

Subjects suitable for treatment in accordance with the methods of the present invention include, without limitation, any animal, preferably, a mammal, more preferably a human. Suitable subjects include both immunocompromised and non-immunocompromised infants, juveniles, and adults. In one embodiment of the present invention the subject has or is at risk of having a methicillin-resistant *S. aureus* (MRSA) infection. In another embodiment of the present invention, the subject has or is at risk of having a methicillin sensitive *S. aureus* (MSSA) infection. Other suitable subjects include those subjects which may have or are at risk for developing a condition resulting from a *S. aureus* infection, i.e., a *S. aureus* associated condition, such as, for example, skin wounds and infections, tissue abscesses, folliculitis, osteomyelitis, pneumonia, scalded skin syndrome, septicemia, septic arthritis, myocarditis, endocarditis, and toxic shock syndrome.

In one embodiment of the present invention, the compositions of the present invention are administered prophylactically to prevent, delay, or inhibit the development of *S. aureus* infection in a subject at risk of getting a *S. aureus* infection or associated condition. In some embodiments of the present invention, prophylactic administration of one or more compositions of the present invention is effective to fully prevent *S. aureus* infection in an individual. In other embodiments, prophylactic administration is effective to prevent the full extent of infection that would otherwise develop in the absence of such administration, i.e., substantially prevent, inhibit, or minimize *S. aureus* infection in an individual.

In another embodiment of the present invention, the compositions of the present invention are administered therapeutically to an individual having a *S. aureus* infection to inhibit the progression and further development of the infection, i.e., to inhibit and/or prevent the spread of the infection to other cells in an individual, decrease infection, and to treat or alleviate one or more symptoms of infection.

The therapeutic compositions of the present invention can be administered as part of a combination therapy in conjunction with one or more other active agents, depending upon the nature of the *S. aureus* infection that is being treated. Such additional active agents include anti-infective agents, antibiotic agents, and antimicrobial agents.

Representative anti-infective agents that may be useful in the present invention include vancomycin and lysostaphin. Other anti-infective agents include a LukAB inhibitor as described in U.S. Patent Application Publication No. 2011/0274693 to Torres et al., which is hereby incorporated by reference in its entirety; a LukED inhibitor or antibody as described in U.S. Patent Publication No. 2013/0017203 to Torres et al., which is hereby incorporated by reference in its entirety; a CCR5 inhibitor as described in U.S. Patent Publication No. 2013/0039885 to Torres et al., which is hereby incorporated by reference in its entirety, and a CD11b inhibitor as described in International Patent Application Serial No. PCT/US2013/032436 to Torres et al., which is hereby incorporated by reference in its entirety.

Representative antibiotic agents and antimicrobial agents that may be useful in the present invention include penicillinase-resistant penicillins, cephalosporins and carbapenems, including vancomycin, lysostaphin, penicillin G, ampicillin, oxacillin, nafcillin, cloxacillin, dicloxacillin, cephalothin, cefazolin, cephalexin, cephradine, cefamandole, cefoxitin, imipenem, meropenem, gentamycin, teicoplanin, lincomycin and clindamycin. Dosages of these antibiotics are well known in the art (see, e.g. MERCK MANUAL OF DIAGNOSIS AND THERAPY (Beers & Berkow eds., 2004), which is hereby incorporated by reference in its entirety). The anti-infective, antibiotic and/or antimicrobial agents may be combined prior to administration, or administered concurrently (as part of the same composition or by way of a different composition) or sequentially with the compositions of the present invention. In certain embodiments, the administering is repeated.

Therapeutic compositions of the present invention may be administered in a single dose, or in accordance with a multi-dosing protocol. For example, in one embodiment of the present invention, relatively few doses of the therapeutic composition are administered, such as one or two doses. In another embodiment of the present invention, the therapeutic composition is administered more frequently, e.g., daily until the level of infection decreases or is gone. In embodiments that include conventional antibiotic therapy, which generally involves multiple doses over a period of days or weeks, the antibiotics can be taken one, two or three or more times daily for a period of time, such as for at least 5 days, 10 days or even 14 or more days, while the compositions of the present invention are administered only once or twice. However, the different dosages, timing of dosages, and relative amounts of the therapeutic composition and antibiotics can and should be selected and adjusted by one of ordinary skill in the art based on the subject and infection being treated.

In the context of using compositions that inhibit LukE and/or HlgA binding to CXCR1/CXCR2 and/or DARC to prevent a *S. aureus* infection, the concentration of the these composition must be adequate to achieve the prevention or substantial prevention of *S. aureus* infection, particularly the prevention of *S. aureus* in susceptible populations (i.e., an infant, juvenile, adult, or an immunocompromised infant, juvenile, or adult). In the context of using therapeutic compositions to treat a *S. aureus* infection, the dosage of an inhibitory composition is one that is adequate to inhibit LukE and/or HlgA mediated cytotoxicity and is capable of achieving a reduction in a number of symptoms, a decrease in the severity of at least one symptom, or a delay in the further progression of at least one symptom, or even a total alleviation of the infection or symptoms thereof.

A therapeutically effective amount of an agent or composition of the present invention is determined in accordance with standard procedures, which take numerous factors into account, including, for example, the concentrations of these active agents in the composition, the mode and frequency of administration, the severity of the *S. aureus* infection to be treated or prevented, and subject details, such as age, weight and overall health and immune condition. General guidance can be found, for example, in REMINGTON'S PHARMACEUTICAL SCIENCES (Mack Publishing Company 1990), which is hereby incorporated by reference in its entirety. A clinician may administer a composition that inhibits LukE and/or HlgA until a dosage is reached that provides the desired or required prophylactic or therapeutic effect. The progress of this therapy can be easily monitored by conventional assays.

The agents and compositions of the present invention can be administered by parenteral, topical, intravenous, oral, subcutaneous, intraperitoneal, intranasal or intramuscular means for prophylactic and/or therapeutic treatment.

The agents and compositions of the present invention may be formulated for parenteral administration. Solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

Pharmaceutical formulations suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

When it is desirable to deliver the agents and compositions of the present invention systemically, they may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Intraperitoneal or intrathecal administration of the agents of the present invention can also be achieved using infusion pump devices such as those described by Medtronic, Northridge, Calif. Such devices allow continuous infusion of desired compounds avoiding multiple injections and multiple manipulations.

In addition to the formulations described previously, the agents may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

Another aspect of the present invention is directed to a method of treating a subject having a *S. aureus* infection. This method involves obtaining a sample from the subject having *S. aureus* infection and quantifying expression levels of CXCR1, CXCR2, DARC or a combination thereof in the sample. The method further involves administering a treatment for the subject based on the quantified expression levels.

In accordance with this aspect of the present invention, the sample from the subject may comprise a blood, tissue, cell, or serum sample.

In one embodiment of this aspect of the invention, quantifying expression levels of CXCR1, CXCR2, DARC involves measuring CXCR1, CXCR2, and/or DARC mRNA expression in the sample from the subject. Methods of detecting and quantifying mRNA expression levels in a sample are well known in the art and generally described below.

mRNA from a subject can be isolated and prepared from tissue or cell samples using methods known in the art. The RNA preparation must produce enzymatically manipulatable mRNA or analyzable RNA. Total RNA and mRNA may be isolated using known methods in the art, including, but not limited to guanidinium isothiocyanate-ultracentrifugation, guanidinium and phenol-chloroform extraction, lithium chloride-SDS urea extraction, or by the oligo (dT) cellulose method. Total isolated RNA can be used to generate first strand copy DNA (cDNA) using any known procedure in the art, for example, using random primers, oligo-dT primers, or random-oligo-dT primers. The cDNA is then used as a template for a first round amplification reaction or for a quantitative PCR reaction depending on target or sample abundance. The first round PCR amplification is performed with a primer set, including forward and reverse primers that are specific for the target gene of interest (i.e., CXCR1, CXCR2, or DARC). Following the first round of amplification, a cleaned portion of the reaction product is used for quantitative analysis. Quantitative real-time PCR protocols typically rely on fluorescent detection of product formation following the extension phase of the reaction cycle. Typical fluorescent approaches for quantitative PCR are based on a fluorescent reporter dyes such as SYBR green, FAM, fluorescein, HEX, TET, TAMRA, etc. and quencher dyes such as DABSYL, Black Hole, etc. Systems, such as Molecular Beacons (Integrated DNA Technologies, Coralville, Iowa), Taqman® Probes (Applied Biosystems, Foster City, Calif.), LNA or MGB Probes, Scorpion® Primers (DxS Ltd., Manchester, UK), AmpliFluor, Plexor, or Lux primers are also well known in the art of quantitative gene analysis. Examples of methods and reagents related to real time probes can be found in U.S. Pat. Nos. 5,925,517, 6,103,476, 6,150,097, and 6,037,130 all to Tyagi et al., which are hereby incorporated by reference in their entirety.

Quantitative gene expression can be expressed as absolute copy number or as relative gene expression. Both methods utilize a standard curve from which to accurately obtain quantitative data from. The measured mRNA expression level in the sample is typically compared to the mRNA expression level measured in a reference or control sample, e.g., the average expression level in a control population, the average expression level in a clinical population of patients with a known susceptibility to *S. aureus* infection, and/or an average expression level in a clinical population of patients with a know resistance to *S. aureus* infection.

In another embodiment of this aspect of the invention, quantifying expression levels of CXCR1, CXCR2, DARC involves measuring CXCR1, CXCR2, and/or DARC protein expression in the sample from the subject. Methods of detecting and quantifying protein expression levels in a sample are well known in the art and generally described below.

Sample protein from the subject can be isolated and prepared from a sample using standard preparation methods known in the art. For example, cells can be lysed in buffer containing a detergent, such as sodium dodecyl sulfate (SDS), and a cocktail of protease inhibitors. Protein yield can be determined using the Bradford Assay or any variation of the method known in the art. Assessing the level of expression of a target protein within a sample can be performed by various techniques known in the art. For example, assessing the level of expression can involve analyzing one or more proteins by two-dimensional gel electrophoresis, mass spectroscopy, high performance liquid chromatography (HPLC), fast protein liquid chromatography, multi-dimensional liquid chromatography followed by tandem mass spectrometry, or protein chip expression analysis. Other techniques involve contacting the sample with one or more detectable reagents that is suitable for measuring protein expression, e.g., a labeled antibody having binding specificity for CXCR1, CXCR2, or DARC, or a primary antibody having binding specificity for CXCR1, CXCR2, or DARC, used in conjunction with a secondary antibody, and measuring protein expression level based on the level of detectable reagent in the sample after normalizing to total protein in the sample. Suitable methods for detecting protein expression level in a sample, e.g., a blood or serum sample, that are commonly employed in the art include, for example and without limitation, western blot, immunoprecipitation, enzyme-linked immunosorbent assay (ELISA), radioimmunoassay (RIA), or fluorescent activated cell sorting (FACS). The measured protein expression level in the sample is typically compared to the protein expression level measured in a reference or control sample, e.g., the average expression level in a control population, the average expression level in a clinical population of patients with a known susceptibility to *S. aureus* infection, and/or an average expression level in a clinical population of patients with a know resistance to *S. aureus* infection.

In accordance with this aspect of the present invention, an increased or high-level of CXCR1, CXCR2, or DARC expression as compared to the expression level in a normal reference population or a similar level of CXCR1, CXCR2, or DARC expression as compared to the expression level in a reference population having a known susceptibility to *S. aureus* infection, would generally indicate that the subject may have an increased susceptibility or heightened sensitivity to *S. aureus* infection. Accordingly, a more aggressive therapeutic treatment regimen should be employed and include one or more agents or compositions of the present invention that inhibit *S. aureus* interaction with CXCR1, CXCR2, or DARC. A decreased or low-level of CXCR1, CXCR2, or DARC expression as compared to a normal control or reference population would indicate that the subject has a higher resistance to infection with *S. aureus*. A suitable treatment would still include one or more agents or compositions of the present invention to prevent or minimize infection. However, the dosing regimen is less aggressive than the dosing regimen in a subject more highly susceptible to infection.

Another aspect of the present invention is directed to an isolated Leukocidin E (LukE) antibody, or antibody binding fragment thereof, wherein said antibody or binding fragment thereof, binds an epitope corresponding to amino acid residue 182-196 of SEQ ID NO:4.

Another aspect of the present invention is directed to an isolated HlgA antibody, or antibody binding fragment thereof, wherein said antibody or binding fragment thereof, binds an epitope corresponding to amino acid residue 180-192 of SEQ ID NO:6.

For purposes of the present invention, the term "antibody" includes monoclonal antibodies, polyclonal antibodies, antibody fragments, genetically engineered forms of the antibodies, and combinations thereof. More specifically, the term "antibody," which is used interchangeably with the term "immunoglobulin," includes full length (i.e., naturally occurring or formed by normal immunoglobulin gene fragment recombinatorial processes) immunoglobulin molecules (e.g., an IgG antibody) and immunologically active fragments thereof (i.e., including the specific binding portion of the full-length immunoglobulin molecule), which again may be naturally occurring or synthetic in nature. Accordingly, the term "antibody fragment" includes a portion of an antibody such as $F(ab')_2$, $F(ab)_2$, Fab', Fab, Fv, scFv, sdAb (nanobody) and the like. Regardless of structure, an antibody fragment binds with the same antigen that is recognized by the full-length antibody, and, in the context of the present invention, specifically binds the CXCR1/CXCR2 or DARC receptor binding regions of LukE and HlgA. Methods of making and screening antibody fragments are well-known in the art.

In the present invention, the anti-LukE and anti-HlgA antibodies may have some degree of cross-reactivity with other Staphylococcus leukocidin S-subunits such as HlgC, LukS-PVL, LukS-I, LukA, and LukM. Therapeutically effective anti-LukE and/or anti-HlgA antibodies inhibit or reduce LukE and/or HlgA binding to CXCR1/CXCR2 or DARC binding. In some embodiments, the anti-LukE and/or anti-HlgA antibodies neutralize (e.g., substantially eliminate) LukE and HlgA activity, respectively.

Naturally occurring antibodies typically have two identical heavy chains and two identical light chains, with each light chain covalently linked to a heavy chain by an interchain disulfide bond and multiple disulfide bonds further link the two heavy chains to one another. Individual chains can fold into domains having similar sizes (110-125 amino acids) and structures, but different functions. The light chain can comprise one variable domain (VL) and/or one constant domain (CL). The heavy chain can also comprise one variable domain (VH) and/or, depending on the class or isotype of antibody, three or four constant domains (CH1, CH2, CH3 and CH4). In humans, the isotypes are IgA, IgD, IgE, IgG, and IgM, with IgA and IgG further subdivided into subclasses or subtypes (IgA1-2 and IgG1-4).

Generally, the variable domains show considerable amino acid sequence variability from one antibody to the next, particularly at the location of the antigen-binding site. Three regions, called hyper-variable or complementarity-determining regions (CDRs), are found in each of VL and VH, which are supported by less variable regions called framework variable regions. The inventive antibodies include IgG monoclonal antibodies as well as antibody fragments or engineered forms. These are, for example, Fv fragments, or proteins wherein the CDRs and/or variable domains of the exemplified antibodies are engineered as single-chain antigen-binding proteins.

The portion of an antibody consisting of the VL and VH domains is designated as an Fv (Fragment variable) and constitutes the antigen-binding site. A single chain Fv (scFv or SCA) is an antibody fragment containing a VL domain and a VH domain on one polypeptide chain, wherein the N terminus of one domain and the C terminus of the other domain are joined by a flexible linker. The peptide linkers used to produce the single chain antibodies are typically flexible peptides, selected to assure that the proper three-dimensional folding of the VL and VH domains occurs. The linker is generally 3 to 50 amino acid residues, and in some cases is shorter, e.g., about 3 to 30 amino acid residues, or 3 to 25 amino acid residues, or even 3 to 15 amino acid residues. An example of such linker peptides includes repeats of four glycine residues followed by a serine residue.

Single chain antibodies lack some or all of the constant domains of the whole antibodies from which they are derived. Therefore, they can overcome some of the problems associated with the use of whole antibodies. For example, single-chain antibodies tend to be free of certain undesired interactions between heavy-chain constant regions and other biological molecules. Additionally, single-chain antibodies are considerably smaller than whole antibodies and can have greater permeability than whole antibodies, allowing single-chain antibodies to localize and bind to target antigen-binding sites more efficiently. Furthermore, the relatively small size of single-chain antibodies makes them less likely to provoke an unwanted immune response in a recipient than whole antibodies.

Single-domain antibodies (sdAb; nanobody) are antibody fragments consisting of a single monomeric variable antibody domain (~12-15 kDa). The sdAb are derived from the variable domain of a heavy chain ($V_H$) or the variable domain of a light chain ($V_L$). sdAbs can be naturally produced, i.e., by immunization of dromedaries, camels, llamas, alpacas or sharks (Ghahroudi et al., "Selection and Identification of Single Domain Antibody Fragments from Camel Heavy-Chain Antibodies," FEBS Letters 414(3): 521-526 (1997), which is hereby incorporated by reference in its entirety). Alternatively, the antibody can be produced in microorganisms or derived from conventional whole antibodies (Harmsen et al., "Properties, Production, and Applications of Camelid Single-Domain Antibody Fragments," Appl. Microbiol. Biotechnology 77:13-22 (2007), Holt et al., "Domain Antibodies: Proteins for Therapy," Trends Biotech. 21(11): 484-490 (2003), which is hereby incorporated by reference in its entirety).

Fab (Fragment, antigen binding) refers to the fragments of the antibody consisting of the VL, CL, VH, and CH domains. Those generated following papain digestion simply are referred to as Fab and do not retain the heavy chain hinge region. Following pepsin digestion, various Fabs retaining the heavy chain hinge are generated. Those fragments with the interchain disulfide bonds intact are referred to as F(ab')2, while a single Fab' results when the disulfide bonds are not retained. $F(ab')_2$ fragments have higher avidity for antigen that the monovalent Fab fragments.

Fc (Fragment crystallization) is the designation for the portion or fragment of an antibody that comprises paired heavy chain constant domains. In an IgG antibody, for example, the Fc comprises CH2 and CH3 domains. The Fc of an IgA or an IgM antibody further comprises a CH4 domain. The Fc is associated with Fc receptor binding, activation of complement mediated cytotoxicity and antibody-dependent cellular-cytotoxicity (ADCC). For antibodies such as IgA and IgM, which are complexes of multiple IgG-like proteins, complex formation requires Fc constant domains.

Antibody "specificity" refers to selective recognition of the antibody for a particular epitope of an antigen. The term "epitope" includes any protein determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three dimensional structural characteristics, as well as specific charge characteristics. An epitope may be "linear" or "conformational". In a linear epitope, all of the points of interaction between the protein and the interacting molecule (such as an antibody) occur linearly along the primary amino acid sequence of the protein. In a conformational epitope, the points of interaction occur across amino acid residues on the protein that are separated from one another, i.e., noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation. Antibodies that recognize the same epitope can be verified in a simple immunoassay showing the ability of one antibody to block the binding of another antibody to a target antigen.

Monoclonal antibodies of the present invention may be murine, human, humanized or chimeric. A humanized antibody is a recombinant protein in which the CDRs of an antibody from one species; e.g., a rodent, rabbit, dog, goat, horse, or chicken antibody (or any other suitable animal antibody), are transferred into human heavy and light variable domains. The constant domains of the antibody molecule are derived from those of a human antibody. Methods for making humanized antibodies are well known in the art. Chimeric antibodies preferably have constant regions derived substantially or exclusively from human antibody constant regions and variable regions derived substantially or exclusively from the sequence of the variable region from a mammal other than a human. The chimerization process can be made more effective by also replacing the variable regions—other than the hyper-variable regions or the complementarity—determining regions (CDRs), of a murine (or other non-human mammalian) antibody with the corresponding human sequences. The variable regions other than the CDRs are also known as the variable framework regions (FRs). Yet other monoclonal antibodies of the present invention are bi-specific, in that they have specificity for two different epitopes. Bispecific antibodies are preferably human or humanized.

The above-described antibodies can be obtained in accordance with standard techniques. For example, LukE, HlgA, or an immunologically active fragment of LukE or HlgA containing the desired receptor binding epitopes can be administered to a subject, (e.g., a mammal such as a human or mouse, or in the case of nanobodies a dromedary, camel, llama, or shark). The leukocidins can be used by themselves as immunogens or they can be attached to a carrier protein or other carrier material, such as sepharose beads. After the animal has produced antibodies, a mixture of antibody producing cells, such as splenocytes, are isolated, from which polyclonal antibodies may be obtained. Monoclonal antibodies may be produced by isolating individual antibody-producing cells from the mixture and immortalizing them by, for example, fusing them with tumor cells, such as myeloma cells. The resulting hybridomas are preserved in culture and the monoclonal antibodies are harvested from the culture medium.

Another aspect of the present invention is directed to a composition comprising an isolated Leukocidin E (LukE) protein or polypeptide thereof having a non-functional CXCR1/CXCR2 binding domain and a pharmaceutically acceptable carrier.

As described herein, applicants have identified that the CXCR1/CXCR2 receptor binding region of LukE comprises amino acid residues 182-196 of the soluble LukE protein (SEQ ID NO:4). Accordingly, an isolated LukE protein having a non-functional CXCR1/CXCR2 binding domain contains one or more amino acid residue substitutions or deletions within this identified region (i.e., 182-196 of SEQ ID NO:4) that disrupt the receptor binding. In one embodiment of the present invention, the isolated LukE protein having a non-functional CXCR1/CXCR2 binding domain ("LukE$^{LukS\text{-}DR4}$") has an amino acid sequence of SEQ ID NO:8 as shown below.

```
Asn Thr Asn Ile Glu Asn Ile Gly Asp Gly Ala Glu Val
1               5                   10

Ile Lys Arg Thr Glu Asp Val Ser Ser Lys Lys Trp Gly
    15                  20                  25

Val Thr Gln Asn Val Gln Phe Asp Phe Val Lys Asp Lys
            30                  35

Lys Tyr Asn Lys Asp Ala Leu Ile Val Lys Met Gln Gly
40                  45                  50

Phe Ile Asn Ser Arg Thr Ser Phe Ser Asp Val Lys Gly
        55                  60                  65

Ser Gly Tyr Glu Leu Thr Lys Arg Met Ile Trp Pro Phe
                70                  75

Gln Tyr Asn Ile Gly Leu Thr Thr Lys Asp Pro Asn Val
    80                  85                  90

Ser Leu Ile Asn Tyr Leu Pro Lys Asn Lys Ile Glu Thr
            95                  100

Thr Asp Val Gly Gln Thr Leu Gly Tyr Asn Ile Gly Gly
105                 110                 115

Asn Phe Gln Ser Ala Pro Ser Ile Gly Gly Asn Gly Ser
        120                 125                 130

Phe Asn Tyr Ser Lys Thr Ile Ser Tyr Thr Gln Lys Ser
                135                 140

Tyr Val Ser Glu Val Asp Lys Gln Asn Ser Lys Ser Val
    145                 150                 155

Lys Trp Gly Val Lys Ala Asn Glu Phe Val Thr Pro Asp
            160                 165

Gly Lys Lys Ser Ala His Asp Arg Tyr Leu Phe Val Gly
170                 175                 180

Tyr Lys Pro Tyr Ser Gln Asn Pro Arg Asp Tyr Phe Val
        185                 190                 195

Pro Asp Asn Gln Leu Pro Pro Leu Val Gln Ser Gly Phe
                200                 205

Asn Pro Ser Phe Ile Thr Thr Leu Ser His Glu Lys Gly
    210                 215                 220

Ser Ser Asp Thr Ser Glu Phe Glu Ile Ser Tyr Gly Arg
            225                 230

Asn Leu Asp Ile Thr Tyr Ala Thr Leu Phe Pro Arg Thr
235                 240                 245

Gly Ile Tyr Ala Glu Arg Lys His Asn Ala Phe Val Asn
        250                 255                 260

Arg Asn Phe Val Val Arg Tyr Glu Val Asn Trp Lys Thr
            265                 270

His Glu Ile Lys Val Lys Gly His Asn
    275                 280
```

Suitable LukE polypeptides containing a non-functional CXCR1/CXCR2 receptor binding domain are about 50 to about 100 amino acids in length, more preferably between about 100-200 amino acids in length or between about 200-250 amino acids in length. An exemplary isolated LukE polypeptide comprises amino acid residues 1-273 of SEQ ID NO:4, amino acid residues 20-263 of SEQ ID NO:4, or amino acid residues 20-273 of SEQ ID NO:4, and contains one or more amino acid residues substitutions or deletions within the CXCR1/CXCR2 receptor binding region (i.e., amino acid residues 182-196). In one embodiment of the present invention, the isolated LukE polypeptide comprises the amino acid sequence of SEQ ID NO:9 as shown below.

```
Val Ser Ser Lys Lys Trp Gly Val Thr Gln Asn Val Gln
1               5                   10

Phe Asp Phe Val Lys Asp Lys Lys Tyr Asn Lys Asp Ala
            15              20                  25

Leu Ile Val Lys Met Gln Gly Phe Ile Asn Ser Arg Thr
                30                  35

Ser Phe Ser Asp Val Lys Gly Ser Gly Tyr Glu Leu Thr
40                  45                  50

Lys Arg Met Ile Trp Pro Phe Gln Tyr Asn Ile Gly Leu
                55              60                  65

Thr Thr Lys Asp Pro Asn Val Ser Leu Ile Asn Tyr Leu
                70                  75

Pro Lys Asn Lys Ile Glu Thr Thr Asp Val Gly Gln Thr
80                  85                  90

Leu Gly Tyr Asn Ile Gly Gly Asn Phe Gln Ser Ala Pro
                95              100

Ser Ile Gly Gly Asn Gly Ser Phe Asn Tyr Ser Lys Thr
105                 110                 115

Ile Ser Tyr Thr Gln Lys Ser Tyr Val Ser Glu Val Asp
                120                 125                 130

Lys Gln Asn Ser Lys Ser Val Lys Trp Gly Val Lys Ala
                135                 140

Asn Glu Phe Val Thr Pro Asp Gly Lys Lys Ser Ala His
                145                 150                 155

Asp Arg Tyr Leu Phe Val Gly Tyr Lys Pro Tyr Ser Gln
                160                 165

Asn Pro Arg Asp Tyr Phe Val Pro Asp Asn Gln Leu Pro
170                 175                 180

Pro Leu Val Gln Ser Gly Phe Asn Pro Ser Phe Ile Thr
                185                 190                 195

Thr Leu Ser His Glu Lys Gly Ser Ser Asp Thr Ser Glu
                200                 205

Phe Glu Ile Ser Tyr Gly Arg Asn Leu Asp Ile Thr Tyr
210                 215                 220

Ala Thr Leu Phe Pro Arg Thr Gly Ile Tyr Ala Glu Arg
                225                 230

Lys His Asn Ala Phe Val Asn Arg Asn
235                 240
```

In at least one embodiment, the LukE polypeptide containing a non-functional CXCR1/CXCR2 receptor binding domain has, for example, one or more substitutions or deletions of amino acid P184, G186, P187, G189, or any combination thereof (i.e., single mutants, double mutants, triple mutants, and quadruple mutants are all contemplated). Suitable examples include, without limitation, $LukE^{LkS-DR4}$ (i.e., SEQ ID NO:8), $LukE_{20-263}^{LukS-DR4}$ (i.e., SEQ ID NO:9), $LukE^{P184A,G186A,P187A}$ (i.e., SEQ ID NO:10, shown below), and $LukE^{P184A,G186A,P187A,G189A}$ (i.e., SEQ ID NO:11, shown below).

$LukE^{P184A,G186A,P187A}$

```
                                     SEQ ID NO: 10
Asn Thr Asn Ile Glu Asn Ile Gly Asp Gly Ala Glu Val
1               5                   10

Ile Lys Arg Thr Glu Asp Val Ser Ser Lys Lys Trp Gly
    15                  20                  25
```

-continued

```
Val Thr Gln Asn Val Gln Phe Asp Phe Val Lys Asp Lys
                30                  35

Lys Tyr Asn Lys Asp Ala Leu Ile Val Lys Met Gln Gly
40                  45                  50

Phe Ile Asn Ser Arg Thr Ser Phe Ser Asp Val Lys Gly
        55                  60                  65

Ser Gly Tyr Glu Leu Thr Lys Arg Met Ile Trp Pro Phe
                70                  75

Gln Tyr Asn Ile Gly Leu Thr Thr Lys Asp Pro Asn Val
    80                  85                  90

Ser Leu Ile Asn Tyr Leu Pro Lys Asn Lys Ile Glu Thr
            95                  100

Thr Asp Val Gly Gln Thr Leu Gly Tyr Asn Ile Gly Gly
105                 110                 115

Asn Phe Gln Ser Ala Pro Ser Ile Gly Gly Asn Gly Ser
        120                 125                 130

Phe Asn Tyr Ser Lys Thr Ile Ser Tyr Thr Gln Lys Ser
                135                 140

Tyr Val Ser Glu Val Asp Lys Gln Asn Ser Lys Ser Val
    145                 150                 155

Lys Trp Gly Val Lys Ala Asn Glu Phe Val Thr Pro Asp
            160                 165

Gly Lys Lys Ser Ala His Asp Arg Tyr Leu Phe Val Gln
170                 175                 180

Ser Ala Asn Ala Ala Thr Gly Ser Ala Arg Glu Tyr Phe
        185                 190                 195

Ala Pro Asp Asn Gln Leu Pro Pro Leu Val Gln Ser Gly
                200                 205

Phe Asn Pro Ser Phe Ile Thr Thr Leu Ser His Glu Lys
    210                 215                 220

Gly Ser Ser Asp Thr Ser Glu Phe Glu Ile Ser Tyr Gly
            225                 230

Arg Asn Leu Asp Ile Thr Tyr Ala Thr Leu Phe Pro Arg
235                 240                 245

Thr Gly Ile Tyr Ala Glu Arg Lys His Asn Ala Phe Val
        250                 255                 260

Asn Arg Asn Phe Val Val Arg Tyr Glu Val Asn Trp Lys
                265                 270

Thr His Glu Ile Lys Val Lys Gly His Asn;
    275                 280
```

$LukE^{P184A,G186A,P187A,G189A}$

```
                                     SEQ ID NO: 11
Asn Thr Asn Ile Glu Asn Ile Gly Asp Gly Ala Glu Val
1               5                   10

Ile Lys Arg Thr Glu Asp Val Ser Ser Lys Lys Trp Gly
    15                  20                  25

Val Thr Gln Asn Val Gln Phe Asp Phe Val Lys Asp Lys
                30                  35

Lys Tyr Asn Lys Asp Ala Leu Ile Val Lys Met Gln Gly
40                  45                  50

Phe Ile Asn Ser Arg Thr Ser Phe Ser Asp Val Lys Gly
        55                  60                  65

Ser Gly Tyr Glu Leu Thr Lys Arg Met Ile Trp Pro Phe
                70                  75
```

-continued

```
Gln Tyr Asn Ile Gly Leu Thr Thr Lys Asp Pro Asn Val
 80                  85                  90

Ser Leu Ile Asn Tyr Leu Pro Lys Asn Lys Ile Glu Thr
             95                 100

Thr Asp Val Gly Gln Thr Leu Gly Tyr Asn Ile Gly Gly
105                 110                 115

Asn Phe Gln Ser Ala Pro Ser Ile Gly Gly Asn Gly Ser
        120                 125                 130

Phe Asn Tyr Ser Lys Thr Ile Ser Tyr Thr Gln Lys Ser
            135                 140

Tyr Val Ser Glu Val Asp Lys Gln Asn Ser Lys Ser Val
145                 150                 155

Lys Trp Gly Val Lys Ala Asn Glu Phe Val Thr Pro Asp
                160                 165

Gly Lys Lys Ser Ala His Asp Arg Tyr Leu Phe Val Gln
170                 175                 180

Ser Ala Asn Ala Ala Thr Ala Ser Ala Arg Glu Tyr Phe
            185                 190                 195

Ala Pro Asp Asn Gln Leu Pro Pro Leu Val Gln Ser Gly
                200                 205

Phe Asn Pro Ser Phe Ile Thr Thr Leu Ser His Glu Lys
    210                 215                 220

Gly Ser Ser Asp Thr Ser Glu Phe Glu Ile Ser Tyr Gly
            225                 230

Arg Asn Leu Asp Ile Thr Tyr Ala Thr Leu Phe Pro Arg
235                 240                 245

Thr Gly Ile Tyr Ala Glu Arg Lys His Asn Ala Phe Val
            250                 255                 260

Asn Arg Asn Phe Val Val Arg Tyr Glu Val Asn Trp Lys
                265                 270

Thr His Glu Ile Lys Val Lys Gly His Asn;
    275                 280
```

```
Asn Glu Glu Phe Gln Val Gln Gln Thr Leu Gly Tyr Ser
    105                 110                 115

Tyr Gly Gly Asp Ile Asn Ile Ser Asn Gly Leu Ser Gly
            120                 125                 130

Gly Leu Asn Gly Ser Lys Ser Phe Ser Glu Thr Ile Asn
                135                 140

Tyr Lys Gln Glu Ser Tyr Arg Thr Thr Ile Asp Arg Lys
    145                 150                 155

Thr Asn His Lys Ser Ile Gly Trp Gly Val Glu Ala His
            160                 165

Lys Ile Met Asn Asn Gly Trp Gly Pro Tyr Gly Arg Asp
170                 175                 180

Ser Tyr Asp Pro Thr Tyr Gly Asn Glu Leu Phe Leu Gly
            185                 190                 195

Gly Arg Gln Ser Ser Ser Asn Ala Gly Gln Asn Phe Leu
                200                 205

Pro Thr His Gln Met Pro Leu Leu Ala Arg Gly Asn Phe
    210                 215                 220

Asn Pro Glu Phe Ile Ser Val Leu Ser His Lys Gln Asn
            225                 230

Asp Thr Lys Lys Ser Lys Ile Lys Val Thr Tyr Gln Arg
235                 240                 245

Glu Met Asp Arg Tyr Thr Asn Gln Trp Asn Arg Leu His
            250                 255                 260

Trp Val Gly Asn Asn Tyr Lys Asn Gln Asn Thr Val Thr
                265                 270

Phe Thr Ser Thr Tyr Glu Val Asp Trp Gln Asn His Thr
    275                 280                 285

Val Lys Leu Ile Gly Thr Asp Ser Lys Glu Thr Asn Pro
            290                 295

Gly Val
300
```

The composition of the present invention may further comprise an isolated Leukocidin (LukD) protein or polypeptide thereof. The isolated LukD protein may comprise the amino acid sequence of SEQ ID NO:12 as shown below or an amino acid sequence having at least 70% sequence similarity to SEQ ID NO:12 (amino acid sequence of LukD).

```
Ala Gln His Ile Thr Pro Val Ser Glu Lys Lys Val Asp
1               5                  10

Asp Lys Ile Thr Leu Tyr Lys Thr Thr Ala Thr Ser Asp
    15                  20                  25

Asn Asp Lys Leu Asn Ile Ser Gln Ile Leu Thr Phe Asn
            30                  35

Phe Ile Lys Asp Lys Ser Tyr Asp Lys Asp Thr Leu Val
40                  45                  50

Leu Lys Ala Ala Gly Asn Ile Asn Ser Gly Tyr Lys Lys
        55                  60                  65

Pro Asn Pro Lys Asp Tyr Asn Tyr Ser Gln Phe Tyr Trp
            70                  75

Gly Gly Lys Tyr Asn Val Ser Val Ser Ser Glu Ser Asn
80                  85                  90

Asp Ala Val Asn Val Val Asp Tyr Ala Pro Lys Asn Gln
        95                  100
```

Suitable LukD polypeptides are about 50 to about 100 amino acids in length, more preferably between about 100-200 amino acids in length or between about 200-250 amino acids in length. An exemplary isolated LukD polypeptide comprises amino acid residues 1-286 of SEQ ID NO:12, amino acid residues 20-281 of SEQ ID NO:12, or amino acid residues 20-286 of SEQ ID NO:12. Suitable LukD polypeptides also include those polypeptide comprising an amino acid sequence having about 70-80% sequence similarity, preferably 80-90% sequence similarity, more preferably 90-95% sequence similarity, and most preferably 95-99% sequence similarity to amino acid residues 1-286 of SEQ ID NO:12, amino acid residues 20-281 of SEQ ID NO:11, or amino acid residues 20-286 of SEQ ID NO:12.

Another aspect of the present invention is directed to a composition comprising an isolated HlgA protein or polypeptide thereof having a non-functional CXCR1/CXCR2 binding domain and a pharmaceutically acceptable carrier.

As described herein, applicants have identified that the CXCR1/CXCR2 receptor binding region of HlgA comprises amino acid residues 180-192 of the soluble HlgA protein (SEQ ID NO:6). Accordingly, an isolated HlgA protein having a non-functional CXCR1/CXCR2 binding domain contains one or more amino acid residue substitutions or deletions within this identified region (i.e., 180-192 of SEQ ID NO:6) that disrupt the receptor binding. In one embodiment of the present invention, the isolated HlgA protein having a non-functional CXCR1/CXCR2 binding domain ("HlgA$^{LukS-DR4}$") has an amino acid sequence of SEQ ID NO:13 as shown below

```
Glu Asn Lys Ile Glu Asp Ile Gly Gln Gly Ala Glu Ile
1               5                   10
Ile Lys Arg Thr Gln Asp Ile Thr Ser Lys Arg Leu Ala
        15              20                  25
Ile Thr Gln Asn Ile Gln Phe Asp Phe Val Lys Asp Lys
            30                  35
Lys Tyr Asn Lys Asp Ala Leu Val Val Lys Met Gln Gly
40                  45                  50
Phe Ile Ser Ser Arg Thr Thr Tyr Ser Asp Leu Lys Lys
        55                  60                  65
Tyr Pro Tyr Ile Lys Arg Met Ile Trp Pro Phe Gln Tyr
                70                  75
Asn Ile Ser Leu Lys Thr Lys Asp Ser Asn Val Asp Leu
    80                  85                  90
Ile Asn Tyr Leu Pro Lys Asn Lys Ile Asp Ser Ala Asp
            95                  100
Val Ser Gln Lys Leu Gly Tyr Asn Ile Gly Gly Asn Phe
105                 110                 115
Gln Ser Ala Pro Ser Ile Gly Gly Ser Gly Ser Phe Asn
        120                 125                 130
Tyr Ser Lys Thr Ile Ser Tyr Asn Gln Lys Asn Tyr Val
            135                 140
Thr Glu Val Glu Ser Gln Asn Ser Lys Gly Val Lys Trp
    145                 150                 155
Gly Val Lys Ala Asn Ser Phe Val Thr Pro Asn Gly Gln
        160                 165
Val Ser Ala Tyr Asp Gln Tyr Leu Phe Ala Gly Tyr Lys
170                 175                 180
Pro Tyr Ser Gln Asn Pro Arg Asp Tyr Phe Val Pro Asp
        185                 190                 195
Asn Gln Leu Pro Pro Leu Ile Gln Ser Gly Phe Asn Pro
                200                 205
Ser Phe Ile Thr Thr Leu Ser His Glu Arg Gly Lys Gly
    210                 215                 220
Asp Lys Ser Glu Phe Glu Ile Thr Tyr Gly Arg Asn Met
            225                 230
Asp Ala Thr Tyr Ala Tyr Val Thr Arg His Arg Leu Ala
235                 240                 245
Val Asp Arg Lys His Asp Ala Phe Lys Asn Arg Asn Val
        250                 255                 260
Thr Val Lys Tyr Glu Val Asn Trp Lys Thr His Glu Val
            265                 270
Lys Ile Lys Ser Ile Thr Pro Lys
    275                 280
```

Suitable HlgA polypeptides containing a non-functional CXCR1/CXCR2 receptor binding domain are about 50 to about 100 amino acids in length, more preferably between about 100-200 amino acids in length or between about 200-250 amino acids in length. An exemplary isolated HlgA polypeptide comprises amino acid residues 1-268 of SEQ ID NO:6, amino acid residues 20-258 of SEQ ID NO:6, or amino acid residues 20-268 of SEQ ID NO:6, and contains one or more amino acid residues substitutions or deletions within the CXCR1/CXCR2 receptor binding region (i.e., amino acid residues 180-192). In one embodiment of the present invention, the isolated HlgA polypeptide comprises the amino acid sequence of SEQ ID NO:14 as shown below.

```
Ile Thr Ser Lys Arg Leu Ala Ile Thr Gln Asn Ile Gln
1               5                   10
Phe Asp Phe Val Lys Asp Lys Lys Tyr Asn Lys Asp Ala
        15              20                  25
Leu Val Val Lys Met Gln Gly Phe Ile Ser Ser Arg Thr
            30                  35
Thr Tyr Ser Asp Leu Lys Lys Tyr Pro Tyr Ile Lys Arg
40                  45                  50
Met Ile Trp Pro Phe Gln Tyr Asn Ile Ser Leu Lys Thr
        55                  60                  65
Lys Asp Ser Asn Val Asp Leu Ile Asn Tyr Leu Pro Lys
                70                  75
Asn Lys Ile Asp Ser Ala Asp Val Ser Gln Lys Leu Gly
    80                  85                  90
Tyr Asn Ile Gly Gly Asn Phe Gln Ser Ala Pro Ser Ile
            95                  100
Gly Gly Ser Gly Ser Phe Asn Tyr Ser Lys Thr Ile Ser
105                 110                 115
Tyr Asn Gln Lys Asn Tyr Val Thr Glu Val Glu Ser Gln
        120                 125                 130
Asn Ser Lys Gly Val Lys Trp Gly Val Lys Ala Asn Ser
            135                 140
Phe Val Thr Pro Asn Gly Gln Val Ser Ala Tyr Asp Gln
    145                 150                 155
Tyr Leu Phe Ala Gly Tyr Lys Pro Tyr Ser Gln Asn Pro
        160                 165
Arg Asp Tyr Phe Val Pro Asp Asn Gln Leu Pro Pro Leu
170                 175                 180
Ile Gln Ser Gly Phe Asn Pro Ser Phe Ile Thr Thr Leu
        185                 190                 195
Ser His Glu Arg Gly Lys Gly Asp Lys Ser Glu Phe Glu
                200                 205
Ile Thr Tyr Gly Arg Asn Met Asp Ala Thr Tyr Ala Tyr
    210                 215                 220
Val Thr Arg His Arg Leu Ala Val Asp Arg Lys His Asp
            225                 230
Ala Phe Lys Asn Arg Asn
235                 240
```

In at least one embodiment, the HlgA polypeptide containing a non-functional CXCR1/CXCR2 receptor binding domain has, for example, one or more substitutions or deletions of amino acid P182, G184, P185, or any combination thereof (i.e., single mutants, double mutants, and triple mutants are all contemplated). Suitable examples include, without limitation, HlgA$^{LukS-DR4}$ (i.e., SEQ ID NO:13), HlgA$_{20-258}^{LukS-DR4}$ (i.e., SEQ ID NO:14), and HlgA$^{P182A,G184A,P185A}$ (i.e., SEQ ID NO:15, shown below).

```
Glu Asn Lys Ile Glu Asp Ile Gly Gln Gly Ala Glu Ile
1               5                   10
Ile Lys Arg Thr Gln Asp Ile Thr Ser Lys Arg Leu Ala
        15              20                  25
```

-continued

```
Ile Thr Gln Asn Ile Gln Phe Asp Val Lys Asp Lys
            30                  35
Lys Tyr Asn Lys Asp Ala Leu Val Val Lys Met Gln Gly
40                  45                  50
Phe Ile Ser Ser Arg Thr Thr Tyr Ser Asp Leu Lys Lys
            55                  60                  65
Tyr Pro Tyr Ile Lys Arg Met Ile Trp Pro Phe Gln Tyr
                70                  75
Asn Ile Ser Leu Lys Thr Lys Asp Ser Asn Val Asp Leu
    80                  85                  90
Ile Asn Tyr Leu Pro Lys Asn Lys Ile Asp Ser Ala Asp
                95                  100
Val Ser Gln Lys Leu Gly Tyr Asn Ile Gly Gly Asn Phe
105                 110                 115
Gln Ser Ala Pro Ser Ile Gly Gly Ser Gly Ser Phe Asn
            120                 125                 130
Tyr Ser Lys Thr Ile Ser Tyr Asn Gln Lys Asn Tyr Val
                135                 140
Thr Glu Val Glu Ser Gln Asn Ser Lys Gly Val Lys Trp
145                 150                 155
Gly Val Lys Ala Asn Ser Phe Val Thr Pro Asn Gly Gln
            160                 165
Val Ser Ala Tyr Asp Gln Tyr Leu Phe Ala Gln Asp Ala
170                 175                 180
Thr Ala Ala Ala Arg Asp Tyr Phe Val Pro Asp Asn
            185                 190                 195
Gln Leu Pro Pro Leu Ile Gln Ser Gly Phe Asn Pro Ser
                200                 205
Phe Ile Thr Thr Leu Ser His Glu Arg Gly Lys Gly Asp
210                 215                 220
Lys Ser Glu Phe Glu Ile Thr Tyr Gly Arg Asn Met Asp
            225                 230
Ala Thr Tyr Ala Tyr Val Thr Arg His Arg Leu Ala Val
235                 240                 245
Asp Arg Lys His Asp Ala Phe Lys Asn Arg Asn Val Thr
            250                 255                 260
Val Lys Tyr Glu Val Asn Trp Lys Thr His Glu Val Lys
                265                 270
Ile Lys Ser Ile Thr Pro Lys
            275         280
```

The composition of the present invention may further comprise an isolated HlgB protein or polypeptide thereof. The isolated HlgB protein may comprise the amino acid sequence of SEQ ID NO:16 as shown below or an amino acid sequence having at least 70% sequence similarity to SEQ ID NO:16 (amino acid sequence of HlgB).

```
Glu Gly Lys Ile Thr Pro Val Ser Val Lys Lys Val Asp
1               5                   10
Asp Lys Val Thr Leu Tyr Lys Thr Thr Ala Thr Ala Asp
    15                  20                  25
Ser Asp Lys Phe Lys Ile Ser Gln Ile Leu Thr Phe Asn
            30                  35
Phe Ile Lys Asp Lys Ser Tyr Asp Lys Asp Thr Leu Val
40                  45                  50
Leu Lys Ala Thr Gly Asn Ile Asn Ser Gly Phe Val Lys
            55                  60                  65
Pro Asn Pro Asn Asp Tyr Asp Phe Ser Lys Leu Tyr Trp
                70                  75
Gly Ala Lys Tyr Asn Val Ser Ile Ser Ser Gln Ser Asn
80                  85                  90
Asp Ser Val Asn Val Val Asp Tyr Ala Pro Lys Asn Gln
            95                  100
Asn Glu Glu Phe Gln Val Gln Asn Thr Leu Gly Tyr Thr
105                 110                 115
Phe Gly Gly Asp Ile Ser Ile Ser Asn Gly Leu Ser Gly
            120                 125                 130
Gly Leu Asn Gly Asn Thr Ala Phe Ser Glu Thr Ile Asn
                135                 140
Tyr Lys Gln Glu Ser Tyr Arg Thr Thr Leu Ser Arg Asn
            145                 150                 155
Thr Asn Tyr Lys Asn Val Gly Trp Gly Val Glu Ala His
                160                 165
Lys Ile Met Asn Asn Gly Trp Gly Pro Tyr Gly Arg Asp
170                 175                 180
Ser Phe His Pro Thr Tyr Gly Asn Glu Leu Phe Leu Ala
            185                 190                 195
Gly Arg Gln Ser Ser Ala Tyr Ala Gly Gln Asn Phe Ile
                200                 205
Ala Gln His Gln Met Pro Leu Leu Ser Arg Ser Asn Phe
    210                 215                 220
Asn Pro Glu Phe Leu Ser Val Leu Ser His Arg Gln Asp
                225                 230
Gly Ala Lys Lys Ser Lys Ile Thr Val Thr Tyr Gln Arg
235                 240                 245
Glu Met Asp Leu Tyr Gln Ile Arg Trp Asn Gly Phe Tyr
            250                 255                 260
Trp Ala Gly Ala Asn Tyr Lys Asn Phe Lys Thr Arg Thr
                265                 270
Phe Lys Ser Thr Tyr Glu Ile Asp Trp Glu Asn His Lys
    275                 280                 285
Val Lys Leu Leu Asp Thr Lys Glu Thr Glu Asn Asn Lys
            290                 295
```

Suitable HlgB polypeptides are about 50 to about 100 amino acids in length, more preferably between about 100-200 amino acids in length or between about 200-250 amino acids in length. Suitable HlgB polypeptides also include those polypeptide comprising an amino acid sequence having about 70-80% sequence similarity, preferably 80-90% sequence similarity, more preferably 90-95% sequence similarity, and most preferably 95-99% sequence similarity to amino acid residues 1-286 of SEQ ID NO:16.

Another aspect of the present invention is directed to a method of preventing or treating Human Immunodeficiency Virus (HIV) infection in a subject. This method involves selecting a subject at risk of having or having HIV infection and administering, to the selected subject, a composition of the present invention comprising an isolated LukE protein or polypeptide thereof having a non-functional CXCR1/CXCR2 binding domain under conditions effective to prevent or treat HIV in the subject. The composition may further contain an isolated LukD protein or polypeptide thereof as described above. The composition may also contain any one or more substitutions or deletions to the LukE protein or polypeptide at amino acids P184, G186, P187, and/or G189 exist, as described above.

As described herein and elsewhere (see U.S. Patent Application Publication No. 20130039885 to Torres et al., which is hereby incorporated by reference in its entirety), CCR5 is also a cellular receptor for *S. aureus* LukE toxin. Binding of LukED to CCR5 positive cells causes pore formation and results in cell death. The CCR5 receptor is known to mediate HIV cell entry and infectivity; therefore, treating a subject having HIV with a composition comprising LukE and LukD proteins or polypeptides will cause cell death of all HIV positive cells. This method of treatment is superior to current HIV therapeutic strategies because LukED treatment will selectively and specifically deplete all CCR5 positive, and therefore, all HIV positive cells in a subject. The composition of the present invention comprising a "modified LukE protein or polypeptide", i.e., a LukE protein or polypeptide having a non-functional CXCR1/CXCR2 receptor binding domain, has enhanced specificity for treating HIV and other indications described herein, because non-specific targeting and cell death of CXCR1/CXCR2 positive cells, including PMNs is avoided, i.e., compositions comprising the modified LukE protein or polypeptide of the present invention are highly selective for CCR5$^+$ cells.

The therapeutic compositions of the present invention can be administered as part of a combination therapy in conjunction with another anti-HIV agent. Accordingly, the composition comprising an isolated LukE protein, or polypeptide thereof having a non-functional CXCR1/CXCR2 binding domain, and an isolated LukD protein, or polypeptide thereof may further comprise or be administered in combination with one or more antiviral or other agents useful in the treatment of HIV. Suitable antiviral agents include nucleoside reverse transcriptase inhibitors, non-nucleoside reverse transcriptase inhibitors and protease inhibitors. More specifically, suitable antiviral agents include, without limitation, zidovudine, lamivudine, zalcitabine, didanosine, stavudine, abacavir, adefovir dipivoxil, lobucavir, BC H-10652, emitricitabine, beta-L-FD4, DAPD, lodenosine, nevirapine, delaviridine, efavirenz, PNU-142721, AG-1549, MKC-442, (+)-calanolide A and B, saquinavir, indinavir, ritonavir, nelfinavir, lasinavir, DMP-450, BMS-2322623, ABT-378, amprenavir, hydroxyurea, ribavirin, IL-2, IL-12, pentafuside, Yissum No. 1 1607 and AG-1549.

For purposes of this aspect of the invention, the target "subject" encompasses any animal, preferably a mammal, more preferably a human. In the context of administering a composition of the invention for purposes of preventing HIV infection in a subject, the target subject encompasses any subject that is at risk of being infected by HIV. In the context of administering a composition of the invention for purposes of treating HIV infection in a subject, the target subject encompasses any subject infected with HIV.

In the context of using therapeutic compositions of the present invention to treat an HIV infection, a therapeutically effective amount of modified LukE and LukD is that amount capable of achieving a reduction in symptoms associated with infection, a decrease in the severity of at least one symptom, a decrease in the viral load of the subject, and preferably a complete eradication of the virus from the subject.

Therapeutically effective amounts of a composition containing the modified LukE and LukD can be determined in accordance with standard procedures, which take numerous factors into account, including, for example, the concentrations of these active agents in the composition, the mode and frequency of administration, the severity of the HIV infection to be treated (or prevented), and subject details, such as age, weight and overall health and immune condition. General guidance can be found, for example, in the publications of the International Conference on Harmonization and in REMINGTON'S PHARMACEUTICAL SCIENCES (Mack Publishing Company 1990), which is hereby incorporated by reference in its entirety. A clinician may administer a composition containing the modified LukE and LukD proteins or polypeptides, until a dosage is reached that provides the desired or required prophylactic or therapeutic effect. The progress of this therapy can be easily monitored by conventional assays (e.g., viral load).

Therapeutic compositions of the present invention may be administered in a single dose, or in accordance with a multi-dosing protocol. For example, in a multi-dosing protocol, the therapeutic composition may be administered once or twice daily, weekly, or monthly depending on the use and severity of the condition being treated. Different dosages, timing of dosages, and relative amounts of the therapeutic composition can be selected and adjusted by one of ordinary skill in the art. Modes of administration of the therapeutic compositions of the present invention are described infra.

Another aspect of the present invention relates to a method of preventing HIV infection of a subject. This method involves providing a composition comprising an isolated LukE protein or polypeptide having a non-functional CXCR1/CXCR2 receptor binding domain, and, optionally, an isolated LukD protein or polypeptide, and contacting tissue of the subject with the composition under conditions effective to block HIV infectivity of cells in the tissue, thereby inhibiting HIV infection of the subject.

In accordance with this aspect of the invention, the composition comprising the modified LukE and LukD proteins or polypeptides serves as an anti-HIV microbicide, selectively killing only CCR5$^+$ cells that are susceptible to HIV infection before infection occurs without non-specifically targeting CXCR1/CXCR2$^+$ cells. The composition can be administered to any female or a male subject that is at risk for exposure to HIV as a prophylactic means of preventing HIV infection.

In accordance with this aspect of the invention, the composition comprising the modified LukE and LukD proteins or polypeptides may further comprise one or more one or more additional agents. The one or more additional agents include, for example, and without limitation, a lubricant, an anti-microbial agent, an antioxidant, a humectant, an emulsifier, a spermicidal agent, or a mixture of two or more thereof.

Suitable lubricants include, without limitation, cetyl esters wax, hydrogenated vegetable oil, magnesium stearate, methyl stearate, mineral oil, polyoxyethylene-polyoxypropylene copolymer, polyethylene glycol, polyvinyl alcohol, sodium lauryl sulfate or white wax, or a mixture of two or more thereof. Suitable antimicrobial agents include, without limitation, propylene glycol, methyl paraben or propyl paraben, or a mixture of two or more thereof. Suitable antioxidants include, without limitation, butylated hydroxyanisole, butylated hydroxytoluene, or edetate disodium, or a mixture of two or more thereof. Suitable humectants include, without limitation, ethylene glycol, glycerin, or sorbitol, or a mixture of two or more thereof. Suitable emulsifiers include, without limitation, carbomer, polyoxyethylene-10-stearyl ether, polyoxyethylene-20-stearyl ether, cetostearyl alcohol, cetyl alcohol, cholesterol, diglycol stearate, glyceryl monostearate, glyceryl stearate, hydroxypropyl cellulose, hydroxypropylmethyl cellulose, lanolin, polyoxyethylene lauryl ether, methyl cellulose, polyoxyethylene stearate, polysorbate, propylene glycol monostearate, sorbitan esters or stearic acid, or a mixture of two or more thereof.

In one embodiment of this aspect of the invention, the microbicide composition is formulated for topical application. Compositions for topical administration according to the present invention can be formulated as solutions, ointments, creams, foams, suspensions, lotions, powders, pastes, gels, sprays, aerosols, or oils for vaginal, anal, or buccal administration. In another embodiment of the invention, the composition is formulated for vaginal and/or rectal administration. In another embodiment of the invention, the composition is formulated for slow release from a vaginal device, such as a vaginal ring, an IUD, or a sponge, or other contraceptive device (e.g., condom). In yet another embodiment of the present invention, the composition is formulated for application as an oral rinse. In a preferred embodiment of the invention, the composition is applied or contacted directly with the skin or a mucous membrane of the subject that is at risk of being exposed to HIV infection.

Another aspect of the invention relates to a method of treating an inflammatory condition in a subject. This method involves selecting a subject having an inflammatory condition and administering a composition of the present invention comprising an isolated LukE protein or polypeptide having a non-functional CXCR1/CXCR2 receptor binding domain, and, optionally, an isolated LukD protein or polypeptide, in an amount effective to treat the inflammatory condition in the subject.

Applicants have discovered that LukED targets and kills human CCR5-positive leukocytes. Compositions comprising a LukE protein or polypeptide having a non-functional CXCR1/CXCR2 receptor binding domain selectively and specifically direct LukED mediated cytotoxicity to $CCR5^+$ cells but not other nucleated mammalian cells. Since CCR5 is expressed in a subset of effector T cells that produce proinflammatory cytokines that are enriched locally during inflammation, compositions of the present invention comprising the modified LukE and LukD proteins and polypeptides are useful in treating inflammatory conditions by selectively depleting the CCR5 positive cell populations. Any subject, preferably a mammal, more preferably a human, can be treated in accordance with this aspect of the invention, regardless of the cause of the inflammation, e.g., any bacterial or viral infection. Suitable compositions containing the modified LukE and LukD proteins and/or polypeptides are described supra.

The therapeutic compositions of the present invention may be used to treat a number of inflammatory conditions, including but not limited to acute inflammatory conditions, rheumatoid arthritis, Crohn's disease, atherosclerosis, psoriasis, ulcerative colitis, psoriatic arthritis, multiple sclerosis, lupus, type I diabetes, primary biliary cirrhosis, inflammatory bowel disease, tuberculosis, skin wounds and infections, tissue abscesses, folliculitis, osteomyelitis, pneumonia, scalded skin syndrome, septicemia, septic arthritis, myocarditis, endocarditis, toxic shock syndrome, allergic contact dermatitis, acute hypersensitivity, and acute neurological inflammatory injury (e.g., caused by acute infection).

Acute inflammatory conditions encompass the initial response of the body to invading stimuli, and involve the recruitment of plasma and white blood cells (leukocytes) to the localized area of the injured or infected tissues. Acute inflammatory conditions have a rapid onset and severe symptoms. The duration of the onset, from a normal condition of the patient to one in which symptoms of inflammation are seriously manifested, generally lasts up to about 72 hours. Acute inflammatory conditions that are amenable to treatment with the therapeutic compositions of the present invention include conjunctivitis, iritis, uveitis, central retinitis, external otitis, acute suppurative otitis media, mastoiditis, labyrinthitis, chronic rhinitis, acute rhinitis, sinusitis, pharyngitis, tonsillitis, contact dermatitis, dermonecrosis, diabetic polyneuritis, polymyositis, myositis ossificans, degenerative arthritis, rheumatoid arthritis, periarthritis scapulohumeralis, and osteitis deformans. In one embodiment of the present invention, the acute inflammatory condition is an infected wound in the skin or soft tissue.

In the context of treatment of an inflammatory condition, an effective amount of a modified LukE/LukD composition is the amount that is therapeutically effective in the sense that treatment is capable of achieving a reduction in the inflammation, a decrease in the severity of the inflammation, or even a total alleviation of the inflammatory condition.

The anti-inflammatory compositions of the present invention may be administered by any route of administration as described infra. In the case of treatment of acute inflammatory conditions that are localized, non-systemic administration may be preferred in which case the administration of the therapeutic composition is at or around the site of the acute inflammation. In this regard, compositions for topical administration are preferred. In addition to the topical formulations described supra, the topical formulation can also be in the form of patches or dressings impregnated with active ingredient(s), which can optionally comprise one or more excipients or diluents. In some embodiments, the topical formulation includes a material that enhances absorption or penetration of the active agent(s) through the skin or other affected areas.

A therapeutically effective amount of a modified LukE/LukD composition in accordance with this and other aspects of the invention is the amount necessary to obtain beneficial or desired results. A therapeutically effective amount can be administered in one or more administrations, applications or dosages and is not intended to be limited to a particular formulation or administration route.

Also in accordance with this aspect of the invention, the modified LukE/LukD composition can be administered in combination with (i.e., prior to, in conjunction with, or subsequent to, other anti-inflammatory compositions, a TNF$\alpha$ inhibitor, or a combination thereof. Exemplary anti-inflammatory medications include, but are not limited to, non-steroidal anti-inflammatory drugs (NSAID), analgesics, glucocorticoids, disease-modifying anti-rheumatic drugs, dihydrofolate reductase inhibitors (e.g., methotrexate), biologic response modifiers, and any combination thereof.

A suitable NSAID is a selective cyclooxygenase-2 (COX-2) inhibitor. Exemplary COX-2 inhibitors include, without limitation, nimesulide, 4-hydroxynimesulide, flosulide, meloxicam, celecoxib, and Rofecoxib (Vioxx). Alternatively, a non-selective NSAID inhibitor is administered in combination with the LukE/D composition of the present invention. Exemplary non-selective NSAIDS inhibitors include, without limitation, diclofenac, diflunisal, etodolac, fenoprofen, flurbiprofen, ibuprofen, indomethacin, ketoprofen, ketorolac, mefenamic acid, meloxicam, nabumetone, naproxen, oxaprozin, piroxicam, salsalate, sulindac and tolmetin.

Preferred analgesics include, without limitation, acetaminophen, oxycodone, tramadol, and propoxyphene hydrochloride.

Preferred glucocorticoids include, without limitation, cortisone, dexamethosone, hydrocortisone, methylpredisolone, prednisolone, and prednisone.

Preferred biological response modifiers include a B-cell inhibitor, such as Rituximab, or a T cell activation inhibitor, such as, Leflunomide, Etanercept (Enbrel), or Infliximab (Remicade).

Suitable TNFα inhibitors include a TNF-α antibody, a matrix metalloproteinase inhibitor, a corticosteroid, a tetracycline TNFα antagonist, a fluoroquinolone TNFα antagonist, and a quinolone TNFα antagonist. Exemplary TNFα antagonist antibodies include, without limitation, infliximab, etanercept, CytoFAb, AGT-1, afelimomab, PassTNF, and CDP-870. Exemplary corticosteroids include, without limitation, mometasone, fluticasone, ciclesonide, budesonide, beclomethasone, beconase, flunisolide, deflazacort, betamethasone, methyl-prednisolone, dexamethasone, prednisolone, hydrocortisone, cortisol, triamcinolone, cortisone, corticosterone, dihydroxycortisone, beclomethasone dipropionate, and prednisone. Exemplary tetracycline TNF-α antagonists include, without limitation, doxycycline, minocycline, oxytetracycline, tetracycline, lymecycline, and 4-hydroxy-4-dimethylaminotetracycline.

Another aspect of the present invention relates to a method of preventing graft-versus-host-disease (GVHD) in a subject. This method involves selecting a subject having or at risk of having GVHD, and administering a composition comprising an isolated LukE protein or polypeptide having a non-functional CXCR1/CXCR2 receptor binding domain and, optionally, an isolated LukD protein or polypeptide, in an amount effective to prevent graft-versus-host-disease (GVHD) in the subject.

Graft-versus-host disease (GVHD) remains the primary complication of clinical bone marrow transplantation (BMT) and a major impediment to widespread application of this important therapeutic modality. The hallmark of GVHD is infiltration of donor T lymphocytes into host epithelial compartments of the skin, intestine, and biliary tract. GVHD occurs when mature T cells, contained in the bone marrow of the graft, are transplanted into immunosuppressed hosts. After transplantation, host antigen presenting cells (APCs) activate T cells of the graft (donor T cells) by presenting host histocompatibility antigens to the graft T-cells. Donor-derived APCs may also activate donor T cells by cross-presenting host alloantigens. The newly generated host-specific T effector (hsTeff) populations then migrate to peripheral host organs and effect target organ damage GVHD generally occurs in an acute and chronic form. Acute GVHD will be observed within about the first 100 days post BMT, whereas chronic GVHD occurs after this initial 100 days. In addition to chronology, different clinical symptoms are also manifest in acute GVHD versus chronic GVHD. Acute GVHD is generally characterized by damage to host liver, skin, mucosa and intestinal epithelium in the host subject, although some forms of idiopathic pneumonia have also been reported. Chronic GVHD is, on the other hand, associated with damage to connective tissue as well as the organs and tissues damaged during acute GVHD in the host subject. In general, the methods of the present invention relate to therapies for either addressing GVHD that is already present in a host subject or preventing GVHD from arising in a host subject. In one embodiment, the present invention relates to methods of treating or preventing acute GVHD. In particular, the methods of the present invention are suitable for treating acute GVHD where the GVHD is damaging host intestinal epithelium. The methods of the present invention are also suitable for treating acute GVHD where the GVHD is damaging at least one tissue selected from the group consisting of the host liver, the host skin, the host lung and the host mucosa. Of course, the methods may be used to treat acute GVHD where the GVHD is damaging more than one tissue.

In accordance with this embodiment of the invention, CCR5-positive donor T cells transplanted into the recipient host during allogenic transplantation mediate GVHD. Accordingly, in one embodiment of the present invention, donor bone marrow cells are treated with a composition containing the modified LukE/Luke D prior to transplantation to effectuate cell death of all $CCR5^+$ cells, thereby preventing GVDH.

In another embodiment of the present invention, treatment of the donor bone marrow cells is achieved by treating the graft. "Treating the graft" is intended to mean administering a composition or performing a procedure to the graft material, where the treatment is not intended to directly affect the host organism. Of course, successful treatment of the graft will indirectly affect the host organism in that the severity of GVHD may be reduced, or even removed entirely. The methods of the invention are not limited to the location of the graft at the time the graft is treated. Thus, in one embodiment, the graft is treated prior to removal from the donor organism. In another embodiment, the graft is treated after removal from the donor organism. In yet another embodiment, the graft is treated after removal from the donor organism, but prior to transplantation into the host subject. In still another embodiment, the graft is treated after transplantation into the host organism.

In accordance with this aspect of the invention, the composition comprising modified LukE and LukD may be administered as part of a combination therapy. For example, the LukE/LukD composition may be co-administered with another pharmaceutically active substance, such as but not limited to, methotrexate and cyclosporine. Additional agents that may be co-administered include but are not limited to, antibodies directed to various targets, tacrolimus, sirolimus, interferons, opioids, TNFα (tumor necrosis factor-α), binding proteins, Mycophenolate mofetil and other inhibitors of inosine monophosphate dehydrogenase (IPDH), glucocorticoids, azathioprine and other cytostatic agents such as, but not limited to, antimetabolites and alkylating agents. In one embodiment, the graft or donor may be pretreated by administration of immunosuppressive drugs such as cyclosporine (alone or in combination with steroids) and methotrexate prior to transplantation. For prevention, immunosuppressive therapy typically consists of combined regimens of methotrexate (MTX), cyclosporin (CsA), tacrolimus (FK 506), and/or a corticosteriod. Intravenous gamma-globulin preparations administered prophylactically have also been shown to be beneficial for the prevention of GVHD. In addition, pentoxyfylline, a xanthine derivative capable of down-regulating TNFα production, may be administered with cyclosporin plus either methotrexate or methylprednisolone to further decrease incidence of GVHD. Chronic GVHD may be treated with steroids such as prednisone, ozothioprine and cyclosporine. Also, antithymocyte globulin (ATG) and/or Ursodiol may be used. Thalidomide with immunosuppressive properties has shown promising results in the treatment of chronic GVHD. Similar to thalidomide, clofazimine may also be coadministered with the composition of the present invention comprising LukE and LukD. Antibody targets for co-administered antibodies include, but are not limited to, T cell receptor (TCR), interleukin-2 (IL-2) and IL-2 receptors. Additionally, a CD(25) monoclonal antibody, anti-CD8 monoclonal antibody, or an anti-CD103 antibody may be co-administered for GVHD prophylaxis.

Another aspect of the present invention relates to a method of preventing or treating cancer in a subject. This method involves selecting a subject having or at risk of having cancer and administering, to the selected subject, a composition comprising an isolated LukE protein or polypeptide having a non-functional CXCR1/CXCR2 receptor binding domain and, optionally, an isolated LukD protein or polypeptide, in an amount effective to treat or prevent cancer in the subject Cancers suitable for treatment in accordance with this aspect of the present invention include those cancers, primary and metastatic forms, where CCR5 plays a role in mediating the development or progression of the cancer and where CCR5 antagonism has beneficial therapeutic implications. For example, suitable cancers include, without limitation, liver cancer (Ochoa-Callejero et al., "Maraviroc, a CCR5 Antagonist, Prevents Development of Hepatocellular Carcinoma in a Mouse Model," *PLOS One* 8(1):e53992 (2013), which is hereby incorporated by reference in its entirety), breast cancer (Velasco-Velazquez et al., "The CCL5/CCR5 Axis Promotes Metastasis in Basal Breast Cancer," *Oncoimmunology* 2(4): e23660 (2013) and Velasco-Velazquez et al., "CCR5 Antagonist Blocks Metastasis of Basal Breast Cancer Cells," *Cancer Res.* 72:3839 (2012), which are hereby incorporated by reference in their entirety), lung cancer (Lee et al., "Deficiency of C—C Chemokine Receptor 5 Suppresses Tumor Development Via Inactivation of NF-κB and Inhibition of Monocyte Chemoattractant Protein-1 in Urethane-Induced Lung Tumor Model," *Carcinogenesis* 33(12): 2520-2528 (2012), which is hereby incorporated by reference in its entirety method), and prostate cancer (Zhang et al., "Structure Activity Relationship Studies of Natural Product Chemokine Receptor CCR5 Antagonist Anibamine Toward the Development of Novel Anti-Prostate Cancer Agents," *Eur. J. Medicinal Chem.* 55:395-408 (2012), which is hereby incorporated by reference in its entirety).

In accordance with this aspect of the present invention, administering a composition comprising the modified LukE and LukD to a subject to target CCR5$^+$ cancer cells can be carried out concurrently with other anti-cancer therapeutic approaches, i.e., the composition is administered as part of a combination therapy. Accordingly, in one embodiment of the invention, the agent is administered in combination with one or more additional cancer therapeutics such as, a chemotherapeutic, radiation (e.g., external beam radiation therapy or brachytherapy), or an anti-angiogenic therapeutic.

Suitable chemotherapeutic agents for combination therapies include, without limitation, alkylating agents (e.g., chlorambucil, cyclophophamide, CCNU, melphalan, procarbazine, thiotepa, BCNU, and busulfan), antimetabolites (e.g., methotraxate, 6-mercaptopurine, and 5-fluorouracil), anthracyclines (daunorubicin, doxorubicin, idarubicin, epirubicin, and mitoxantrone), antitumor antibiotics (e.g., bleomycin, monoclonal antibodies (e.g., Alemtuzumab, Bevacizumab, Cetuximab, Gemtuzumab, Ibritumomab, Panitumumab, Rituximab, Tositumomab, and Trastuxmab), platiniums (e.g., cisplatin and oxaliplatin) or plant alkaloids (e.g., topoisomerase inhibitors, vinca alkaloids, taxanes, and epipodophyllotoxins).

Anti-angiogenic therapeutics suitable for use in a combination therapy approach with the compositions of the present invention include, without limitation a vascular endothelial growth factor (VEGF) inhibitor, basic fibroblast growth factor (bFGF) inhibitor, vascular endothelial growth factor receptor (VEGFR) antagonist, platelet-derived growth factor receptor (PDGFR) antagonist, fibroblast growth factor receptor (FGFR) antagonist, Angiopoietin receptor (Tie-2) antagonist, epidermal growth factor receptor (EGFR, ErbB) antagonist, or any combination thereof. A number of suitable small molecule angiogenic inhibitors are known in the art or are under clinical development (see, e.g., Wu et al., "Anti-Angiogenic Therapeutic Drugs for the Treatment of Human Cancer," *J Cancer Molecules* 4(2):37-45 (2008), which is hereby incorporated by reference in its entirety). These angiogenic inhibitors include, without limitation, Gefitinib (an ErbB inhibitor), Lapatinib (a dual ErbB1/ErbB2 inhibitor), Erlotinib, Canertinib (a pan-ErbB inhibitor), Vatalanib (VEGF receptor inhibitor), Imatinib (multi-targeted inhibitor of Bcr-Abl, c-kit, and PDGF-R inhibitor), Sunitinib (multi-targeted inhibitor of VEGFR, PDGFR Kit, Flt3, Tet and CSF1R inhibitor), Sorafenib (multi-targeted inhibit of VEGFR and PDGFR), Pazopanib (a multi-targeted inhibitor of VEGFR-1, VEGFR-2, VEGFR-3, PDGF-α, PDGFR-β, and c-kit). Alternatively, the anti-vasculogenic therapeutic is a monoclonal antibody. Suitable antibody therapeutics include, without limitation, Bevacizumab (VEGF antibody), IMC-1C11 (VEGFR-2 antibody), mF4-31C1 (VEGFR-3 antibody), and Vitaxin (integrin $\alpha_v\beta_3$ antibody).

Another aspect of the present invention relates to a method of identifying a compound capable of preventing or treating *S. aureus* infection and/or conditions resulting from a *S. aureus* infection. This method is typically carried out in vitro, i.e., in cell culture. This method involves providing a collection of candidate compounds and providing a population of cells expressing human CXCR1, CXCR2, and/or DARC. The method further involves treating the population of cells with an agent capable of inducing LukED or HlgAB mediated cytotoxicity, and contacting the population of treated cells with one or more candidate compounds from the collection. The method further involves measuring LukED or HlgAB mediated cytotoxicity level in the population of treated cells in the presence and absence of the one or more candidate compounds and comparing the measured level of LukED or HlgAB mediated cytotoxicity in the presence and in the absence of the one or more candidate compound. A decrease in the level of LukED or HlgAB mediated cytotoxicity in the presence of the one or more candidate compounds compared to in the absence of the one or more candidate compounds identifies a compound capable of preventing or treating *S. aureus* infection and/or a condition resulting from a *S. aureus* infection.

Cells expressing human CXCR1/CXCR2 that are suitable for use in accordance with this aspect of the invention include human PMNs, monocytes, natural killer cells, CD8+ T cell subsets, epithelial cells and endothelial cells. Cells expressing human DARC that are suitable for use in accordance with this aspect of the invention include human endothelial cells and red blood cells. Other suitable cells include any nucleated cell that has been engineered to express CXCR1/CXCR2 or DARC e.g., cells stably or transiently transfected with an expression construct containing a human CXCR1, CXCR2, and/or DARC polynucleotide sequences.

As described herein, this method of the present invention is designed to identify agents that inhibit some aspect of the cascade of events that leads to LukED or HlgAB-mediated cytotoxicity and lysis of human CXCR1/CXCR2$^+$ or DARC$^+$ cells. The targeted events that are part of the cascade include for example, binding of LukE or HlgA to CXCR1/CXCR2 or DARC, LukED or HlgAB oligomerization, and membrane pore formation by the LukED or HlgAB oligomer. The assay utilizes any mammalian or non-mammalian cell expressing the human CXCR1/CXCR2 or DARC that comprises the LukE and HlgA binding domain, suitable culture medium, and isolated or recombinant LukE/ LukD and HlgA/HlgB, or *S. aureus*. The assay further includes a labeled marker of cytotoxicity that is exposed to the cells before, during, or after the cells expressing human CXCR1/CXCR2 or DARC are contacted with an agent capable of inducing LukED or HlgAB cytotoxicity. The labeled marker of cytotoxicity may comprise a cell viability dye, a cell impermeable dye, and/or an indicator of cell lysis. Exemplary screening protocols suitable for use in accordance with this aspect of the present invention are described in detail in International Patent Application Serial No. PCT/US2013/032436 to Torres et al., which is hereby incorporated by reference in its entirety).

EXAMPLES

The following examples are provided to illustrate embodiments of the present invention but are by no means intended to limit its scope.

Materials and Methods for Examples 1-8

Cell Culture Conditions and Viral Transductions.

Primary human cells and THP-1 were cultured at 37° C. with 5% $CO_2$ in RPMI supplemented with 10% fetal bovine serum (FBS; Atlanta Biologicals) and penicillin (100 U ml-1) and streptomycin (0.1 mg ml-1) (Mediatech) unless stated otherwise. Overexpression and lentiviral-based knockdown of Cxcr2 or non-target shRNA were performed as previously described (Wan et al., "Cytokine Signals Through PI-3 Kinase Pathway Modulate Th17 Cytokine Production by CCR6+ Human Memory T Cells," *J. Exp. Med.* 208:1875-1887 (2011), which is hereby incorporated by reference in its entirety) and maintained in 1.3 g ml-1 puromycin. HEK293T cells were cultured at 37° C. with 5% CO2 in DMEM (Cellgro) and supplemented as described above.

Isolation of PBMCs.

Blood was obtained as buffy coats with the consent of de-identified donors from the New York Blood Center. PBMCs were isolated from blood using a Ficoll-Paque PLUS gradient (GE Amersham) and gated on CCR5+ cells, followed by anti-CD3 and CD14 cell surface staining for lymphocyte and monocyte populations. Cells were then incubated with LukED (75 nM) in the presence or absence of maraviroc (MVC, 100 ng ml-1).

CCR5 Inhibitor and Ligands.

Maraviroc was obtained through the AIDS Research and Reference Reagent Program, Division of AIDS (NIAID, NIH) and used at a final concentration of 100 ng ml-1. CXCL8 and CXCL1 were obtained from BioLegend and used at concentrations indicated in the text.

FACS Analysis.

Cell staining was performed as described previously (Alonzo et al., "CCR5 is a Receptor for *Staphylococcus aureus* Leukotoxin ED," *Nature* 493:51-55 (2013), which is hereby incorporated by reference in its entirety). FACS data were obtained using FACSDiva software on a LSRII flow cytometer (BD Biosciences). Data was analyzed using FlowJo software (Treestar).

Antibodies and Dyes.

Antibodies used for surface staining of primary human cells included the following: CXCR1-APC (clone 8F1/CXCR1), CXCR2-PE (clone 5E8/CXCR2), CD3-PE-Cy7 (clone UCHT1), CD8-Pacific Blue (clone HIT8a), CD14-Alexa Fluor 700 (clone HCD14), CD16-Alexa Fluor 488 (clone 3G8), CD56-PerCP-Cy5.5 (clone HCD56), CD19-Brilliant Violet 650 (clone HIB19), HLA-DR-Brilliant Violet 605 (clone L243), CD14-FITC (clone M5E2), CD18-PE-Cy5 (clone TS1/18) (BioLegend) and CCR5-PE (clone 2D7) (BD Pharmingen).

Antibodies used for surface staining of primary murine cells included the following: CXCR2-AF647 (clone TG11/CXCR2) (BioLegend), CCR5-PerCP-Cy5.5 (BD Pharmingen), streptavidin-PerCP-Cy5.5, (BioLegend), CD11b-PE (clone M1/70) (BD Pharmingen), B220-Alexa700 (clone RA3-6B2) (BioLegend), Ly6G-FITC (clone 1A8) (BD Biosciences), F480-PECy7 (clone BM8) (BioLegend) and CD16/CD32 Fc Block (clone 2.4G2) (BD Biosciences). The fixable viability dyes eFluor-450 and eFluor 780 were acquired from eBioscience.

Generation of $lukE^{DR}$ Constructs.

Isogenic DR mutant strains were generated by overlap PCR (see Tables 1-3 below for detailed primer and strain information). To generate $lukE^{DR1}$, plasmid from VJT8.87 containing lukE was used as template and amplified with primers VJT296 and VJT891; VJT297 and VJT894; or VJT892 and VJT893. For $lukE^{DR2}$, plasmid from VJT8.87 containing lukE was used as template and amplified with primers VJT296 and VJT895; VJT898 and VJT297; or VJT896 and VJT897. For $lukE^{DR3}$, plasmid from VJT8.87 containing lukE was used as template and amplified with primers VJT296 and VJT899; VJT902 and VJT297; or VJT900 and VJT901. For $lukE^{DR4}$, plasmid from VJT8.87 containing lukE was used as template and amplified with primers VJT296 and VJT903; VJT914 and VJT297; or VJT904 and VJT905. For $lukE^{DR5}$, plasmid from VJT8.87 containing lukE was used and amplified with primers VJT296 and VJT911; or VJT906 and VJT297. Plasmid from VJT8.89 containing lukS-PV was used and amplified with primers VJT912 and VJT913 to complete the $ukE^{DR5}$ locus. To obtain the final PCR product, each DNA fragment was included in a PCR reaction containing the flanking primers VJT296 and VJT297. Amplicons were cloned into pET14b-6×His (Novagen) using XhoI and BamHI restriction sites, resulting in N-terminal 6×Histidine (His) tagged $lukE^{DR}$ chimeric sequences.

Generation of $lukE^{DR}$ *E. coli* Expression Strains.

pET14b-6×His-ukEDR plasmids were transformed into *Escherichia coli* (*E. coli*) DH5α and transformants selected by ampicillin (Fisher) resistance. Positive clones were transformed into *E. coli* T7 LysY/LacQ (New England BioLabs) for purification of recombinant proteins as previously described (Alonzo et al., "*Staphylococcus aureus* Leucocidin ED Contributes to Systemic Infection by Targeting Neutrophils and Promoting Bacterial Growth in Vivo," *Mol. Microbiol.* 83:423-435 (2012); DuMont et al., "Characterization of a New Cytotoxin That Contributes to *Staphylococcus aureus* Pathogenesis," *Mol. Microbiol.* 79:814-825 (2011), which are hereby incorporated by reference in their entirety). Protein concentration was measured using the Thermo Scientific Pierce BCA Protein Assay kit.

Generation of the Hybrid/Mutated Proteins.

To generate $HlgA/D^{DR4}$ (amino acids 182-196 from HlgA are replaced with the corresponding amino acids from LukE): Newman genomic DNA was used as a template and amplified with primers VJT635 and VJT1267; and VJT1209 and VJT1266 (see Tables 1-3 below for detailed primer and strain information). To generate the full mutant locus, the resulting DNA products were used as template for a final sewing overlap extension PCR reaction using flanking primers VJT635 and VJT1209. The final amplicon was cloned into the pOS1-P$_{lukAB}$-lukA$^{s.s.}$-6xHis vector using BamHI and PstI restriction sites, which resulted in N-terminally 6xHistidine-tagged HlgA/E$^{DR4}$.

To generate HlgA/S$^{DR4}$ (amino acids 182-196 from HlgA are replaced with the corresponding amino acids from LukS-PV): Newman genomic DNA was used as a template and amplified with primers VJT635 and VJT1263; and VJT1209 and VJT1262 (see Tables 1-3 below for detailed primer and strain information). To generate the full mutant locus, the resulting DNA products were used as template for a final sewing overlap extension PCR reaction using flanking primers VJT635 and VJT1209. The final amplicon was cloned into the pOS1-P$_{lukAB}$-lukA$^{s.s.}$-6xHis vector using BamHI and PstI restriction sites, which resulted in N-terminally 6xHistidine-tagged HlgA/S$^{DR4}$.

To generate LukE$^{P184A,G186A,P187A,G189A}$: Newman genomic DNA was used as a template and amplified with primers VJT629 and VJT1179; and VJT1114 and VJT1180 (see Tables 1-3 below for detailed primer and strain information). To generate the full mutant locus, the resulting DNA products were used as template for a final sewing overlap extension PCR reaction using flanking primers VJT629 and VJT1114. The final amplicon was cloned into the pOS1-P$_{lukAB}$-lukA$^{s.s.}$-6xHis vector using BamHI and PstI restriction sites, which resulted in N-terminally 6xHistidine-tagged LukE$^{P184A,G86A,P187A,G189A}$.

Protein Production.

All the plasmids were transformed into *E. coli* DH5α and selected by ampicillin resistance. Positive plasmids were then electroporated into restriction negative *S. aureus* RN4220 competent cells, followed by electroporation into *S. aureus* Newman toxinless competent cells (Newman delta lukED, hlg::tet, lukAB::spec, hla::ermC) for protein production. Selection of mutants in *S. aureus* was performed by chloramphenicol resistance.

Leukotoxin Treatments.

HEK293T cells, THP-1, primary human PBMCs and primary murine peritoneal exudate cells were treated with LukE, LukD or LukED as previously described (Alonzo et al., "CCR5 is a Receptor for *Staphylococcus aureus* Leukotoxin ED," Nature 493:51-55 (2013), which is hereby incorporated by reference in its entirety). In all experiments 1-2×10$^5$ cells were seeded into 96-well plates. For experiments with primary human or murine cells, intoxications were carried out for 30 minutes on ice, and cells were then stained with a fixable viability dye as well as with antibodies for cell surface markers, followed by flow cytometric analysis. For all other cytotoxicity assays, cells were incubated in the presence of toxins for 1 hour at 37° C. plus 5% CO$_2$, then incubated for an additional 1-2 hours with a metabolic dye (Cell Titer, Promega).

TABLE 1

Bacterial strains used in this study.

| Strain | Background | Description | Designation | Reference |
|---|---|---|---|---|
| VJT8.16 | *S. aureus* Newman | Newman ΔlukED | ΔlukED | 3 |
| VJT31.58 | *S. aureus* Newman | Newman ΔΔΔΔ | Newman ΔΔΔΔ | This study |
| VJT8.87 | *Escherichia coli* DH5a | pET14b-6xHis-lukE | lukE | 3 |
| VJT8.89 | *Escherichia coli* DH5a | pET14b-6xHis-lukS-PV | lukD | 4 |
| VJT20.78 | *Escherichia coli* T7 LysY/LacQ | pET14b-6xHis-lukE | LukE | 3 |
| VJT21.44 | *Escherichia coli* T7 LysY/LacQ | pET14b-6xHis-lukD | LukD | 3 |
| VJT22.39 | *Escherichia coli* T7 LysY/LacQ | pET14b-6xHis-lukS-PV | LukS-PV | 4 |
| VJT22.41 | *Escherichia coli* T7 LysY/LacQ | pET14b-6xHis-lukF-PV | LukF-PV | 4 |
| VJT34.08 | *Escherichia coli* DH5a | pET14b-6xHis-lukE$^{DR1}$ | lukE$^{DR1}$ | This study |
| VJT34.09 | *Escherichia coli* DH5a | pET14b-6xHis-lukE$^{DR2}$ | lukE$^{DR2}$ | This study |
| VJT34.36 | *Escherichia coli* DH5a | pET14b-6xHis-lukE$^{DR3}$ | lukE$^{DR3}$ | This study |
| VJT34.58 | *Escherichia coli* DH5a | pET14b-6xHis-lukE$^{DR4}$ | lukE$^{DR4}$ | This study |
| VJT34.59 | *Escherichia coli* DH5a | pET14b-6xHis-lukE$^{DR5}$ | lukE$^{DR5}$ | This study |
| VJT34.13 | *Escherichia coli* T7 LysY/LacQ | pET14b-6xHis-lukE$^{DR1}$ | LukE$^{DR1}$ | This study |
| VJT34.15 | *Escherichia coli* T7 LysY/LacQ | pET14b-6xHis-lukE$^{DR2}$ | LukE$^{DR2}$ | This study |
| VJT34.49 | *Escherichia coli* T7 LysY/LacQ | pET14b-6xHis-lukE$^{DR3}$ | LukE$^{DR3}$ | This study |
| VJT34.60 | *Escherichia coli* T7 LysY/LacQ | pET14b-6xHis-lukE$^{DR4}$ | LukE$^{DR4}$ | This study |
| VJT34.62 | *Escherichia coli* T7 LysY/LacQ | pET14b-6xHis-lukE$^{DR5}$ | LukE$^{DR5}$ | This study |
| VJT31.59 | *S. aureus* Newman | Newman ΔΔΔΔ + pOS1-P$_{luk}$-lukA$^{s.s.}$-6xHis- | Empty | 19; this study |
| VJT31.62 | *S. aureus* Newman | Newman ΔΔΔΔ + pOS1-P$_{luk}$-lukA$^{s.s.}$-6xHis-lukED | lukED | This study |
| VJT36.01 | *S. aureus* Newman | Newman ΔΔΔΔ + pOS1-P$_{luk}$-lukA$^{s.s.}$-6xHis-lukE$^{D84}$D | luk$^{D84}$D | This study |
| VJT36.03 | *S. aureus* Newman | Newman ΔlukED + pJC1112-ΔlukED | ΔlukED | This study |
| VJT23.61 | *S. aureus* Newman | Newman ΔlukED + pJC1112-lukED | ΔlukED::lukED or + lukED | 3 |
| VJT35.90 | *S. aureus* Newman | Newman ΔlukED + pJC1112-lukE$^{DR4}$D | ΔlukED::lukE$^{DR4}$D or + lukE$^{DR4}$D | This study |

3 Alonzo et al., Mol. Microbiol. 83:423-435 (2012);
4 Alonzo et. al., Nature 493:51-55 (2013);
19 Dumont et al., PNAS (2013)

TABLE 2

Primers used in these studies

| Primer | Primer Sequence | SEQ ID NO: |
|---|---|---|
| VJT296 | 5'-CCCC-CTCGAG-AATACTAATATTGAAAATATTGGTGATG-3' | 17 |
| VJT891 | 5'-GTAATAAGTAGTCTTTGAATTAATAAAACCTTGCATTTTAAC-3' | 18 |
| VJT894 | 5'-CATATAAAAGCAATGAGGTGGCCATTCCAATATAATATAG-3' | 19 |
| VJT892 | 5'-TCAAAGACTACTTATTACAATTACAAAAACACAGATCATATAAAAGCAATGAGG-3' | 20 |
| VJT893 | 5'-CCTCATTGCTTTTATATGATCTGTGTTTTTGTAATTGTAATAAGTAGTCTTTGA-3' | 21 |
| VJT895 | 5'-GTTTTGTTGATTATAACTAATTGTTTTAGAATAATTAAATG-3' | 22 |
| VJT898 | 5'-GAACGTCAAAATTCAAATCTGTTAAATGGGGTG-3' | 23 |
| VJT896 | 5'-AGTTATAATCAACAAAACTATATCAGTGAAGTAGAACGTCAAAATTCA-3' | 24 |
| VJT897 | 5'-TGAATTTTGACGTTCTACTTCACTGATATAGTTTTGTTGATTATAACT-3' | 25 |
| VJT899 | 5'-GTGATAAATGAATTAGCTTTAACACCCCATTTAAC-3' | 26 |
| VJT902 | 5'-GTAAAATGTCTGGACATGATCCAAATTTATTTGTTGG-3' | 27 |
| VJT900 | 5'-GCTAATTCATTTATCACATCATTAGGTAAAATGTCTGGACATGAT-3' | 28 |
| VJT901 | 5'-ATCATGTCCAGACATTTTACCTAATGATGTGATAAATGAATTAGC-3' | 29 |
| VJT903 | 5'-CTATATGGTTTATATCCAACAAATAAATATCTATCATGCGCAGA-3' | 30 |
| VJT914 | 5'-GACTATTTTGTTCCAGACAATCAATTGCCACCTTTAGTTCAAAG-3' | 31 |
| VJT904 | 5'-TGTTGGATATAAACCATATAGTCAAAATCCGAGAGACTATTTTGTTCCAGAC-3' | 32 |
| VJT905 | 5'-GTCTGGAACAAAATAGTCTCTCGGATTTTGACTATATGGTTTATATCCAACA-3' | 33 |
| VJT911 | 5'-CATGAGTAACATCCATATTTCTACCATATGAAATTTCAAATTC-3' | 34 |
| VJT906 | 5'-GAGACTATTTTGTTCCAGATAATCAATTGCCACCTTTAG-3' | 35 |
| VJT912 | 5'-GAATTTGAAATTTCATATGGTAGAAATATGGATGTTACTCATG-3' | 36 |
| VJT913 | 5'-CAAAGTTTCTATTTACAAATGCATTGTGTATTCTAGATCCTTC-3' | 37 |
| VJT297 | 5'-CCCC-GGATCC-TTA-ATTATGTCCTTTCACTTTAATTTCG-3' | 38 |
| VJT605 | 5'-CCCC-CTGCAG-GATAGGTGAGATGCATACACAAC-3' | 39 |
| VJT299 | 5'-CCCC-GGATCC-TTA-TACTCCAGGATTAGTTTCTTTAG-3' | 40 |
| VJT1019 | 5'-CAATATTTTCAATATTAGTATTTGCTCTAGATTCTTGAATCGGAGA-3' | 41 |
| VJT1020 | 5'-TCTCCGATTCAAGAATCTAGAGCAAATACTAATATTGAAAATATTG-3' | 42 |
| VJT1021 | 5'-ACTAATTTTTTCATTTTCATATTAATTATGTCCTTTCACTT-3' | 43 |
| VJT1022 | 5'-AAGTGAAAGGACATAATTAATATGAAATGAAAAAATTAGT-3' | 44 |
| VJT629 | 5'-CCC-GGATCC-AATACTAATATTGAAAATATTGGTGATG-3' | 45 |
| VJT630 | 5'-CCC-CTGCAG-TTA-TACTCCAGGATTAGTTTCTTTAG-3' | 46 |
| VJT629 | 5'-CCCGGATCC-AATACTAATATTGAAAATATTGGTGATG-3' | 47 |
| VJT635 | 5'-CCCGGATCC-GAAAATAAGATAGAAGATATCGGCC-3' | 48 |
| VJT1114 | 5'-CCCCTGCAGTTA-ATTATGTCCTTTCACTTTAATTTCG-3' | 49 |
| VJT1179 | 5'-GCAAAATATTCTCTTGCTGATGCTGTTGCTGCATTTGCACTTTGTACGAATAAATATC-3' | 50 |
| VJT1180 | 5'-GATATTTATTCGTACAAAGTGCAAATGCAGCAACAGCATCAGCAAGAGAATATTTTGC-3' | 51 |
| VJT1209 | 5'-CCCCTGCAGTTACTTAGGTGTGATGCTTTTAATTTTTAC-3' | 52 |
| VJT1262 | 5'-GGATATAAACCATATAGTCAAAATCCGAGAGACTATTTTGTTCCAGATAATCAACTACCTCC-3' | 53 |

TABLE 2-continued

Primers used in these studies

| Primer | Primer Sequence | SEQ ID NO: |
|---|---|---|
| VJT1263 | 5'-AACAAAATAGTCTCTCGGATTTTGACTATATGGTTTATATCCTGCAAATAAGTATTGATCATATGC-3' | 54 |
| VJT1266 | 5'-CAAAGTCCAAATGGTCCAACAGGTTCAGCAAGAGAATATTTTGCTCCAGATAATCAACTACCTCC-3' | 55 |
| VJT1267 | 5'-AGCAAAATATTCTCTTGCTGAACCTGTTGGACCATTTGGACTTTGTGCAAATAAGTATTGATCATATGC-3' | 56 |

TABLE 3

Plasmids used in these studies

| Plasmid name | Description | Reference |
|---|---|---|
| pET14b-6xHis- | Cloning and expression vector containing a 6x-His tag | Novagen |
| pOS1-p$_{lukA}$-lukA$^{s.s.}$-6xHis- | Modified pOS1 vector containing the lukA promoter with its endogenous signal sequence driving gene expression. | 19 |
| pOS1-p$_{lukA}$-lukA$^{s.s.}$-6xHis-lukED | Modified pOS1 vector containing the lukA promoter with its endogenous signal sequence driving lukED expression. | This study |
| pOS1-p$_{lukA}$-lukA$^{s.s.}$-6xHis-lukE$^{DR4}$D | Modified pOS1 vector containing the lukA promoter with its endogenous signal sequence driving lukE$^{DR4}$D expression. | This study |
| pJC1112- | Chromosomal integration vector that results in integration at the SAPI-1 site. | 3 |
| pJC1112-lukED | Chromosomal integration vector with lukED integrated at the SaPII site resulting in single copy complementation. | 3 |
| pJC1112-lukE$^{DR4}$D | Chromosomal integration vector with lukE$^{DR4}$D integrated at the SaPII site resulting in single copy complementation. | This study |

3 Alonzo et al., Mol. Microbiol. 83:423-435 (2012);
19 Dumont et al., PNAS (2013)

Binding and Competition Assays.

For binding assays, increasing concentrations of GFP-LukE or GFP-LukD were added to 5×10$^4$ human PMNs and incubated for 30 minutes on ice, then washed once in FACS buffer and fixed for 15 minutes at room temperature followed by flow cytometric analysis. Mean fluorescence intensity (MFI) of GFP$^+$ cells was measured to establish the toxin concentration required to achieve saturable binding. For remaining competition assays, increasing concentrations of either LukE or LukS-PV were co-incubated with a constant saturable concentration of LukE-GFP (300 nM) for 30 minutes. Cells were washed once in FACS buffer, fixed for 15 minutes in FACS fixing buffer, washed again in FACS buffer, and binding was assessed by flow cytometry. The mean GFP fluorescent intensity is represented as % GFP$^+$, based on the maximal fluorescence observed upon incubation with 300 nM GFP-LukE. For competition assays using CXCL8 or CXCL1, a dose response of either chemokine was added to human PMNs for 30 minutes on ice, followed by addition of 300 nM GFP-LukE. Cells were washed once in FACS buffer, fixed for 15 minutes in FACS fixing buffer, washed again in FACS buffer, and binding was assessed by flow cytometry as described above. Results for these assays were depicted graphically using GraphPad PRISM software (version 5.0f, GraphPad PRISM Software, Inc.).

Generation of S. aureus Chromosomal Integration Strains.

For complementation with WT LukED, the entire lukED locus was amplified from S. aureus Newman genomic DNA using the following primers: VJT605 and VJT299 and chromosomal integration performed as described (Alonzo et al., "Staphylococcus aureus Leucocidin ED Contributes to Systemic Infection by Targeting Neutrophils and Promoting Bacterial Growth in Vivo," Mol. Microbiol. 83:423-435 (2012), which is hereby incorporated by reference in its entirety). To generate the lukE$^{DR4}$D integration construct, the lukED promoter region was amplified from S. aureus Newman genomic DNA using primers VJT605 and VJT1019. The lukE$^{DR4}$ coding region was amplified using purified plasmid from strain VJT34.58 containing lukE$^{DR4}$ as a template and amplified with primers VJT1020 and VJT1021. S. aureus Newman genomic DNA was used to amplify lukD and the intergenic region between lukE and lukD using primers VJT1022 and VJT299. A final overlap PCR reaction was setup with the resultant DNA fragments and primers VJT605 and VJT299. The lukED and lukE$^{DR4}$D constructs were transformed into E. coli DH5α and clones selected by ampicillin resistance. The purified plasmids were cloned into pJC1112 using BamHI and PstI restriction sites and transformed into DH5α. The resulting recombinant plasmids were introduced by electroporation into strain RN9011, containing plasmid pRN7023 which encodes the SaPI-1 phage integrase to facilitate single copy chromosomal integration into the SaPI-1 site and selected for based on chloramphenicol and erythromycin resistance, as previously described (Alonzo et al., "Staphylococcus aureus Leucocidin ED Contributes to Systemic Infection by Targeting Neutrophils and Promoting Bacterial Growth in Vivo," Mol. Microbiol. 83:423-435 (2012), which is hereby incorporated by reference in its entirety). The SaPI-1 integrated constructs were then transduced into strain VJT8.16, Newman ΔlukED, using previously described methods (Alonzo et al., "Staphylococcus aureus Leucocidin ED Contributes to Systemic Infection by Targeting Neutrophils and Promoting Bacterial Growth in Vivo," Mol. Microbiol. 83:423-435 (2012), which is hereby incorporated by reference in its entirety).

To generate an empty vector-containing ΔlukED strain, the pJC1112 vector was electroporated into RN9011 as above. Bacteriophage-mediated transduction was then used to introduce the integrated complementation vector into *S. aureus* strain Newman ΔlukED using previously described methods (Alonzo et al., "*Staphylococcus aureus* Leucocidin ED Contributes to Systemic Infection by Targeting Neutrophils and Promoting Bacterial Growth in Vivo," *Mol. Microbiol.* 83:423-435 (2012), which is hereby incorporated by reference in its entirety).

Bacterial Strains and Growth Conditions.

*E. coli* strains were routinely grown in Luria Bertani (LB) broth supplemented with ampicillin at 30° C. with 180 RPM shaking. To purify proteins from *E. coli*, bacteria were subcultured 1:100 into LB supplemented with ampicillin and incubated at 37° C. with 220 RPM shaking, then induced overnight with a final concentration of isopropyl β-D-1-thiogalactopyranoside of 0.1 mM at 16° C. and 220 RPM. *S. aureus* strains were routinely grown at 37° C. with 180 RPM shaking in RPMI plus 10% casamino acids or tryptic soy broth in the presence or absence of antibiotic as indicated. To generate a *S. aureus* Newman toxinless strain, a Newman ΔlukED parental strain previously described (Alonzo et al., "*Staphylococcus aureus* Leucocidin ED Contributes to Systemic Infection by Targeting Neutrophils and Promoting Bacterial Growth in Vivo," *Mol. Microbiol.* 83:423-435 (2012), which is hereby incorporated by reference in its entirety) was transduced with phage encoding hlgACB::tet, followed by lukAB::spec, then hla::erm.

Generation of *S. aureus* Newman Toxinless Strain Containing lukED and lukE$^{DR4}$D.

Study of the effects of LukED and its derivative LuE$^{DR4}$D ex vivo is complicated by the low level expression of the toxin under in vitro growth conditions (Alonzo et al., "*Staphylococcus aureus* Leucocidin ED Contributes to Systemic Infection by Targeting Neutrophils and Promoting Bacterial Growth in Vivo," *Mol. Microbiol.* 83:423-435 (2012), which is hereby incorporated by reference in its entirety) as well as the greater in vitro abundance of other leukotoxins that target similar cell types used in ex vivo assays. To overcome these complications a system of assessing leukotoxin activity in isolation was implemented through the use of the toxinless Newman strain ΔΔΔΔ (ΔlukED, Δhlg::tet, ΔlukAB::spec, Δhla::erm) described above, and plasmid based expression of LukED and its derivative LuE$^{DR4}$D. The lukED and the lukE$^{DR4}$D loci were amplified from the pJC1112 chromosomal integration strains described above using primers VJT629 and VJT630 with BamHI and PstI restriction sites. Amplicons were subcloned into the modified pOS1 vector designed to express 6×His tagged leukotoxins under the control of the ukA promoter (pOS1-plukA-ukAs.s.-6×His) as previously described (Dumont et al., "The *Staphylococcus aureus* LukAB Cytotoxin Kills Human Neutrophils by Targeting the CD11b Subunit of the Integrin Mac-1," PNAS (2013), which is hereby incorporated by reference in its entirety), followed by transformation into the toxinless *S. aureus* strain Newman ΔΔΔΔ (ΔlukED, Δhlg::tet, ΔlukAB::spec, Δhla::erm).

Ex Vivo Infection Experiments.

*S. aureus* strains containing either the pOS1-plukA-lukAs.s.-6×His vector construct containing either no toxin (empty), lukED or ukE$^{DR4}$D were subcultured for 4.5 hours, followed by normalization to $1 \times 10^9$ CFU per ml in RPMI+ 10% FBS. Cells were diluted 1:10 and 20 μl were added to 80 μl of media containing $2 \times 10^5$ PMNs seeded into 96-well plates. Infections were carried out for 3.5 hours at 37° C. with shaking at 180 RPM. 2 μg ml-1 of lysostaphin was added for 20 minutes at 37° C. with shaking at 180 RPM to kill all bacteria. Cells were centrifuged for 5 minutes at 1,500 RPM and 4° C., followed by fixing in FACS fixing buffer (PBS+2% FBS+2% paraformaldehyde+0.05% sodium azide). To analyze toxin mediated killing by flow cytometry, cellular depletion from gated live cells was evaluated. Percent cell death was calculated by comparing cells remaining in the live gate to that of Newman ΔΔΔΔ strain containing the empty pOS1-plukA modified empty vector (no toxin), which was set to 0% dead.

Biochemical Assays to Examine Interactions Between LukED and CXCR1 or CXCR2.

HEK293T cells were transiently transfected with cDNAs encoding N-terminal HA-tagged CXCR1 or CXCR2 (Missouri S&T cDNA Resource Center) using Lipofectamine 2000 (Invitrogen). Forty-eight hours post transfection, cells were detached with PBS containing 5 mM EDTA and membrane proteins were solubilized (approximately $1 \times 10^6$ cells per condition) for 1 hour using lysis buffer (PBS+10 mM imidazole (Fisher)+1% Brij 010 (Sigma)+1 mM PMSF (Thermo Scientific)+2× protease inhibitor pellets (Roche)). His-tagged LukE and LukD were incubated with equilibrated Ni-NTA resin (Qiagen) for 2 hours, followed by three washes in lysis buffer. Lysates and resin were then incubated together for 2 hours, followed by three washes in lysis buffer and final resuspension of resin in 45 μl of 4×SDS sample buffer. Protein samples were run on 10% SDS-PAGE gels at 80V, followed by transfer to nitrocellulose membranes (GE) for 1 hour at 1 Amp. Membranes were blocked with PBS+ 0.01% Tween-20+5% non-fat milk for 1 hour and incubated overnight at 4° C. with either anti-His antibody diluted at 1:3,000 in PBS+0.01% Tween-20 for toxins (Cell Sciences) or anti-HA antibody diluted at 1:1,000 in with PBS+0.01% Tween-20+5% non-fat milk for receptors (Covance). The following day, secondary goat anti-mouse HRP antibody (Bio-Rad) was added to membranes for 1 hour in PBS+ 0.01% Tween-20+5% non-fat milk followed by incubation with Super Signal West Femto Maximum Sensitivity Substrate (Thermo Scientific) for detection on autoradiography films (LabScientific, Inc).

Measurements of Calcium Mobilization.

CXCR1 and CXCR2 activation on human PMNs was evaluated using the fluorescent calcium indicator Fluo4-AM (Invitrogen) as previously described (Alonzo et al., "CCR5 is a Receptor for *Staphylococcus aureus* Leukotoxin ED," *Nature* 493:51-55 (2013), which is hereby incorporated by reference in its entirety). Briefly, cells were incubated for 30 minutes at room temperature with 3 μM of Fluo4-AM in Hank's Balanced Salt Solution (HBSS) followed by three washes in HBSS and equilibration at 37° C. for 30 minutes. Baseline calcium levels were analyzed over time on a flow cytometer for 60 seconds. At this point, CXCL8, CXCL1 or LukE (300 nM) were added to cells and the mean fluorescence intensity over time was evaluated for an additional 4 minutes. The mean fluorescent intensity over 5-second intervals was plotted for graphical display.

Murine In Vitro and In Vivo Experiments.

To evaluate LukED-mediated killing of murine cells in vitro, C57BL/6 WT mice (Taconic) were injected intraperitoneally with $1 \times 10^7$ CFU of heatkilled *S. aureus* Newman ΔlukED. Twenty-four hours post injection, another dose of $1 \times 10^7$ CFU of heat-killed *S. aureus* Newman ΔlukED was injected as before. After an additional twenty-four hours, mice were sacrificed and immune cells were collected by peritoneal cavity lavage using 8 ml of PBS. Red blood cells were lysed using 2 ml ACK lysis buffer (Gibco) followed by resuspension of remaining peritoneal exudate cells in RPMI+10% FBS. Cells were incubated with PBS, LukED or LukE$^{DR4}$D (300 nM) and incubated for 30 minutes on ice. After incubation, the cells were washed three times with PBS then stained with the fixable viability dye eFluor-450, followed by cell surface staining with CD11b, B220, F480, CD3, Ly6G, CCR5 and CXCR2 antibodies. Cell viability of specific immune cell populations was subsequently analyzed on an LSRII flow cytometer (BD). FACS plots are representative of results obtained from cells isolated from at least 3 independent animals. Cell death was quantified and displayed graphically as the percentage of eFluor-450+ cells.

For in vivo experiments, 8-week old female C57BL/6 mice (Taconic) were anesthetized with 250 µl of Avertin (2,2,2-tribromoethanol dissolved in tert-amyl-alcohol and diluted to a final concentration of 2.5% v/v in sterile saline), followed by retro-orbital injection of 1×10$^7$ CFU of isogenic Newman ΔlukED, ΔlukED::lukED and ΔlukED::lukEDR4D. Ninety-six-hours post infection, mice were sacrificed and organs were harvested and homogenized to evaluate the bacterial burden (colony forming units, CFUs). To determine the effects of infection with these strains on immune cells, organ immune cell suspensions were purified using a 40/80 Percoll (GE Healthcare) density gradient centrifugation and were subsequently processed and stained as described before (Alonzo et al., "CCR5 is a Receptor for *Staphylococcus aureus* Leukotoxin ED," *Nature* 493:51-55 (2013), which is hereby incorporated by reference in its entirety). Cell viability of specific immune cells populations was determined by flow cytometric analysis on an LSRII (BD) flow cytometer. FACS plots are representative of results obtained from at least 9 infected animals per group. Cell death was quantified and displayed graphically as the percentage of eFluor450$^+$ cells.

For survival experiments, 3-hour subcultures of isogenic strains Newman ΔlukED, ΔlukED::lukED and ΔlukED::lukE$^{DR4}$D were normalized to 5×10$^8$ CFU per milliliter using PBS. Five to six week old, female ND4 mice (Harlan) were anesthetized intraperitoneally with 250 µl of Avertin, followed by retro-orbital injection of 100 µl of normalized bacteria, for a final CFU count of 5×10$^7$ CFU. Survival of mice was monitored over time until signs of morbidity, such as hunched posture, ruffled fur, weight loss, inability to acquire food or water, ataxia and hind limb paralysis were reached, at which point the mice were immediately sacrificed and survival curves plotted over time (hours).

Exoprotein Profiles and Immunoblot Analyses of *S. aureus* Protein Secretion.

*S. aureus* strains Newman ΔΔΔΔ+pOS1-plukA-lukAs.s.-6×His-lukED, Newman ΔΔΔΔ+pOS1-plukA-lukAs.s.-6×His-lukE$^{DR4}$D, Newman ΔlukED+pJC1112-, Newman ΔlukED+pJC1112-lukED, Newman ΔlukED+pJC1112-lukE$^{DR4}$D and Newman ΔlukEDΔhlgACB were grown to late logarithmic phase at 37° C. with 180 RPM shaking for 5 hours. Bacterial cultures were then centrifuged at 4,000 RPM for 15 minutes followed by removal of 1.3 ml bacterial supernatant and addition of tri-chloro acetic acid (final concentration of 10%). Proteins were allowed to precipitate overnight at 4° C. The following day precipitated proteins were pelleted by centrifugation at 15,000 RPM for 30 minutes, washed with 100% ethanol, and resuspended in 60 µl of 1× sample buffer. Samples were vortexed and boiled for 5 minutes prior to SDS-PAGE. For anti-His, anti-LukE, and anti-LukD immunoblots, *S. aureus* exoproteins were resolved on 10% SDS-PAGE gels followed by transfer to nitrocellulose at 1 Amp for 1 hour. Membranes were blocked for 1 hour in PBS+0.01% Tween-20+5% non-fat milk; probed with primary antibodies at the following dilutions: anti-His (1:3,000), anti-LukE (1:5,000), and anti-LukD (1:5,000); washed three times with PBST; probed with secondary goat anti-mouse (for anti-His antibody) or anti-rabbit (for anti-LukE and anti-LukD antibodies) Alexafluor-680 conjugated antibodies for 1 hour; followed by imaging on an Odyssey imager (LI-COR). For strains overexpressing LukED or LukE$^{DR4}$D (Newman ΔΔΔΔ+pOS1-plukA-lukAs.s.-6×His-lukED, Newman ΔΔΔΔ+pOS1-plukAlukA$^{s.s.}$-6×His-ukE$^{DR4}$D) a coomassie stained gel is shown to demonstrate the decreased affinity for the LukE antibody toward the LukE$^{DR4}$ mutant. For strains producing endogenous levels of LukED and LukE$^{DR4}$D (Newman ΔlukED+pJC1112-, Newman ΔlukED+pJC1112-lukED, Newman ΔlukED+pJC1112-lukE$^{DR4}$D) a ΔlukEDΔhlgACB double mutant was included due to cross-reactivity of the anti-LukE antibody with HlgC3. All images are representative of at least three independent experiments. α-LukE and α-LukD antibodies were generated as previously described.

Structural Modeling of LukE/LukS-PV Structural Diversity.

The LukE and LukS-PV amino acid sequences were aligned with ClustalW and scored with a Risler matrix according to the extent of sequence variation using ESPript. Scores were displayed on the LukE structure surface with a color ramp (red, orange, yellow, green, light blue, dark blue) in which strictly conserved residues are colored red, and the most divergent residues are colored dark blue. Conservative substitutions are represented by intermediate colors. All structural figures were prepared using PyMOL.

Example 1—LukED Targets CXCR1 and CXCR2 to Kill Monocytes and PMNs

*S. aureus* is a Gram positive bacterium that is responsible for significant morbidity and mortality worldwide (DeLeo & Chambers, "Reemergence of Antibiotic-Resistant *Staphylococcus aureus* in the Genomics Era," *J. Clin. Invest.* 119:2464-2474 (2009), which is hereby incorporated by reference in its entirety). The pathogenesis of this organism depends on the production of an arsenal of virulence factors that are thought to contribute to immune evasion and subsequent manifestation of disease (Vandenesch et al., "*Staphylococcus aureus* Hemolysins, Bi-Component Leukocidins, and Cytolytic Peptides: A Redundant Arsenal of Membrane-Damaging Virulence Factors?" *Front. Cell. Infect. Microbiol.* 2:12 (2012); Nizet, V., "Understanding How Leading Bacterial Pathogens Subvert Innate Immunity to Reveal Novel Therapeutic Targets," *J. Allergy Clin. Immunol.* 120:13-22 (2007), which are hereby incorporated by reference in their entirety). Strains associated with human infection can produce up to five different bi-component leukotoxins (LukSF-PV/PVL, HlgAB, HlgCB, LukED, and LukAB/HG) (Alonzo & Torres, "Bacterial Survival Amidst an Immune Onslaught: The Contribution of the *Staphylococcus aureus* Leukotoxins," *PLoS Pathog* 9:e1003143 (2013); Alonzo et al., "*Staphylococcus aureus* Leucocidin ED Contributes to Systemic Infection by Targeting Neutrophils and Promoting Bacterial Growth in Vivo," *Mol. Microbiol.* 83:423-435 (2012); Alonzo et al., "CCR5 is a Receptor for *Staphylococcus aureus* Leukotoxin ED," *Nature* 493:51-55 (2013); Vandenesch et al., "*Staphylococcus aureus* Hemolysins, Bi-Component Leukocidins, and Cytolytic Peptides: A Redundant Arsenal of Membrane-Damaging Virulence Factors?" *Front. Cell. Infect. Microbiol.* 2:12 (2012); Panton & Valentine, "Staphylococcal Toxin," *The Lancet* 506-508 (1932); Loffler et al., "*Staphylococcus* aureus Panton-Valentine Leukocidin is a Very Potent Cytotoxic Factor for Human Neutrophils," *PLoS Pathog.* 6:e1000715 (2010); Labandeira-Rey et al., "*Staphylococcus aureus* Panton-Valentine Leukocidin Causes Necrotizing Pneumonia," *Science* 315:1130-1133 (2007); Yamashita et al., "Crystal Structure of the Octameric Pore of Staphylococcal Gamma-Hemolysin Reveals the Beta-Barrel Pore Formation Mechanism by Two Components," *Proc. Nat'l. Acad. Sci. U.S.A.* 108:17314-17319 (2011); Dalla Serra et al., "*Staphylococcus aureus* Bicomponent Gamma-Hemolysins, HlgA, HlgB, and HlgC, Can Form Mixed Pores Containing All Components," *J. Chem. Inf. Model.* 45:1539-1545 (2005); Morinaga et al., "Purification, Cloning and Characterization of Variant LukE-LukD With Strong Leukocidal Activity of Staphylococcal Bi-Component Leukotoxin Family," *Microbiol. Immunol.* 47:81-90 (2003); Gravet et al., "Characterization of a Novel Structural Member, LukE-LukD, of the Bi-Component Staphylococcal Leucotoxins Family," *FEBS Lett.* 436:202-208 (1998); DuMont et al., "Characterization of a New Cytotoxin That Contributes to *Staphylococcus aureus* Pathogenesis," *Mol. Microbiol.* 79:814-825 (2011); Dumont et al., "*Staphylococcus aureus* Elaborates Leukocidin AB to Mediate Escape From Within Human Neutrophils," *Infect. Immun.* 81:1830-1841 (2013); Ventura et al., "Identification of a Novel *Staphylococcus aureus* Two-Component Leukotoxin Using Cell Surface Proteomics," *PLoS One* 5:e11634 (2010), which are hereby incorporated by reference in their entirety). These toxins potently target and kill human neutrophils (polymorphonuclear cells; PMNs), innate immune cells critical for defense against bacterial infections (Loffler et al., "*Staphylococcus aureus* Panton-Valentine Leukocidin is a Very Potent Cytotoxic Factor for Human Neutrophils," *PLoS Pathog.* 6:e1000715 (2010), which is hereby incorporated by reference in its entirety). For many years these toxins were thought to be redundant, however the recent identification of cellular factors that facilitate their unique cellular tropism has proven otherwise (Alonzo et al., "CCR5 is a Receptor for *Staphylococcus aureus* Leukotoxin ED," *Nature* 493:51-55 (2013); Spaan et al., "The Staphylococcal Toxin Panton-Valentine Leukocidin Targets Human C5a Receptors," *Cell Host & Microbe* 13:584-594 (2013); Dumont et al., "The *Staphylococcus aureus* LukAB Cytotoxin Kills Human Neutrophils by Targeting the CD11b Subunit of the Integrin Mac-1," *PNAS* (2013), which are hereby incorporated by reference in their entirety). While investigating the effects of LukED on primary human peripheral blood mononuclear cells (PBMCs) it was observed that monocytes within PBMCs isolated from a Δ32Ccr5 individual, which naturally lacks CCR5 on the cell surface (Oswald-Richter et al., "Identification of a CCR5-Expressing T Cell Subset That is Resistant to R5-Tropic HIV Infection," *PLoS Pathog.* 3:e58 (2007), which are hereby incorporated by reference in their entirety) are targeted in a LukED-mediated, CCR5-independent manner (FIG. 1A). Similarly, monocytes from PBMCs isolated from Ccr5$^{+/+}$ individuals were susceptible to LukED even in the presence of maraviroc, a CCR5 antagonist known to block LukED mediated killing of CCR5$^+$ cells (Alonzo et al., "CCR5 is a Receptor for *Staphylococcus aureus* Leukotoxin ED," *Nature* 493:51-55 (2013), which is hereby incorporated by reference in its entirety) (FIG. 2). Moreover, PMNs from Ccr5$^{+/+}$ and Δ32Ccr5 donors were equally susceptible to LukED (FIG. 1), indicating that LukED targets human monocytes and PMNs in a CCR5-independent manner.

Figure 1C:
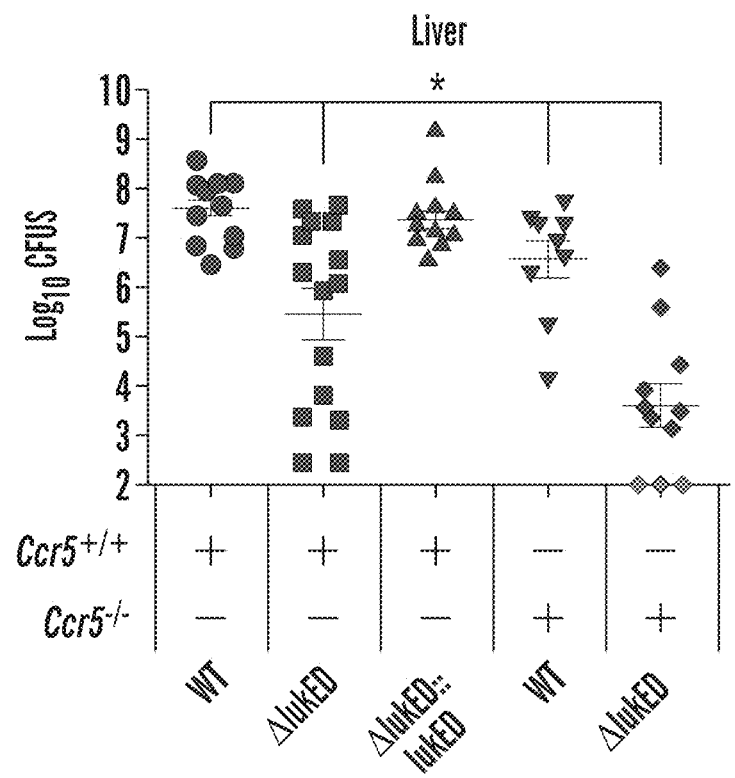
Figure 2:
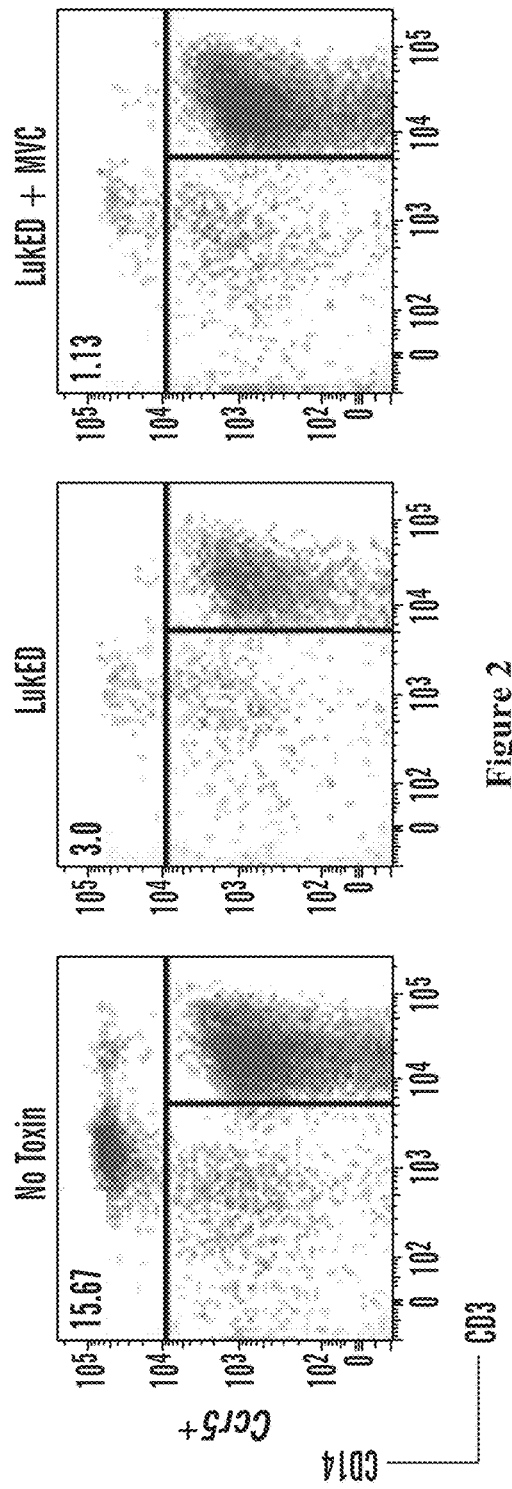
FIG. 2 shows that Maraviroc (MVC) does not protect monocytes from LukED-mediated death. CD14$^+$ and CD3$^+$ cells present in CCR5$^+$-gated PBMC treated with PBS (no toxin), LukED (75 nM) or LukED (75 nM) plus MVC (100 ng/mL).

To evaluate the CCR5-independent contribution of LukED on *S. aureus* virulence in vivo, Ccr5$^{+/+}$ and Ccr5$^{-/-}$ mice were systemically infected with isogenic *S. aureus* wild type (WT) and ΔlukED strains and the bacterial burden in infected livers was evaluated 96 hours post-infection. ΔlukED-infected Ccr5$^{+/+}$ mice displayed a 2-log reduction in CFU compared to those infected with WT or the complementation strain (ΔlukED::lukED) (FIG. 1C). Consistent with prior studies, the bacterial burden in Ccr5$^{-/-}$ mice infected with WT *S. aureus* was reduced 1-log compared to Ccr5$^{+/+}$ mice infected with WT *S. aureus* (Alonzo et al., "CCR5 is a Receptor for *Staphylococcus aureus* Leukotoxin ED," *Nature* 493:51-55 (2013), which is hereby incorporated by reference in its entirety). In contrast, Ccr5$^{-/-}$ mice infected with the ΔlukED strain showed a 3-log reduction in bacterial burden compared to Ccr5$^{+/+}$ mice infected with WT *S. aureus*, indicating a strong CCR5-independent contribution of LukED to *S. aureus* pathogenesis (FIG. 1C). Together these data indicated the existence of an alternate LukED cellular receptor on the surface of PMNs and monocytes, whose targeting contributes to establishment of systemic *S. aureus* infection.

To identify these targets, chemokine receptors present on the surface of phagocytes were ectopically expressed on Human Embryonic Kidney 293T cells (HEK293T) followed by the addition of LukED. Using this approach, it was determined that chemokine receptors CXCR1, CXCR2, and DARC were sufficient to render HEK293T cells susceptible to LukED, but not to the homologous leukotoxin LukSF-PV (FIG. 1D, FIG. 3, and FIG. 5A), which does not target CXCR2 (Spaan et al., "The Staphylococcal Toxin Panton-Valentine Leukocidin Targets Human C5a Receptors," *Cell Host & Microbe* 13:584-594 (2013), which is hereby incorporated by reference in its entirety).

CXCR1 and CXCR2 are also known as the interleukin 8 receptor α and β chain, respectively (Stillie et al., "The Functional Significance Behind Expressing Two IL-8 Receptor Types on PMN," *J. Leukoc. Biol.* 86:529-43 (2009), which is hereby incorporated by reference in its entirety). These chemokine receptors interact to form heterodimeric and homodimeric complexes in the surface of PMNs to facilitate the high affinity binding of CXCL8, also known as IL8, which promotes the recruitment of immune cells to the site of infection (Stillie et al., "The Functional Significance Behind Expressing Two IL-8 Receptor Types on PMN," *J. Leukoc. Biol.* 86:529-43 (2009), which is hereby incorporated by reference in its entirety). CXCR1 and CXCR2 are homologous proteins exhibiting 77% amino acid identity, and are expressed in the myeloid lineage, primarily in PMNs and monocytes (Stillie et al., "The Functional Significance Behind Expressing Two IL-8 Receptor Types on PMN," *J. Leukoc. Biol.* 86:529-43 (2009), which is hereby incorporated by reference in its entirety) as well as in natural killer cells, CD8+ T cell subsets, and epithelial and endothelial cells. In contrast, the Duffy antigen receptor for chemokines (DARC), also known as Fy glycoprotein (FY) or CD234, is found primarily on the surface of red blood cells (RBC) and endothelial cells. DARC is a CC and CXC chemokine "sink", which is thought to remove excess chemokines from the bloodstream. DARC is also the receptor for the human malarial parasites *Plasmodium vivax* and *Plasmodium knowlesi*. Collectively, the discovery that LukED binds CXCR1/CXCR2 and DARC provides an explanation for how LukED targets PMNs and RBC, respectively.

Figure 1D:
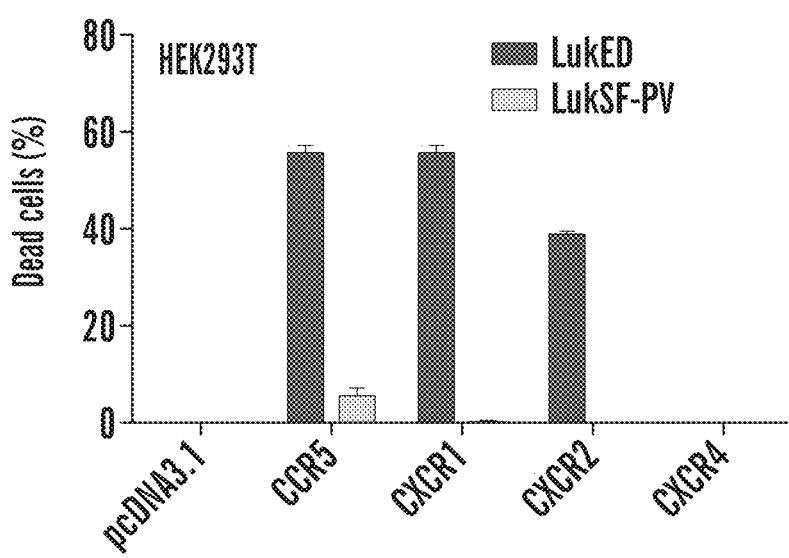
Figure 1G:
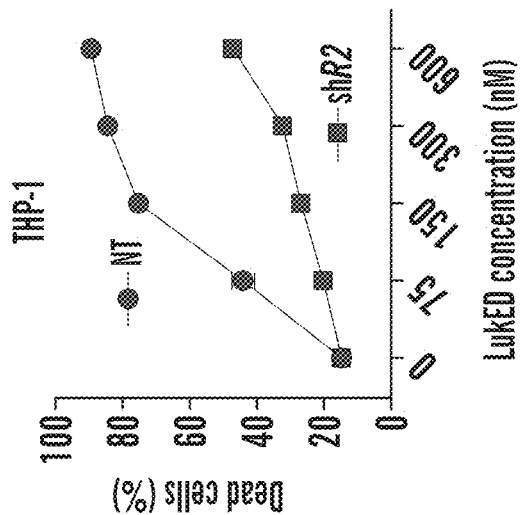
Figure 1F:
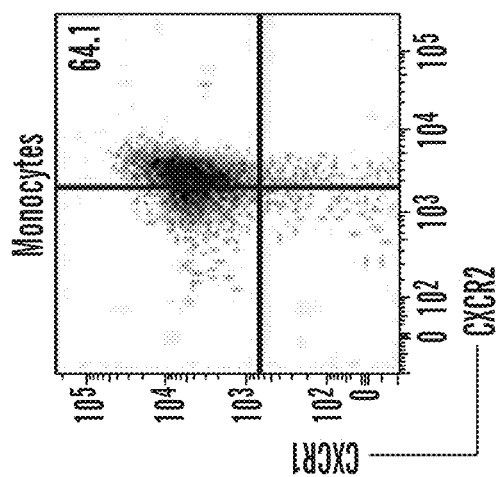
Figure 1E:
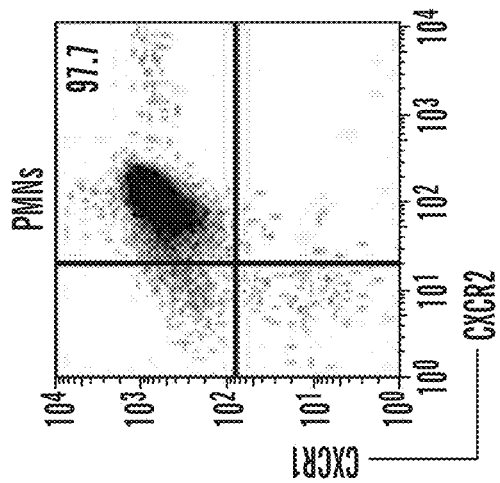

Consistent with their susceptibility to LukED, the majority of PMNs and peripheral blood monocytes were positive for both CXCR1 and/or CXCR2 (FIGS. 1E and 1F). Furthermore, lentiviral-based knockdown of CXCR2 with Cxcr2 shRNA in the human monocytic cell line THP-1, which displays only CXCR2 (Liu-Bryan et al., "The CXCR1 Tail Mediates Beta1 Integrin-Dependent Cell Migration Via MAP Kinase Signaling," Biochem. Biophys. Res. Commun. 332:117-125 (2005), which is hereby incorporated by reference in its entirety) (FIGS. 5B-5C), rendered cells resistant to LukED killing compared to non-target shRNA controls (FIG. 1G). These data demonstrate that CXCR1 or CXCR2 are necessary and sufficient for LukED-mediated killing of host cells.

Example 2—CXCR1, CXCR2, and DARC Also Render Cells Susceptible to HlgA

A common feature of the S. aureus leukotoxins is that they can all target and kill PMNs (Vandenesch et al., "Staphylococcus aureus Hemolysins, Bi-Component Leukocidins, and Cytolytic Peptides: A Redundant Arsenal of Membrane-Damaging Virulence Factors?" Front. Cell. Infect. Microbiol. 2:12 (2012) and Alonzo & Torres, "Bacterial Survival Amidst an Immune Onslaught: The Contribution of the Staphylococcus aureus Leukotoxins. PLoS Pathog. 9:e1003143 (2013), which are hereby incorporated by reference in their entirety). The findings described herein indicate that LukED kills PMNs by targeting CXCR1/CXCR2. Since LukED exhibits significant amino acid identity with LukSF-PV, HlgAB and HlgCB (more than 70%), whether these receptors also render host cells susceptible to these leukotoxins was also evaluated. CXCR1, CXCR2, and DARC, but not CCR5, rendered cells susceptible to HlgAB but not to HlgCB or LukSF-PV (FIGS. 4A-4B). The observation that HlgAB but not HlgCB targets these receptors indicates that HlgA is the subunit responsible for the tropism of this toxin. The finding that DARC supports HlgAB cytotoxicity is also in line with the observation that this toxin exhibits hemolytic activity.

Example 3—LukED Targets PMNs Via LukE Binding to CXCR1 and CXCR2

Figure 6A:
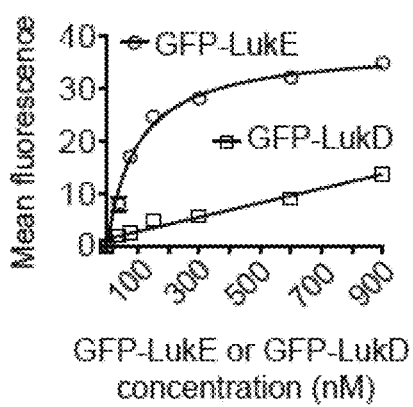
FIGS. 6A-6E demonstrate that LukED targets PMNs via LukE binding to CXCR1 and CXCR2.
Figure 6B:
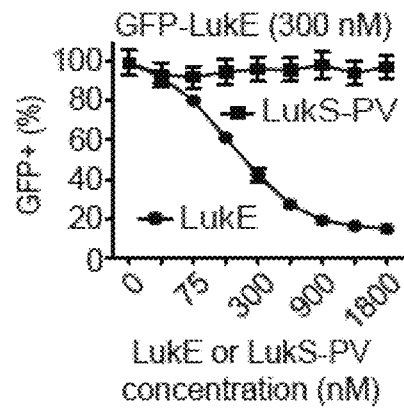

Because of their primary role in defense against S. aureus (Rigby & DeLeo, "Neutrophils in Innate Host Defense Against Staphylococcus aureus Infections," Semin. Immunopathol. 34:237-259 (2012), which is hereby incorporated by reference in its entirety), the remainder of the studies described herein focus on LukED-mediated targeting of CXCR1/CXCR2 on primary PMNs. A binding assay was employed where PMNs were incubated with green fluorescent protein-fused LukE or LukD (GFP-LukE or GFP-LukD) (Alonzo et al., "CCR5 is a Receptor for Staphylococcus aureus Leukotoxin ED," Nature 493:51-55 (2013), which is hereby incorporated by reference in its entirety). Only GFP-LukE bound to PMNs in a dose-dependent and saturable manner, while GFP-LukD displayed nonsaturable surface association (FIG. 6A). GFP-LukE binding was competed off with LukE but not the equivalent subunit of PVL, LukS-PV (FIG. 6B), suggesting specific interaction with CXCR1/CXCR2.

Figure 6C:
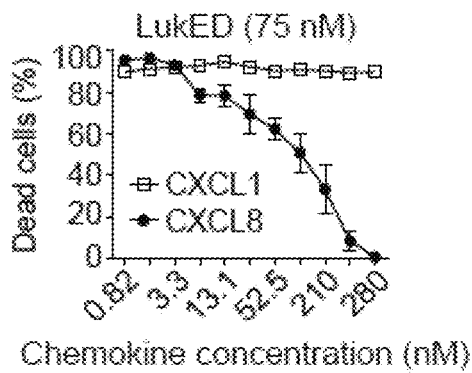
Figure 6D:
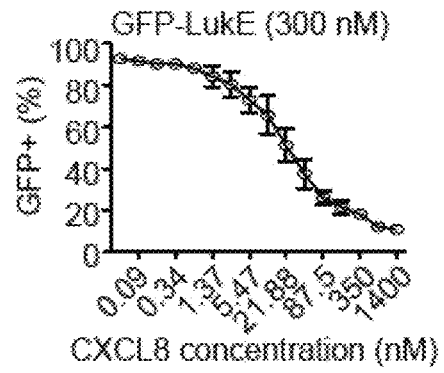
Figure 6E:
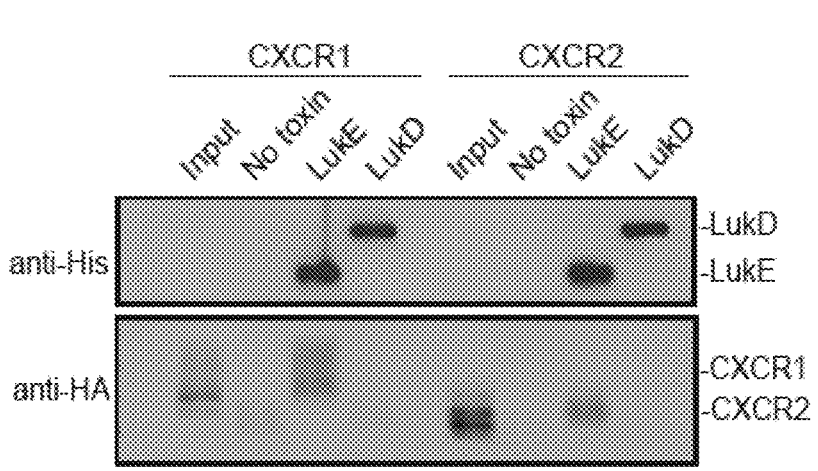
Figure 7:
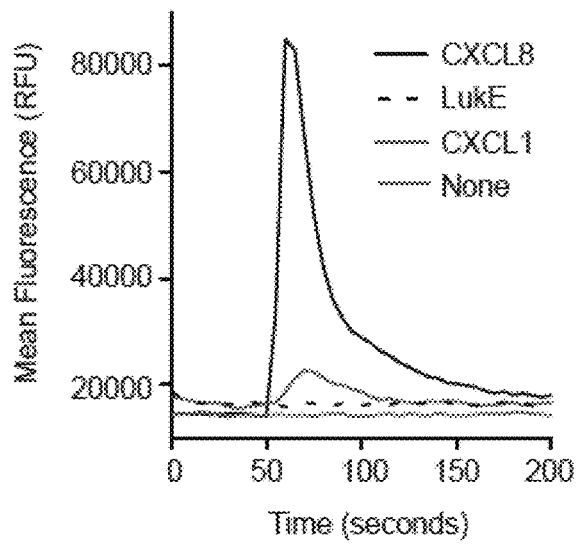
FIG. 7 shows that LukE does not activate calcium signaling on PMNs. The graph shows calcium mobilization on PMNs upon addition of LukE (300 nM), CXCL8 (0.3 nM) or CXCL1 (0.3 nM), measured by flow cytometry.

CXCR1/CXCR2 respond primarily to the chemokine ligand CXCL8, which is produced by the host in response to injury and infection (Nasser et al., "Differential Activation and Regulation of CXCR1 and CXCR2 by CXCL8 Monomer and Dimer," J. Immunol. 183:3425-3432 (2009); Stillie et al., "The Functional Significance Behind Expressing Two IL-8 Receptor Types on PMN," J. Leukoc. Biol. 86:529-543 (2009), which are hereby incorporated by reference in their entirety). In addition to CXCL8, CXCR2 also responds to the chemokine CXCL1 (Nasser et al., "Differential Activation and Regulation of CXCR1 and CXCR2 by CXCL8 Monomer and Dimer," J. Immunol. 183:3425-3432 (2009); Allen et al., "Chemokine: Receptor Structure, Interactions, and Antagonism," Annu. Rev. Immunol. 25:787-820 (2007), which are hereby incorporated by reference in their entirety). To test whether these chemokines are able to inhibit LukED mediated cytotoxicity, PMNs were treated with LukED in the presence of either CXCL8 or CXCL1. CXCL8 prevented LukED-mediated death of PMNs but not CXCL1 (FIG. 6C), indicating that blockade of both receptors is required to protect PMNs from LukED-mediated killing. CXCL8 protected PMNs from LukED by preventing LukE binding to the cell surface, a prerequisite for cytotoxicity (FIG. 6D). While LukE and CXCL8 both target CXCR1/CXCR2 they do not appear to engage the receptors to the same capacity, as LukE is unable to elicit calcium mobilization upon incubation with PMNs (FIG. 7). Consistent with the LukE-DPMN binding studies, pulldown experiments revealed that LukE but not LukD forms complexes with both CXCR1 and CXCR2 (FIG. 6E).

Figure 8:
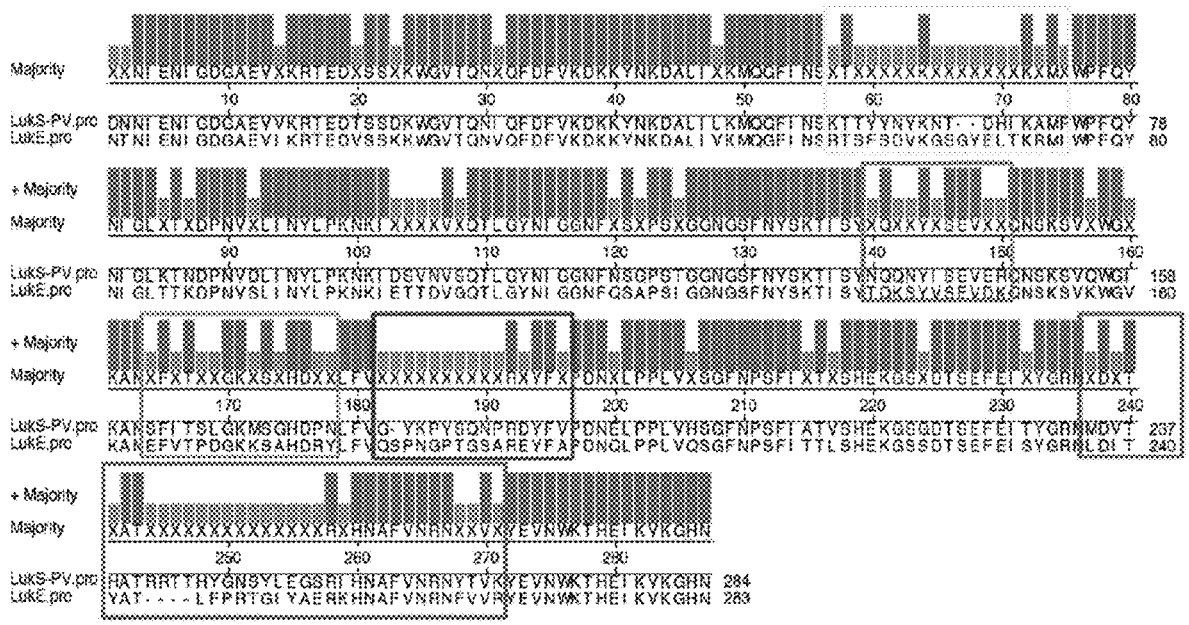
FIG. 8 is an amino acid sequence alignment of LukE and LukS-PV. Conserved amino acids are depicted in red (nonconserved amino acid residues are indicated with an X). Rim domain divergence regions ("DRs") are indicated as follows: DR1 (yellow box), DR2 (grey box), DR3 (orange box), DR4 (blue box) and DR5 (red box). Alignment was generated with DNASTAR MegAlign software using the ClustalW method.
Figure 9A:
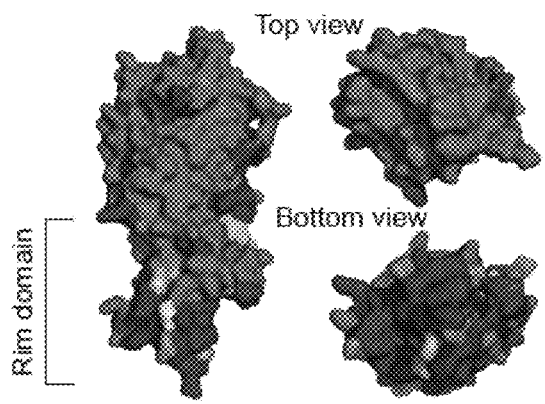
FIGS. 9A-9H demonstrate that LukE amino acid residues 182-196 in Divergence Region 4 are required for LukED targeting of CXCR1 and CXCR2+ cells.
Figure 9B:
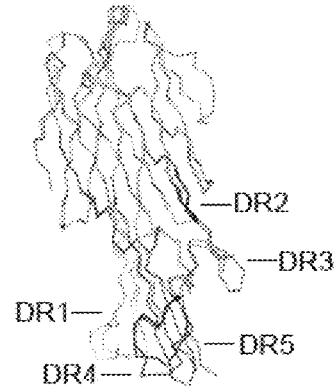
Figure 9C:
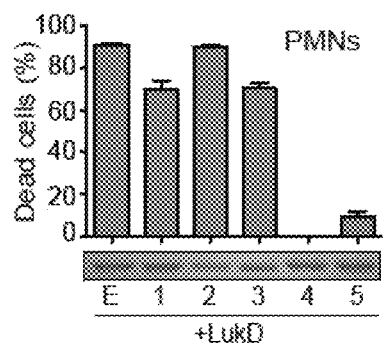

Example 4—LukE Amino Acid Residues 182-196 in Divergence Region 4 are Required for LukED Targeting of CXCR1 and CXCR2$^+$ Cells LukE and the highly homologous leukotoxin LukS-PV share 71% amino acid identity, yet LukS-PV does not use CXCR1/CXCR2 receptors to target and kill PMNs (Spaan et al., "The Staphylococcal Toxin Panton-Valentine Leukocidin Targets Human C5a Receptors," Cell Host & Microbe 13:584-594 (2013), which is hereby incorporated by reference in its entirety) (FIG. 1D). Amino acid sequence alignment of LukE and LukS-PV revealed five regions containing significant sequence divergence (divergence regions 1-5; DR1-5) (FIG. 8). These DRs are located primarily in the rim domain of the LukE and LukS-PV structures (FIG. 9A-9B), which have been hypothesized to play a role in receptor recognition (Menestrina et al., "Ion Channels and Bacterial Infection: The Case of Beta-Barrel Pore-Forming Protein Toxins of Staphylococcus aureus," FEBS Lett. 552:54-60 (2003), which is hereby incorporated by reference in its entirety). Hybrid LukE/S-PV toxins were generated to test whether any of these five DRs are involved in conferring specificity of LukE toward human PMNs. The LukE/S-PV hybrid proteins were purified, mixed at equimolar ratio with LukD, and incubated with PMNs to evaluate their cytotoxic activity. Only the LukE$^{DR4}$D and LukE$^{DR5}$D toxins were attenuated in their cytotoxicity towards PMNs compared to WT LukED (FIG. 9C).

Figure 9D:
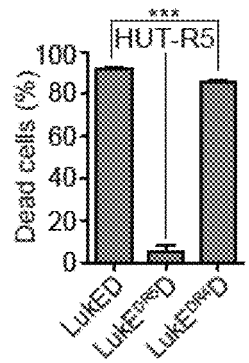
Figure 10:
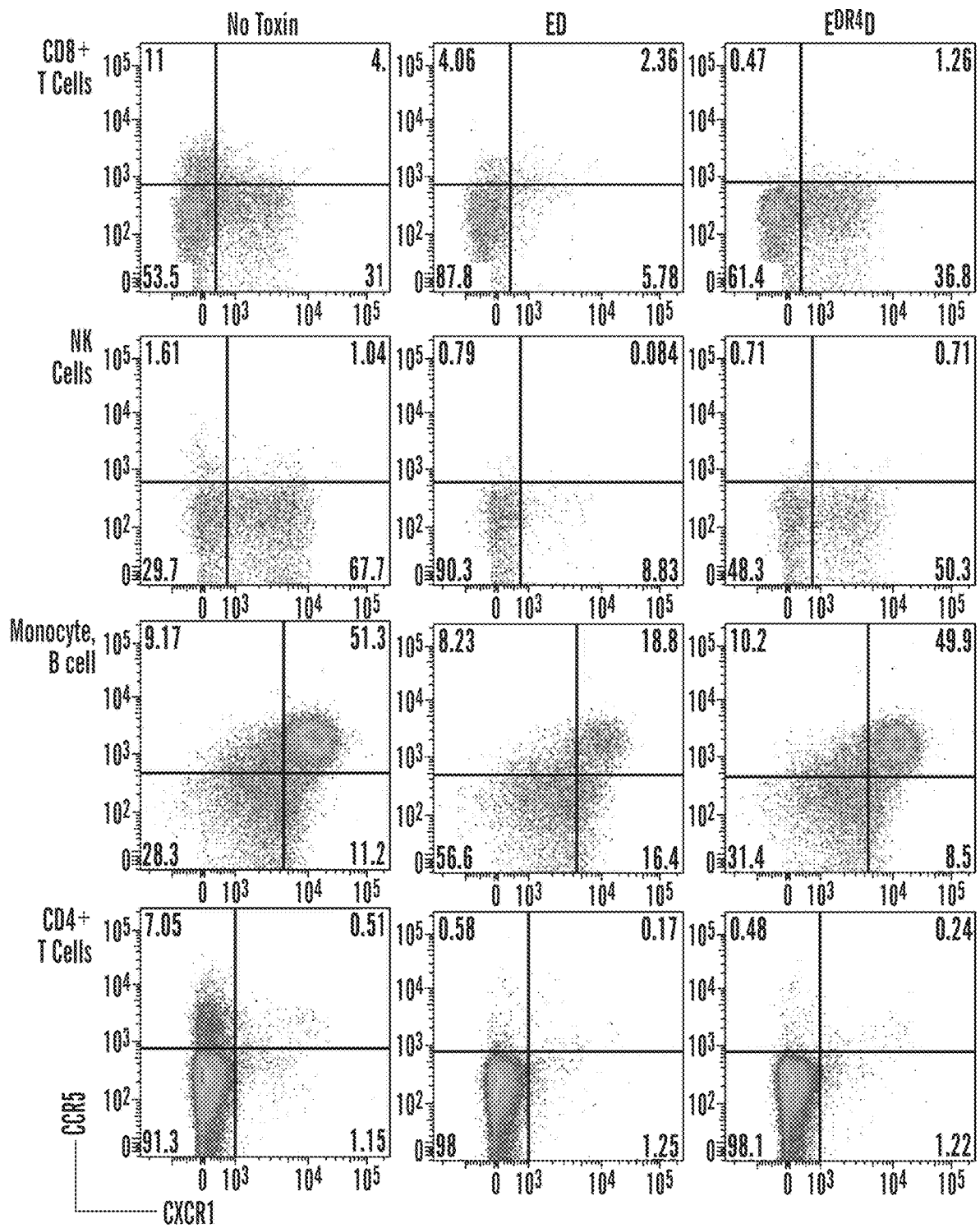
FIG. 10 shows the ex vivo and in vivo effects of LukED and LukE$^{DR4}$D. Susceptibility of PBMC subsets to treatment with No Toxin (PBS), LukED or LukE$^{DR4}$D was evaluated by flow cytometry.

To evaluate whether the lack of cytotoxicity exhibited by the LukE$^{DR4}$ and LukE$^{DR5}$ hybrids was specific towards CXCR1/CXCR2 expressing cells, their activity towards CCR5$^+$ cells was also tested. LukE$^{DR5}$D was also impaired in killing CCR5$^+$ cells as well, suggesting that DR5 is required for toxin activity rather than receptor targeting (FIG. 9C, 9D). Remarkably, LukE$^{DR4}$D was able to target CCR5$^+$ cells at similar potency to that of WT LukED, indicating that only DR4 is involved in CXCR1 and CXCR2 recognition (FIG. 9D). Further analysis of PBMCs revealed that LukED is also cytotoxic to the majority of NK cells and a subset of CD8$^+$ T cells, exclusively through CXCR1 expression (FIG. 10). In addition, LukE$^{DR4}$D mutant was reduced in its potency in killing monocytes despite their expression of CCR5 (FIG. 10), suggesting that CXCR1/CXCR2 may be the preferred receptors for LukED-mediated targeting of these myeloid lineage cells.

Figure 9E:
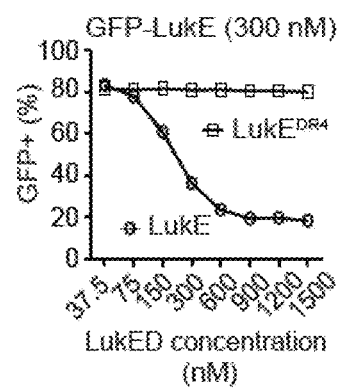
Figure 9F:
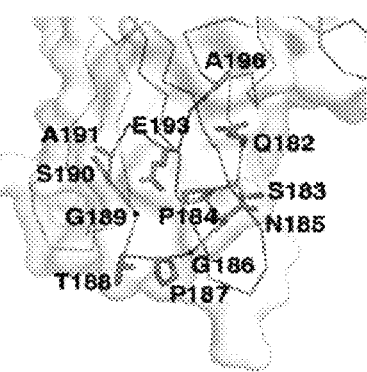

In contrast to wild type LukE, LukE$^{DR4}$ was unable to compete with GFP-LukE for binding to the plasma membrane of PMNs, validating the requirement of this domain for recognition of CXCR1/CXCR2$^+$ cells (FIG. 9E). The 15 amino acid sequence of LukE DR4 (residues 182-196) forms a loop containing two glycine residues (G186 and G189) and two proline residues (P184 and P187) that present a polar surface distinct from that of LukSPV, which could determine the tropism of LukE towards CXCR1/CXCR2.

Figure 9G:
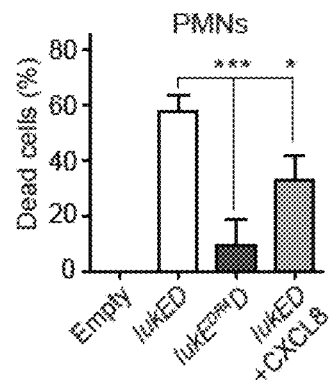
Figure 9H:
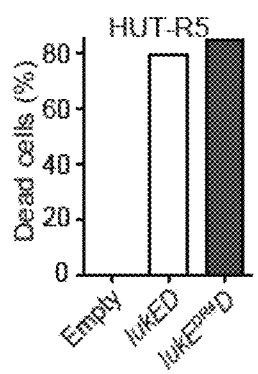
Figures 11A, 11B:
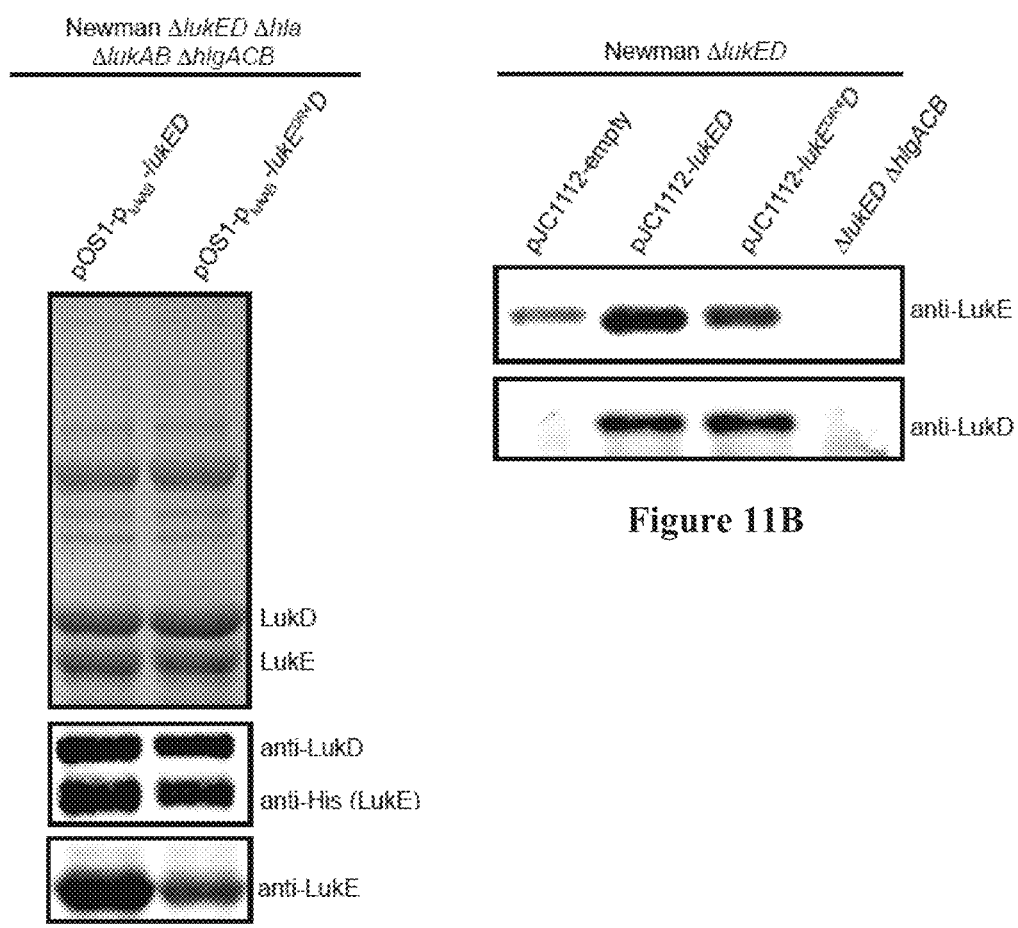
FIGS. 11A-11B show a protein analysis of different S. aureus strains. The top immunoblot of FIG. 11A shows an exoprotein profile of toxinless S. aureus strains complemented with plasmids encoding lukED or lukE$^{DR4}$D. The bottom two immunoblots of FIG. 11A assess the levels of LukD, LukE, LukE$^{DR4}$, and the presence of a His tag on the LukE constructs.

The contribution of CXCR1 and CXCR2 targeting by LukED to S. aureus-mediated killing of PMNs during ex vivo infection was also investigated. Since S. aureus produces an array of toxins capable of killing PMNs, a S. aureus strain lacking all the major toxins was engineered, where lukED or lukE$^{DR4}$D were expressed in trans from a plasmid (FIG. 11A). As expected, the toxinless S. aureus strain was unable to kill PMNs, whereas the toxinless strain complemented in trans with lukED was able to kill these cells (FIG. 9G). The cytotoxic activity of the LukED-producing S. aureus strain was inhibited by CXCL8 and the LukE$^{DR4}$D-producing strain exhibited significantly reduced PMN killing compared to the WT LukED-producing strain (FIG. 9G). Importantly, the defect in cell killing exhibited by the LukE$^{DR4}$D-producing strain was specific towards CXCR1/CXCR2$^+$ cells, as CCR5$^+$ cells were equally susceptible to both LukED and LukE$^{DR4}$D-producing strains (FIG. 9H).

Figure 12A:
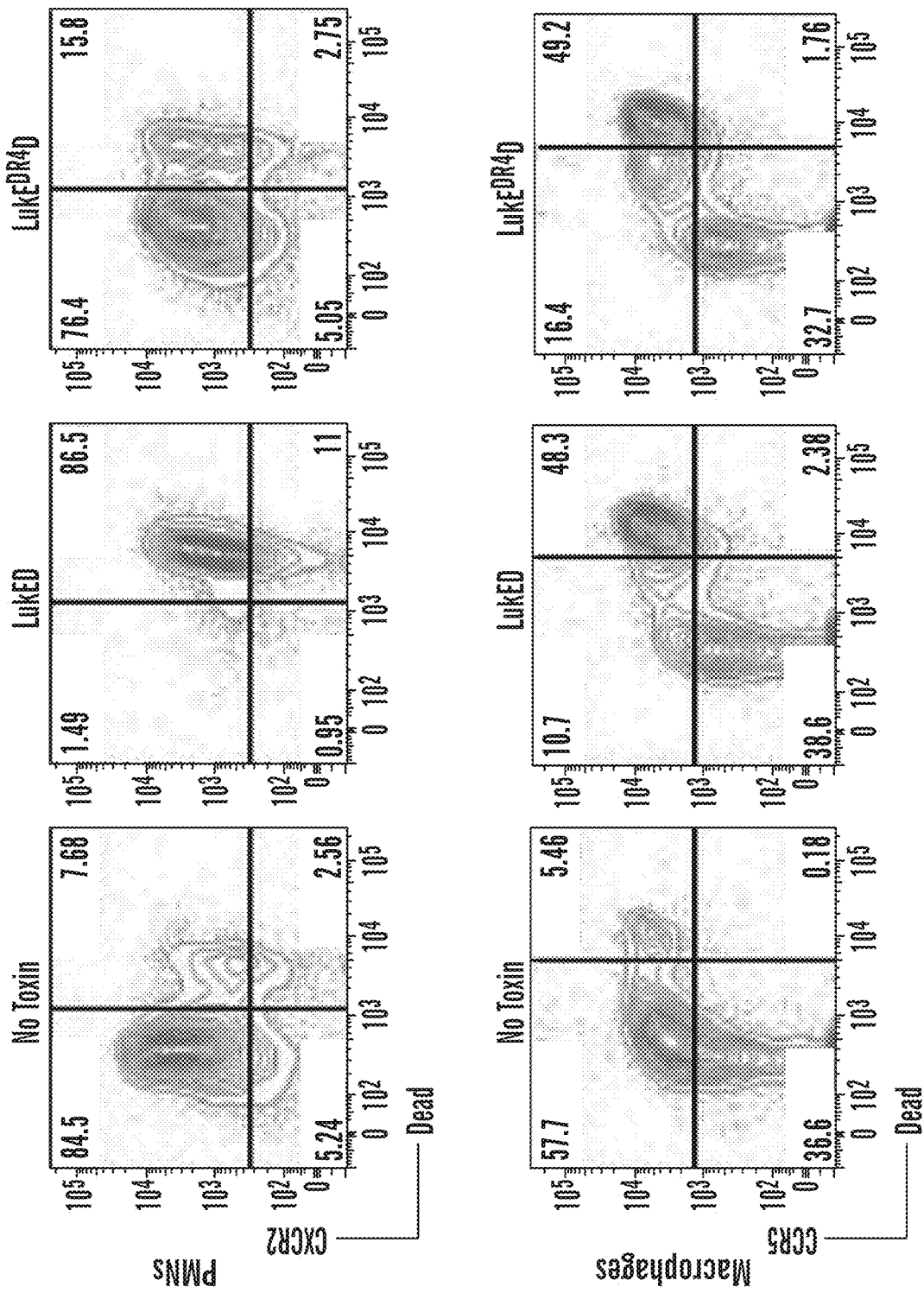
Figure 12B:
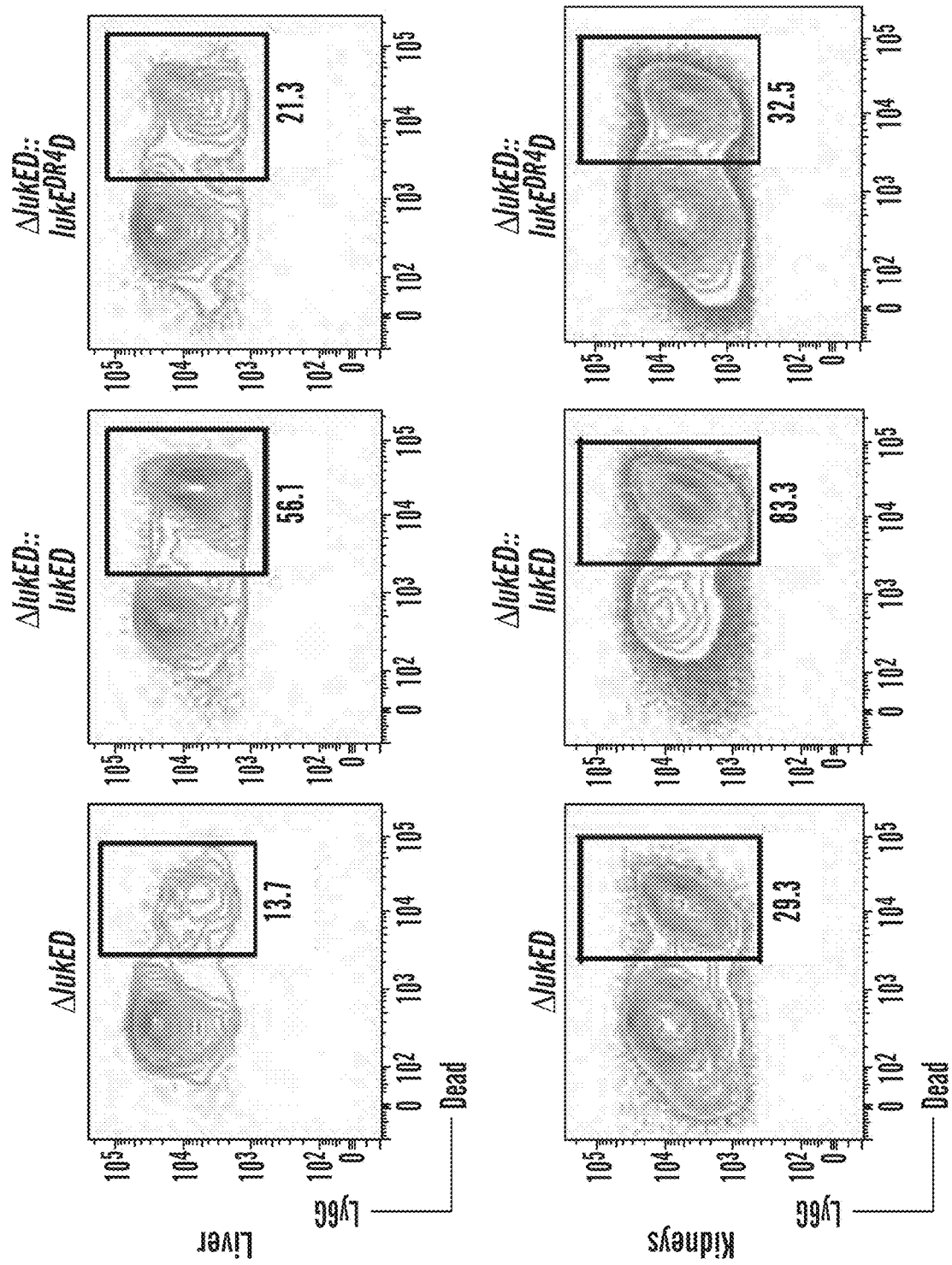

Example 5—LukED-Mediated Killing of CXCR1 and CXCR2+ Cells Contributes to S. aureus Pathogenesis in Mouse Models of Systemic Infection To evaluate if LukED also kills murine leukocytes in a CXCR1/CXCR2-dependent manner, murine peritoneal exudate cells (PEC) were treated with LukED or LukE$^{DR4}$D. While LukED killed ~79% of the PMNs, LukE$^{DR4}$D was significantly impaired and only killed ~8% of these cells. In contrast to the effects on PMNs, CCR5$^+$ macrophages from within the PEC population were equally susceptible to both LukED and LukE$^{DR4}$D (FIGS. 12A and 13A), consistent with the finding that LukED kills these cells in a strictly CCR5-dependent manner (Alonzo et al., "CCR5 is a Receptor for Staphylococcus aureus Leukotoxin ED," Nature 493:51-55 (2013), which is hereby incorporated by reference in its entirety). In addition, the viability PMNs from tissues infected with isogenic S. aureus ΔlukED, ΔlukED::lukED or ΔlukED::lukE$^{DR4}$D strains was assessed (FIG. 11). PMNs from S. aureus ΔlukED::lukE$^{DR4}$D-infected mice were largely protected, similar to ΔlukED infected mice, from toxin-mediated death compared to that of ΔlukED::lukED-infected mice. Notably, PMNs from ΔlukED::lukE$^{DR4}$D-infected mice were as healthy as PMNs from ΔlukED infected mice (FIGS. 12B and 13B), suggesting that the DR4 domain interaction with CXCR1/CXCR2 is required for PMN targeting in vivo.

LukED contributes to the mortality observed in mice suffering from S. aureus bloodstream infection (Alonzo et al., "Staphylococcus aureus Leucocidin ED Contributes to Systemic Infection by Targeting Neutrophils and Promoting Bacterial Growth in Vivo," Mol. Microbiol. 83:423-435 (2012); Alonzo et al., "CCR5 is a Receptor for Staphylococcus aureus Leukotoxin ED," Nature 493:51-55 (2013), which are hereby incorporated by reference in their entirety). To evaluate the role of LukED-mediated targeting of CXCR1/CXCR2 in conferring this phenotype, survival of animals infected systemically with isogenic S. aureus ΔlukED, ΔlukED::lukED, or ΔlukED::lukE$^{DR4}$D strains was monitored (FIG. 11i). As expected, mice infected with the ΔlukED strain survived the infection, while mice infected with the ΔlukED::lukED complemented strain succumbed (Alonzo et al., "CCR5 is a Receptor for Staphylococcus aureus Leukotoxin ED," Nature 493:51-55 (2013), which is hereby incorporated by reference in its entirety) to infection. In contrast, ΔlukED::lukE$^{DR4}$D-infected mice were markedly protected compared to the ΔlukED::lukED complemented strain (FIG. 12C). These findings suggest that LukED-mediated targeting of CXCR1 or CXCR2 promotes S. aureus pathogenesis in vivo.

The identification of CXCR1 and CXCR2 as LukED cellular receptors provides an explanation for the ability of this toxin to kill leukocytes that lack CCR5 (Alonzo et al., "CCR5 is a Receptor for Staphylococcus aureus Leukotoxin ED," Nature 493:51-55 (2013), which is hereby incorporated by reference in its entirety). Since PMNs are the first responders to infection and defects in PMN function result in extraordinary susceptibility to S. aureus infection (Rigby & DeLeo, "Neutrophils in Innate Host Defense Against Staphylococcus aureus Infections," Semin. Immunopathol. 34:237-259 (2012), which is hereby incorporated by reference in its entirety), it is logical that a pathogen like S. aureus would elaborate virulence factors such as LukED to kill these cells. However, the sustained function of PMNs is also dependent on their continuous recruitment and enhanced potency or lifespan through inflammatory mediators secreted at the sites of infection. Indeed, quantitative and qualitative disruption of either neutrophils or T cells, especially effector subsets that secrete IL-17 or IFNγ, greatly increase the susceptibility to S. aureus infection (Alonzo et al., "Staphylococcus aureus Leucocidin ED Contributes to Systemic Infection by Targeting Neutrophils and Promoting Bacterial Growth in Vivo," Mol. Microbiol. 83:423-435 (2012); Alonzo et al., "CCR5 is a Receptor for Staphylococcus aureus Leukotoxin ED," Nature 493:51-55 (2013); Cho et al., "IL-17 is Essential for Host Defense Against Cutaneous Staphylococcus aureus Infection in Mice," J. Clin. Invest. 120:1762-1773 (2010); Lin. et al., "Th1-Th17 Cells Mediate Protective Adaptive Immunity Against Staphylococcus aureus and Candida Albicans Infection in Mice," PLoS Pathog. 5:e1000703 (2009), which are hereby incorporated by reference in their entirety). As such, LukED uniquely targets both arms of the immune defense through its recognition of diverse host chemokine receptors. Through the use of CXCR1/CXCR2, LukED targets largely the innate defenses, neutrophils, monocytes, and NK cells. Whereas by targeting CCR5$^+$ cells, LukED eliminates T cell subsets (Th1 and Th17 cells), and professional antigen presenting cells (Alonzo et al., "CCR5 is a Receptor for Staphylococcus aureus Leukotoxin ED," Nature 493:51-55 (2013), which is hereby incorporated by reference in its entirety), all of which are critical in anti-Staph immunity. Due to the temporal nature of the host immune response and the diverse cell types involved in infection resolution, blockade of LukED targeting of either CXCR1/CXCR2 or CCR5 (Alonzo et al., "CCR5 is a Receptor for Staphylococcus aureus Leukotoxin ED," Nature 493:51-55 (2013), which is hereby incorporated by reference in its entirety) leads to enhanced survivability in vivo. Thus, the findings described herein suggest that strategies to block LukED would be an effective therapeutic or preventive approach against life-threatening S. aureus infection of humans.

Figure 14:
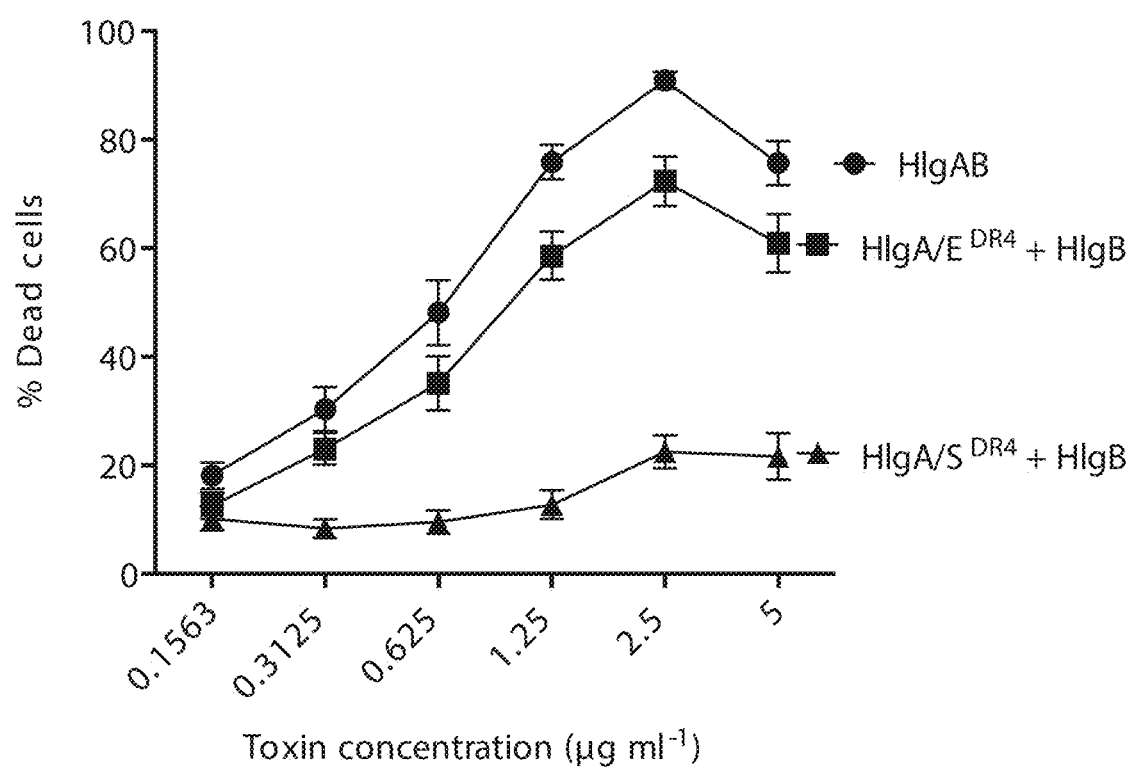
FIG. 14 demonstrates that HlgA amino acid residues 180-192 in Divergence Region 4 are required for HlgAB targeting human neutrophils (hPMNs), CXCR1/CXCR2+ cells. This figure shows the viability of hPMNs treated with WT and HlgA$^{DR}$ hybrid toxins. Cellular viability was monitored with CellTiter 96® AQueous One Solution Cell Proliferation Assay (Promega), Results represent the means and s.e.m. from different human donors (n=8).

Example 6—HlgA Amino Acid Residues 180-192 in Divergence Region 4 are Required for HlgAB Targeting Human Neutrophils (hPMNs), CXCR1/CXCR2+ Cells LukE and HlgA share more than 70% amino acid identity and both target the CXCR1 and CXCR2 receptors to kill hPMNs. To evaluate whether the amino acids in HlgA corresponding to the LukE DR4 domain (i.e., HlgA amino acids 180-192) are also involved in targeting CXCR1/CXCR2, several hybrid HlgA proteins were engineered. The HlgA DR4 domain was swapped with the LukE (HlgA$^{LukE-DR4}$) or LukS-PV (HlgA$^{LukS-DR4}$) DR4 domains. The HlgA$^{Luk-DR4}$ and HlgA$^{LkS-DR4}$ hybrid proteins were purified, mixed at equimolar ratio with HlgB, and incubated with hPMNs to evaluate their cytotoxic activity. HlgA amino acid residues 180-192 in Divergence Region 4 are required for HlgAB targeting human neutrophils (hPMNs), CXCR1/CXCR2+ cells (FIG. 14). The HlgA/HlgB and HlgA$^{LukE-DR4}$/HlgB combinations exhibited potent cytotoxic activity against hPMNs, but not the HlgA$^{LukS-DR4}$/HlgB combination. These data demonstrate that, as with LukED, HlgA's DR4 domain is involved in targeting CXCR1 and CXCR2.

Example 7—LukE's Amino Acids P184, G186, P187, and G189 within the DR4 Domain are Required for Targeting and Killing hPMNs and for LukED-Mediated Lethality Upon Bloodstream Intoxication It was demonstrated that LukE binds to CXCR1/CXCR2+ cells via the DR4 domain and that switching this domain with the LukS-PV DR4 renders LukED inactive towards CXCR1/CXCR2+ cells including human neutrophils (FIGS. 9A-9H). The DR4 domain in HlgA was also found to be required for HlgAB targeting and killing of human neutrophils (FIG. 14). The LukE DR4 forms a loop containing two glycine residues (G186 and G189) and two proline residues (P184 and P187) that present a polar surface sufficiently distinct from that of LukS-PV's DR4, which likely determines the tropism of LukE toward CXCR1 and CXCR2. Interestingly, three out of these four amino acids are also conserved in HlgA. To directly evaluate the involvement of P184, G186, P187, and G189 in LukED-mediated killing of hPMNs, all four amino acids were mutated to alanine resulting in the LukE$^{P184A,G186A,P187A,G189A}$ protein (LukE$^{P184,G186,P187}$). The WT LukE and the LukE$^{P184,G186,P187,G189}$ proteins were purified, mixed at equimolar ratio with LukD, and incubated with human hPMNs to evaluate their cytotoxic activity. While the WT LukED toxin targeted and killed the hPMNs, no detectable activity was observed for the LukE$^{P184,G186,P187,G189}$/LukD toxin (FIG. 15A). This data demonstrates the importance of the polar surface created by the P184, G186, P187, and G189 amino acids for LukED-mediated killing of CXCR1/CXCR2+ cells. It is predicted that the HlgA residues corresponding to LukE P184, G186, and P187 play a similar role in HlgA's binding to CXCR1/CXCR2.

LukED is a leukotoxin involved in the lethality observed in mice infected intravenously with *S. aureus* (Alonzo et al., "*Staphylococcus aureus* Leucocidin ED Contributes to Systemic Infection by Targeting Neutrophils and Promoting Bacterial Growth In Vivo," *Mol. Microbiol.* 83(2):423-35 (2012); Alonzo et al., "CCR5 Is a Receptor for *Staphylococcus aureus* Leukotoxin ED," *Nature* 493(7430):51-5 (2013); Reyes-Robles et al., "*Staphylococcus aureus* Leukotoxin ED Targets the Chemokine Receptors CXCR1 and CXCR2 to Kill Leukocytes and Promote Infection," *Cell Host Microbe.* 14(4):453-9 (2013), each of which is hereby incorporated by reference in its entirety). To further study the direct effects of this toxin in vivo, mice were intravenously injected with purified LukED. It was observed that administration of the WT toxin at concentrations higher that 10 g of each submit into a 20 g mouse resulted in the rapid death of the "intoxicated" animal (FIG. 15B). To examine the contribution of CXCR1/CXCR2 targeting to this LukED-mediated lethality, the in vivo effects of the LukE$^{LukS-DR4}$/LukD and the LukE$^{P184,G186,P187,G189}$/LukD toxins were also tested. Consistent with the importance of CXCR1/CXCR2 targeting by LukED to the lethality observed with *S. aureus* bloodstream infection (Reyes-Robles et al., "*Staphylococcus aureus* Leukotoxin ED Targets the Chemokine Receptors CXCR1 and CXCR2 to Kill Leukocytes and Promote Infection," *Cell Host Microbe.* 14(4):453-9 (2013), which is hereby incorporated by reference in its entirety), mutations that impaired LukED targeting of CXCR1/CXCR2+ cells eliminated the lethal effect of the toxin (FIG. 15B).

Figure 3:
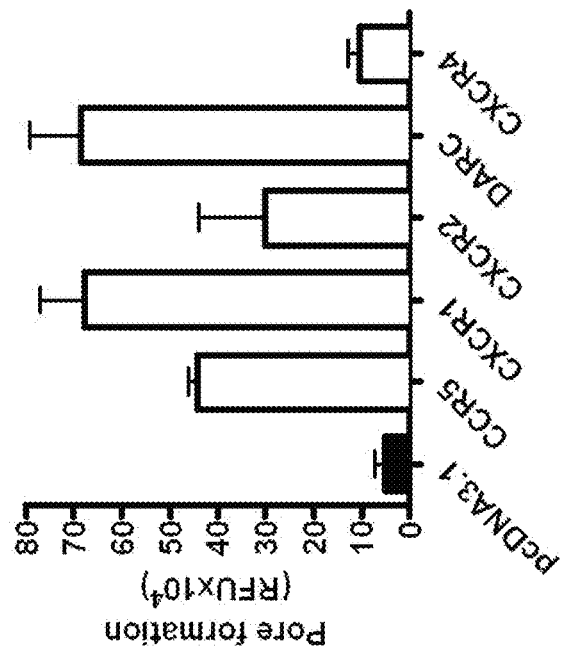
FIG. 3 demonstrates that LukED targets CCR5, CXCR1, CXCR2, and DARC to kill host cells. HEK293T cells were transfected with empty plasmid (pcDNA), or with plasmids containing cDNAs encoding the indicated chemokine receptors. Cells were then exposed to LukED for 1 hr and toxin-mediated pores measured by ethidium bromide permeability.
Figure 16A:
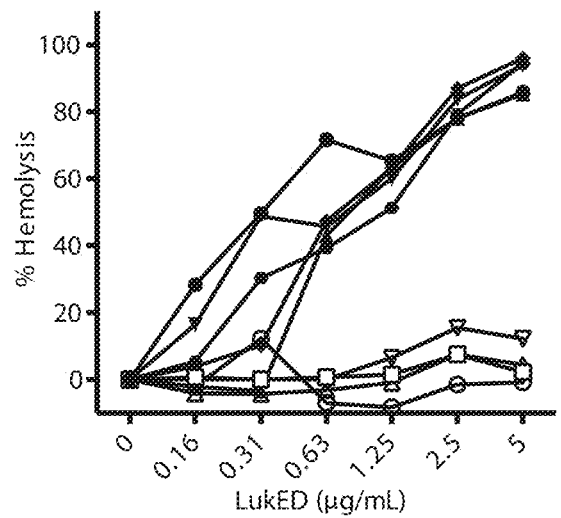
FIGS. 16A-16D demonstrate that LukED-mediated lysis of human red blood cells (RBCs) is associated with the presence of DARC and that LukED-mediated lysis of RBCs could be blocked with purified DARC and an anti-DARC antibody.
Figure 16B:
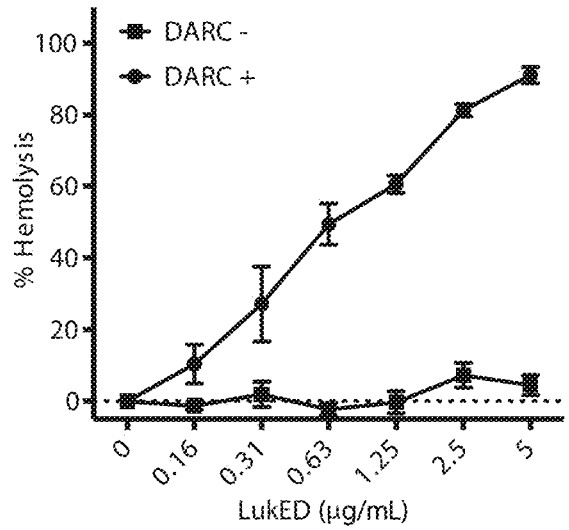

Example 8—LukED-Mediated Lysis of Human Red Blood Cells is Dependent on DARC and could be Blocked with Purified DARC and Anti-DARC Antibodies Transfection of HEK293T cells with DARC-expressing plasmids is sufficient to render these cells susceptible to LukED and HlgAB (FIGS. 3 and 4A). While testing the hemolytic activity of LukED towards human red blood cells (RBCs), it was observed that some donors were susceptible to LukED hemolysis while others were not (FIGS. 16A and 16B). Evaluation of the levels of DARC on the surface of RBCs by fluorescence-activated cell sorting (FACS) revealed that the resistance towards LukED was linked to no detectable DARC on the surface of these RBCs, suggesting that DARC is required for LukED-mediated lysis of RBCs.

Figure 16C:
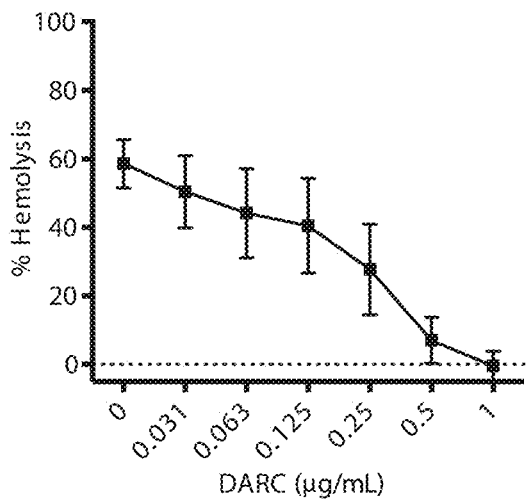
Figure 16D:
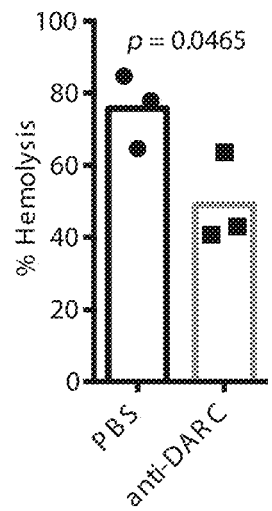

Lysis of RBCs have been hypothesized to be required for the pathogenesis of *S. aureus*, due to the release of hemoglobin, a rich source of iron, a critical metal for *S. aureus* growth. Thus, blocking the ability of *S. aureus* to lyse RBCs will inhibit the release of hemoglobin diminishing bacterial growth. The identification of DARC as a cellular factor required for LukED- and HlgAB-mediated hemolysis suggest that blocking the toxin-receptor interaction is likely to protect RBCs from these toxins. To test this hypothesis, LukED was incubated with buffer or with increasing concentrations of purified DARC (OriGene Technologies Inc.) prior to incubation with human RBCs. DARC was found to be able to fully neutralize LukED-mediated lysis of RBCs (FIG. 16C). Moreover, treatment of human RBCs with an anti-human DARC monoclonal antibody (clone #358307; R&D Systems™) also protected human RBCs from LukED-mediated lysis (FIG. 16D). Altogether, these findings demonstrate that human RBCs could be protected from LukED, and most likely HlgAB-mediated lysis of human RBCs by purified DARC or antibodies directed against this receptor.

Although the invention has been described in detail for the purposes of illustration, it is understood that such detail is solely for that purpose, and variations can be made therein by those skilled in the art without departing from the spirit and scope of the invention which is defined by the following claims.

What is claimed:

1. A variant Leukocidin E (LukE) protein or polypeptide thereof of SEQ ID NO:4, said variant LukE protein or polypeptide comprising the amino acid sequence of residues 57-75 and 139-150 of SEQ ID NO: 4, and comprising one or more changes to the amino acid sequence of each of (i) residues 164-178 of SEQ ID NO: 4, (ii) residues 182-196 of SEQ ID NO: 4, and (iii) residues 237-271 of SEQ ID NO: 4.

2. The variant LukE polypeptide of claim 1, wherein said LukE polypeptide is between 50 to 100 amino acid residues in length.

3. The variant LukE polypeptide of claim 1, wherein said LukE polypeptide is between 100 to 200 amino acid residues in length.

4. The variant LukE polypeptide of claim 1, wherein said LukE polypeptide is between 200 to 250 amino acid residues in length.

5. A composition comprising:
   the variant LukE protein or polypeptide of claim 1; and
   a pharmaceutically acceptable carrier.

6. The composition of claim 4 further comprising:
   a Leukocidin D (LukD) protein or polypeptide.

7. The composition of claim 5, wherein the LukD protein comprises an amino acid sequence of SEQ ID NO:12 or an amino acid sequence having at least 70% sequence similarity to SEQ ID NO:12.

* * * * *

SEQUENCE LISTING

<160> NUMBER OF SEQ ID NOS: 58

<210> SEQ ID NO 1
<211> LENGTH: 72
<212> TYPE: PRT
<213> ORGANISM: artificial
<220> FEATURE:
<223> OTHER INFORMATION: CXCL8(3-74)K11R/G31P

<400> SEQUENCE: 1

Thr Glu Leu Arg Cys Gln Cys Ile Arg Thr His Ser Thr Pro Phe His
1               5                   10                  15

Pro Lys Phe Ile Lys Glu Leu Arg Val Ile Glu Ser Pro Pro His Cys
            20                  25                  30

Glu Asn Ser Glu Ile Ile Val Lys Leu Thr Asn Gly Asn Glu Val Cys
        35                  40                  45

Leu Asn Pro Lys Glu Lys Trp Val Gln Lys Val Val Gln Val Phe Val
    50                  55                  60

Lys Arg Ala Glu Lys Gln Asp Pro
65                  70

<210> SEQ ID NO 2
<211> LENGTH: 72
<212> TYPE: PRT
<213> ORGANISM: artificial
<220> FEATURE:
<223> OTHER INFORMATION: CXCL8(3-74)K11R/G31P/P32G

<400> SEQUENCE: 2

Thr Glu Leu Arg Cys Gln Cys Ile Arg Thr His Ser Thr Pro Phe His
1               5                   10                  15

Pro Lys Phe Ile Lys Glu Leu Arg Val Ile Glu Ser Gly Gly His Cys
            20                  25                  30

Glu Asn Ser Glu Ile Ile Val Lys Leu Thr Asn Gly Asn Glu Val Cys
        35                  40                  45

Leu Asn Pro Lys Glu Lys Trp Val Gln Lys Val Val Gln Val Phe Val
    50                  55                  60

Lys Arg Ala Glu Lys Gln Asp Pro
65                  70

<210> SEQ ID NO 3
<211> LENGTH: 72
<212> TYPE: PRT
<213> ORGANISM: artificial
<220> FEATURE:
<223> OTHER INFORMATION: CXCL8(3-74)K11R/T12S/H13F/G31P

<400> SEQUENCE: 3

Thr Glu Leu Arg Cys Gln Cys Ile Arg Ser Pro Ser Thr Pro Phe His
1               5                   10                  15

Pro Lys Phe Ile Lys Glu Leu Arg Val Ile Glu Ser Pro Pro His Cys
            20                  25                  30

Glu Asn Ser Glu Ile Ile Val Lys Leu Thr Asn Gly Asn Glu Val Cys
        35                  40                  45

Leu Asn Pro Lys Glu Lys Trp Val Gln Lys Val Val Gln Val Phe Val
    50                  55                  60

Lys Arg Ala Glu Lys Gln Asp Pro
65                  70

```
<210> SEQ ID NO 4
<211> LENGTH: 283
<212> TYPE: PRT
<213> ORGANISM: Staphylococcus aureus

<400> SEQUENCE: 4
```

| | | | | | | | | | | | | | | |
|---|---|---|---|---|---|---|---|---|---|---|---|---|---|---|
| Asn | Thr | Asn | Ile | Glu | Asn | Ile | Gly | Asp | Gly | Ala | Glu | Val | Ile | Lys | Arg |
| 1 | | | | 5 | | | | | 10 | | | | | 15 | |
| Thr | Glu | Asp | Val | Ser | Ser | Lys | Lys | Trp | Gly | Val | Thr | Gln | Asn | Val | Gln |
| | | | 20 | | | | | 25 | | | | | 30 | | |
| Phe | Asp | Phe | Val | Lys | Asp | Lys | Lys | Tyr | Asn | Lys | Asp | Ala | Leu | Ile | Val |
| | | | 35 | | | | | 40 | | | | | 45 | | |
| Lys | Met | Gln | Gly | Phe | Ile | Asn | Ser | Arg | Thr | Ser | Phe | Ser | Asp | Val | Lys |
| | 50 | | | | | 55 | | | | | 60 | | | | |
| Gly | Ser | Gly | Tyr | Glu | Leu | Thr | Lys | Arg | Met | Ile | Trp | Pro | Phe | Gln | Tyr |
| 65 | | | | | 70 | | | | | 75 | | | | | 80 |
| Asn | Ile | Gly | Leu | Thr | Thr | Lys | Asp | Pro | Asn | Val | Ser | Leu | Ile | Asn | Tyr |
| | | | | 85 | | | | | 90 | | | | | 95 | |
| Leu | Pro | Lys | Asn | Lys | Ile | Glu | Thr | Thr | Asp | Val | Gly | Gln | Thr | Leu | Gly |
| | | | 100 | | | | | 105 | | | | | 110 | | |
| Tyr | Asn | Ile | Gly | Gly | Asn | Phe | Gln | Ser | Ala | Pro | Ser | Ile | Gly | Gly | Asn |
| | | | 115 | | | | | 120 | | | | | 125 | | |
| Gly | Ser | Phe | Asn | Tyr | Ser | Lys | Thr | Ile | Ser | Tyr | Thr | Gln | Lys | Ser | Tyr |
| | 130 | | | | | 135 | | | | | 140 | | | | |
| Val | Ser | Glu | Val | Asp | Lys | Gln | Asn | Ser | Lys | Ser | Val | Lys | Trp | Gly | Val |
| 145 | | | | | 150 | | | | | 155 | | | | | 160 |
| Lys | Ala | Asn | Glu | Phe | Val | Thr | Pro | Asp | Gly | Lys | Lys | Ser | Ala | His | Asp |
| | | | | 165 | | | | | 170 | | | | | 175 | |
| Arg | Tyr | Leu | Phe | Val | Gln | Ser | Pro | Asn | Gly | Pro | Thr | Gly | Ser | Ala | Arg |
| | | | 180 | | | | | 185 | | | | | 190 | | |
| Glu | Tyr | Phe | Ala | Pro | Asp | Asn | Gln | Leu | Pro | Pro | Leu | Val | Gln | Ser | Gly |
| | | | 195 | | | | | 200 | | | | | 205 | | |
| Phe | Asn | Pro | Ser | Phe | Ile | Thr | Thr | Leu | Ser | His | Glu | Lys | Gly | Ser | Ser |
| | 210 | | | | | 215 | | | | | 220 | | | | |
| Asp | Thr | Ser | Glu | Phe | Glu | Ile | Ser | Tyr | Gly | Arg | Asn | Leu | Asp | Ile | Thr |
| 225 | | | | | 230 | | | | | 235 | | | | | 240 |
| Tyr | Ala | Thr | Leu | Phe | Pro | Arg | Thr | Gly | Ile | Tyr | Ala | Glu | Arg | Lys | His |
| | | | | 245 | | | | | 250 | | | | | 255 | |
| Asn | Ala | Phe | Val | Asn | Arg | Asn | Phe | Val | Val | Arg | Tyr | Glu | Val | Asn | Trp |
| | | | 260 | | | | | 265 | | | | | 270 | | |
| Lys | Thr | His | Glu | Ile | Lys | Val | Lys | Gly | His | Asn | | | | | |
| | | | 275 | | | | | 280 | | | | | | | |

```
<210> SEQ ID NO 5
<211> LENGTH: 15
<212> TYPE: PRT
<213> ORGANISM: Staphylococcus aureus

<400> SEQUENCE: 5
```

| | | | | | | | | | | | | | | |
|---|---|---|---|---|---|---|---|---|---|---|---|---|---|---|
| Gln | Ser | Pro | Asn | Gly | Pro | Thr | Gly | Ser | Ala | Arg | Glu | Tyr | Phe | Ala |
| 1 | | | | 5 | | | | | 10 | | | | | 15 |

```
<210> SEQ ID NO 6
<211> LENGTH: 280
<212> TYPE: PRT
<213> ORGANISM: Staphylococcus aureus
```

<400> SEQUENCE: 6

```
Glu Asn Lys Ile Glu Asp Ile Gly Gln Gly Ala Glu Ile Ile Lys Arg
1               5                   10                  15

Thr Gln Asp Ile Thr Ser Lys Arg Leu Ala Ile Thr Gln Asn Ile Gln
            20                  25                  30

Phe Asp Phe Val Lys Asp Lys Lys Tyr Asn Lys Asp Ala Leu Val Val
        35                  40                  45

Lys Met Gln Gly Phe Ile Ser Ser Arg Thr Thr Tyr Ser Asp Leu Lys
50                  55                  60

Lys Tyr Pro Tyr Ile Lys Arg Met Ile Trp Pro Phe Gln Tyr Asn Ile
65                  70                  75                  80

Ser Leu Lys Thr Lys Asp Ser Asn Val Asp Leu Ile Asn Tyr Leu Pro
                85                  90                  95

Lys Asn Lys Ile Asp Ser Ala Asp Val Ser Gln Lys Leu Gly Tyr Asn
            100                 105                 110

Ile Gly Gly Asn Phe Gln Ser Ala Pro Ser Ile Gly Gly Ser Gly Ser
        115                 120                 125

Phe Asn Tyr Ser Lys Thr Ile Ser Tyr Asn Gln Lys Asn Tyr Val Thr
    130                 135                 140

Glu Val Glu Ser Gln Asn Ser Lys Gly Val Lys Trp Gly Val Lys Ala
145                 150                 155                 160

Asn Ser Phe Val Thr Pro Asn Gly Gln Val Ser Ala Tyr Asp Gln Tyr
                165                 170                 175

Leu Phe Ala Gln Asp Pro Thr Gly Pro Ala Ala Arg Asp Tyr Phe Val
            180                 185                 190

Pro Asp Asn Gln Leu Pro Pro Leu Ile Gln Ser Gly Phe Asn Pro Ser
        195                 200                 205

Phe Ile Thr Thr Leu Ser His Glu Arg Gly Lys Gly Asp Lys Ser Glu
    210                 215                 220

Phe Glu Ile Thr Tyr Gly Arg Asn Met Asp Ala Thr Tyr Ala Tyr Val
225                 230                 235                 240

Thr Arg His Arg Leu Ala Val Asp Arg Lys His Asp Ala Phe Lys Asn
                245                 250                 255

Arg Asn Val Thr Val Lys Tyr Glu Val Asn Trp Lys Thr His Glu Val
            260                 265                 270

Lys Ile Lys Ser Ile Thr Pro Lys
        275                 280
```

<210> SEQ ID NO 7
<211> LENGTH: 13
<212> TYPE: PRT
<213> ORGANISM: Staphylococcus aureus

<400> SEQUENCE: 7

```
Gln Asp Pro Thr Gly Pro Ala Ala Arg Asp Tyr Phe Val
1               5                   10
```

<210> SEQ ID NO 8
<211> LENGTH: 282
<212> TYPE: PRT
<213> ORGANISM: artificial
<220> FEATURE:
<223> OTHER INFORMATION: LukELukS-DR4

-continued

<400> SEQUENCE: 8

```
Asn Thr Asn Ile Glu Asn Ile Gly Asp Gly Ala Glu Val Ile Lys Arg
1               5                   10                  15

Thr Glu Asp Val Ser Ser Lys Lys Trp Gly Val Thr Gln Asn Val Gln
            20                  25                  30

Phe Asp Phe Val Lys Asp Lys Lys Tyr Asn Lys Asp Ala Leu Ile Val
        35                  40                  45

Lys Met Gln Gly Phe Ile Asn Ser Arg Thr Ser Phe Ser Asp Val Lys
50                  55                  60

Gly Ser Gly Tyr Glu Leu Thr Lys Arg Met Ile Trp Pro Phe Gln Tyr
65                  70                  75                  80

Asn Ile Gly Leu Thr Thr Lys Asp Pro Asn Val Ser Leu Ile Asn Tyr
                85                  90                  95

Leu Pro Lys Asn Lys Ile Glu Thr Thr Asp Val Gly Gln Thr Leu Gly
            100                 105                 110

Tyr Asn Ile Gly Gly Asn Phe Gln Ser Ala Pro Ser Ile Gly Gly Asn
        115                 120                 125

Gly Ser Phe Asn Tyr Ser Lys Thr Ile Ser Tyr Thr Gln Lys Ser Tyr
130                 135                 140

Val Ser Glu Val Asp Lys Gln Asn Ser Lys Ser Val Lys Trp Gly Val
145                 150                 155                 160

Lys Ala Asn Glu Phe Val Thr Pro Asp Gly Lys Lys Ser Ala His Asp
                165                 170                 175

Arg Tyr Leu Phe Val Gly Tyr Lys Pro Tyr Ser Gln Asn Pro Arg Asp
            180                 185                 190

Tyr Phe Val Pro Asp Asn Gln Leu Pro Pro Leu Val Gln Ser Gly Phe
        195                 200                 205

Asn Pro Ser Phe Ile Thr Thr Leu Ser His Glu Lys Gly Ser Ser Asp
210                 215                 220

Thr Ser Glu Phe Glu Ile Ser Tyr Gly Arg Asn Leu Asp Ile Thr Tyr
225                 230                 235                 240

Ala Thr Leu Phe Pro Arg Thr Gly Ile Tyr Ala Glu Arg Lys His Asn
                245                 250                 255

Ala Phe Val Asn Arg Asn Phe Val Val Arg Tyr Glu Val Asn Trp Lys
            260                 265                 270

Thr His Glu Ile Lys Val Lys Gly His Asn
        275                 280
```

<210> SEQ ID NO 9
<211> LENGTH: 243
<212> TYPE: PRT
<213> ORGANISM: artificial
<220> FEATURE:
<223> OTHER INFORMATION: LukE20-263 LukS-DR4

<400> SEQUENCE: 9

```
Val Ser Ser Lys Lys Trp Gly Val Thr Gln Asn Val Gln Phe Asp Phe
1               5                   10                  15

Val Lys Asp Lys Lys Tyr Asn Lys Asp Ala Leu Ile Val Lys Met Gln
            20                  25                  30

Gly Phe Ile Asn Ser Arg Thr Ser Phe Ser Asp Val Lys Gly Ser Gly
        35                  40                  45

Tyr Glu Leu Thr Lys Arg Met Ile Trp Pro Phe Gln Tyr Asn Ile Gly
    50                  55                  60
```

```
Leu Thr Thr Lys Asp Pro Asn Val Ser Leu Ile Asn Tyr Leu Pro Lys
 65                  70                  75                  80

Asn Lys Ile Glu Thr Thr Asp Val Gly Gln Thr Leu Gly Tyr Asn Ile
                 85                  90                  95

Gly Gly Asn Phe Gln Ser Ala Pro Ser Ile Gly Gly Asn Gly Ser Phe
            100                 105                 110

Asn Tyr Ser Lys Thr Ile Ser Tyr Thr Gln Lys Ser Tyr Val Ser Glu
        115                 120                 125

Val Asp Lys Gln Asn Ser Lys Ser Val Lys Trp Gly Val Lys Ala Asn
    130                 135                 140

Glu Phe Val Thr Pro Asp Gly Lys Lys Ser Ala His Asp Arg Tyr Leu
145                 150                 155                 160

Phe Val Gly Tyr Lys Pro Tyr Ser Gln Asn Pro Arg Asp Tyr Phe Val
                165                 170                 175

Pro Asp Asn Gln Leu Pro Pro Leu Val Gln Ser Gly Phe Asn Pro Ser
            180                 185                 190

Phe Ile Thr Thr Leu Ser His Glu Lys Gly Ser Ser Asp Thr Ser Glu
        195                 200                 205

Phe Glu Ile Ser Tyr Gly Arg Asn Leu Asp Ile Thr Tyr Ala Thr Leu
    210                 215                 220

Phe Pro Arg Thr Gly Ile Tyr Ala Glu Arg Lys His Asn Ala Phe Val
225                 230                 235                 240

Asn Arg Asn

<210> SEQ ID NO 10
<211> LENGTH: 283
<212> TYPE: PRT
<213> ORGANISM: artificial
<220> FEATURE:
<223> OTHER INFORMATION: LukEP184A,G186A,P187A

<400> SEQUENCE: 10

Asn Thr Asn Ile Glu Asn Ile Gly Asp Gly Ala Glu Val Ile Lys Arg
 1               5                  10                  15

Thr Glu Asp Val Ser Ser Lys Lys Trp Gly Val Thr Gln Asn Val Gln
                 20                  25                  30

Phe Asp Phe Val Lys Asp Lys Lys Tyr Asn Lys Asp Ala Leu Ile Val
             35                  40                  45

Lys Met Gln Gly Phe Ile Asn Ser Arg Thr Ser Phe Ser Asp Val Lys
 50                  55                  60

Gly Ser Gly Tyr Glu Leu Thr Lys Arg Met Ile Trp Pro Phe Gln Tyr
 65                  70                  75                  80

Asn Ile Gly Leu Thr Thr Lys Asp Pro Asn Val Ser Leu Ile Asn Tyr
                 85                  90                  95

Leu Pro Lys Asn Lys Ile Glu Thr Thr Asp Val Gly Gln Thr Leu Gly
            100                 105                 110

Tyr Asn Ile Gly Gly Asn Phe Gln Ser Ala Pro Ser Ile Gly Gly Asn
        115                 120                 125

Gly Ser Phe Asn Tyr Ser Lys Thr Ile Ser Tyr Thr Gln Lys Ser Tyr
    130                 135                 140

Val Ser Glu Val Asp Lys Gln Asn Ser Lys Ser Val Lys Trp Gly Val
145                 150                 155                 160

Lys Ala Asn Glu Phe Val Thr Pro Asp Gly Lys Lys Ser Ala His Asp
                165                 170                 175
```

```
Arg Tyr Leu Phe Val Gln Ser Ala Asn Ala Ala Thr Gly Ser Ala Arg
            180                 185                 190

Glu Tyr Phe Ala Pro Asp Asn Gln Leu Pro Pro Leu Val Gln Ser Gly
        195                 200                 205

Phe Asn Pro Ser Phe Ile Thr Thr Leu Ser His Glu Lys Gly Ser Ser
    210                 215                 220

Asp Thr Ser Glu Phe Glu Ile Ser Tyr Gly Arg Asn Leu Asp Ile Thr
225                 230                 235                 240

Tyr Ala Thr Leu Phe Pro Arg Thr Gly Ile Tyr Ala Glu Arg Lys His
            245                 250                 255

Asn Ala Phe Val Asn Arg Asn Phe Val Val Arg Tyr Glu Val Asn Trp
        260                 265                 270

Lys Thr His Glu Ile Lys Val Lys Gly His Asn
    275                 280
```

<210> SEQ ID NO 11
<211> LENGTH: 283
<212> TYPE: PRT
<213> ORGANISM: artificial
<220> FEATURE:
<223> OTHER INFORMATION: LukEP184A,G186A,P187A,G189A

<400> SEQUENCE: 11

```
Asn Thr Asn Ile Glu Asn Ile Gly Asp Gly Ala Glu Val Ile Lys Arg
1               5                   10                  15

Thr Glu Asp Val Ser Ser Lys Lys Trp Gly Val Thr Gln Asn Val Gln
            20                  25                  30

Phe Asp Phe Val Lys Asp Lys Lys Tyr Asn Lys Asp Ala Leu Ile Val
        35                  40                  45

Lys Met Gln Gly Phe Ile Asn Ser Arg Thr Ser Phe Ser Asp Val Lys
    50                  55                  60

Gly Ser Gly Tyr Glu Leu Thr Lys Arg Met Ile Trp Pro Phe Gln Tyr
65                  70                  75                  80

Asn Ile Gly Leu Thr Thr Lys Asp Pro Asn Val Ser Leu Ile Asn Tyr
            85                  90                  95

Leu Pro Lys Asn Lys Ile Glu Thr Thr Asp Val Gly Gln Thr Leu Gly
        100                 105                 110

Tyr Asn Ile Gly Gly Asn Phe Gln Ser Ala Pro Ser Ile Gly Gly Asn
    115                 120                 125

Gly Ser Phe Asn Tyr Ser Lys Thr Ile Ser Tyr Thr Gln Lys Ser Tyr
130                 135                 140

Val Ser Glu Val Asp Lys Gln Asn Ser Lys Ser Val Lys Trp Gly Val
145                 150                 155                 160

Lys Ala Asn Glu Phe Val Thr Pro Asp Gly Lys Lys Ser Ala His Asp
            165                 170                 175

Arg Tyr Leu Phe Val Gln Ser Ala Asn Ala Ala Thr Ala Ser Ala Arg
        180                 185                 190

Glu Tyr Phe Ala Pro Asp Asn Gln Leu Pro Pro Leu Val Gln Ser Gly
    195                 200                 205

Phe Asn Pro Ser Phe Ile Thr Thr Leu Ser His Glu Lys Gly Ser Ser
    210                 215                 220

Asp Thr Ser Glu Phe Glu Ile Ser Tyr Gly Arg Asn Leu Asp Ile Thr
225                 230                 235                 240

Tyr Ala Thr Leu Phe Pro Arg Thr Gly Ile Tyr Ala Glu Arg Lys His
            245                 250                 255
```

```
Asn Ala Phe Val Asn Arg Asn Phe Val Val Arg Tyr Glu Val Asn Trp
                260                 265                 270

Lys Thr His Glu Ile Lys Val Lys Gly His Asn
    275                 280
```

<210> SEQ ID NO 12
<211> LENGTH: 301
<212> TYPE: PRT
<213> ORGANISM: Staphylococcus aureus

<400> SEQUENCE: 12

```
Ala Gln His Ile Thr Pro Val Ser Glu Lys Lys Val Asp Asp Lys Ile
1               5                   10                  15

Thr Leu Tyr Lys Thr Thr Ala Thr Ser Asp Asn Asp Lys Leu Asn Ile
            20                  25                  30

Ser Gln Ile Leu Thr Phe Asn Phe Ile Lys Asp Lys Ser Tyr Asp Lys
        35                  40                  45

Asp Thr Leu Val Leu Lys Ala Ala Gly Asn Ile Asn Ser Gly Tyr Lys
    50                  55                  60

Lys Pro Asn Pro Lys Asp Tyr Asn Tyr Ser Gln Phe Tyr Trp Gly Gly
65                  70                  75                  80

Lys Tyr Asn Val Ser Val Ser Ser Glu Ser Asn Asp Ala Val Asn Val
                85                  90                  95

Val Asp Tyr Ala Pro Lys Asn Gln Asn Glu Glu Phe Gln Val Gln Gln
            100                 105                 110

Thr Leu Gly Tyr Ser Tyr Gly Gly Asp Ile Asn Ile Ser Asn Gly Leu
        115                 120                 125

Ser Gly Gly Leu Asn Gly Ser Lys Ser Phe Ser Glu Thr Ile Asn Tyr
    130                 135                 140

Lys Gln Glu Ser Tyr Arg Thr Thr Ile Asp Arg Lys Thr Asn His Lys
145                 150                 155                 160

Ser Ile Gly Trp Gly Val Glu Ala His Lys Ile Met Asn Asn Gly Trp
                165                 170                 175

Gly Pro Tyr Gly Arg Asp Ser Tyr Asp Pro Thr Tyr Gly Asn Glu Leu
            180                 185                 190

Phe Leu Gly Gly Arg Gln Ser Ser Ser Asn Ala Gly Gln Asn Phe Leu
        195                 200                 205

Pro Thr His Gln Met Pro Leu Leu Ala Arg Gly Asn Phe Asn Pro Glu
    210                 215                 220

Phe Ile Ser Val Leu Ser His Lys Gln Asn Asp Thr Lys Lys Ser Lys
225                 230                 235                 240

Ile Lys Val Thr Tyr Gln Arg Glu Met Asp Arg Tyr Thr Asn Gln Trp
                245                 250                 255

Asn Arg Leu His Trp Val Gly Asn Asn Tyr Lys Asn Gln Asn Thr Val
            260                 265                 270

Thr Phe Thr Ser Thr Tyr Glu Val Asp Trp Gln Asn His Thr Val Lys
        275                 280                 285

Leu Ile Gly Thr Asp Ser Lys Glu Thr Asn Pro Gly Val
    290                 295                 300
```

<210> SEQ ID NO 13
<211> LENGTH: 281
<212> TYPE: PRT
<213> ORGANISM: artificial
<220> FEATURE:
<223> OTHER INFORMATION: HlgALukS-DR4

<400> SEQUENCE: 13

Glu Asn Lys Ile Glu Asp Ile Gly Gln Gly Ala Glu Ile Ile Lys Arg
1               5                   10                  15

Thr Gln Asp Ile Thr Ser Lys Arg Leu Ala Ile Thr Gln Asn Ile Gln
            20                  25                  30

Phe Asp Phe Val Lys Asp Lys Lys Tyr Asn Lys Asp Ala Leu Val Val
        35                  40                  45

Lys Met Gln Gly Phe Ile Ser Ser Arg Thr Thr Tyr Ser Asp Leu Lys
    50                  55                  60

Lys Tyr Pro Tyr Ile Lys Arg Met Ile Trp Pro Phe Gln Tyr Asn Ile
65                  70                  75                  80

Ser Leu Lys Thr Lys Asp Ser Asn Val Asp Leu Ile Asn Tyr Leu Pro
                85                  90                  95

Lys Asn Lys Ile Asp Ser Ala Asp Val Ser Gln Lys Leu Gly Tyr Asn
            100                 105                 110

Ile Gly Gly Asn Phe Gln Ser Ala Pro Ser Ile Gly Gly Ser Gly Ser
        115                 120                 125

Phe Asn Tyr Ser Lys Thr Ile Ser Tyr Asn Gln Lys Asn Tyr Val Thr
    130                 135                 140

Glu Val Glu Ser Gln Asn Ser Lys Gly Val Lys Trp Gly Val Lys Ala
145                 150                 155                 160

Asn Ser Phe Val Thr Pro Asn Gly Gln Val Ser Ala Tyr Asp Gln Tyr
                165                 170                 175

Leu Phe Ala Gly Tyr Lys Pro Tyr Ser Gln Asn Pro Arg Asp Tyr Phe
            180                 185                 190

Val Pro Asp Asn Gln Leu Pro Pro Leu Ile Gln Ser Gly Phe Asn Pro
        195                 200                 205

Ser Phe Ile Thr Thr Leu Ser His Glu Arg Gly Lys Gly Asp Lys Ser
    210                 215                 220

Glu Phe Glu Ile Thr Tyr Gly Arg Asn Met Asp Ala Thr Tyr Ala Tyr
225                 230                 235                 240

Val Thr Arg His Arg Leu Ala Val Asp Arg Lys His Asp Ala Phe Lys
                245                 250                 255

Asn Arg Asn Val Thr Val Lys Tyr Glu Val Asn Trp Lys Thr His Glu
            260                 265                 270

Val Lys Ile Lys Ser Ile Thr Pro Lys
        275                 280

<210> SEQ ID NO 14
<211> LENGTH: 240
<212> TYPE: PRT
<213> ORGANISM: artificial
<220> FEATURE:
<223> OTHER INFORMATION: HlgA20-258 LukS-DR

<400> SEQUENCE: 14

Ile Thr Ser Lys Arg Leu Ala Ile Thr Gln Asn Ile Gln Phe Asp Phe
1               5                   10                  15

Val Lys Asp Lys Lys Tyr Asn Lys Asp Ala Leu Val Val Lys Met Gln
            20                  25                  30

Gly Phe Ile Ser Ser Arg Thr Thr Tyr Ser Asp Leu Lys Lys Tyr Pro
        35                  40                  45

Tyr Ile Lys Arg Met Ile Trp Pro Phe Gln Tyr Asn Ile Ser Leu Lys
    50                  55                  60

```
Thr Lys Asp Ser Asn Val Asp Leu Ile Asn Tyr Leu Pro Lys Asn Lys
 65                  70                  75                  80

Ile Asp Ser Ala Asp Val Ser Gln Lys Leu Gly Tyr Asn Ile Gly Gly
                 85                  90                  95

Asn Phe Gln Ser Ala Pro Ser Ile Gly Gly Ser Gly Ser Phe Asn Tyr
            100                 105                 110

Ser Lys Thr Ile Ser Tyr Asn Gln Lys Asn Tyr Val Thr Glu Val Glu
        115                 120                 125

Ser Gln Asn Ser Lys Gly Val Lys Trp Gly Val Lys Ala Asn Ser Phe
    130                 135                 140

Val Thr Pro Asn Gly Gln Val Ser Ala Tyr Asp Gln Tyr Leu Phe Ala
145                 150                 155                 160

Gly Tyr Lys Pro Tyr Ser Gln Asn Pro Arg Asp Tyr Phe Val Pro Asp
                165                 170                 175

Asn Gln Leu Pro Pro Leu Ile Gln Ser Gly Phe Asn Pro Ser Phe Ile
            180                 185                 190

Thr Thr Leu Ser His Glu Arg Gly Lys Gly Asp Lys Ser Glu Phe Glu
        195                 200                 205

Ile Thr Tyr Gly Arg Asn Met Asp Ala Thr Tyr Ala Tyr Val Thr Arg
    210                 215                 220

His Arg Leu Ala Val Asp Arg Lys His Asp Ala Phe Lys Asn Arg Asn
225                 230                 235                 240

<210> SEQ ID NO 15
<211> LENGTH: 280
<212> TYPE: PRT
<213> ORGANISM: artificial
<220> FEATURE:
<223> OTHER INFORMATION: HlgAP182A,G184A,P185A

<400> SEQUENCE: 15

Glu Asn Lys Ile Glu Asp Ile Gly Gln Gly Ala Glu Ile Ile Lys Arg
  1               5                  10                  15

Thr Gln Asp Ile Thr Ser Lys Arg Leu Ala Ile Thr Gln Asn Ile Gln
             20                  25                  30

Phe Asp Phe Val Lys Asp Lys Lys Tyr Asn Lys Asp Ala Leu Val Val
         35                  40                  45

Lys Met Gln Gly Phe Ile Ser Ser Arg Thr Thr Tyr Ser Asp Leu Lys
 50                  55                  60

Lys Tyr Pro Tyr Ile Lys Arg Met Ile Trp Pro Phe Gln Tyr Asn Ile
 65                  70                  75                  80

Ser Leu Lys Thr Lys Asp Ser Asn Val Asp Leu Ile Asn Tyr Leu Pro
             85                  90                  95

Lys Asn Lys Ile Asp Ser Ala Asp Val Ser Gln Lys Leu Gly Tyr Asn
            100                 105                 110

Ile Gly Gly Asn Phe Gln Ser Ala Pro Ser Ile Gly Gly Ser Gly Ser
        115                 120                 125

Phe Asn Tyr Ser Lys Thr Ile Ser Tyr Asn Gln Lys Asn Tyr Val Thr
    130                 135                 140

Glu Val Glu Ser Gln Asn Ser Lys Gly Val Lys Trp Gly Val Lys Ala
145                 150                 155                 160

Asn Ser Phe Val Thr Pro Asn Gly Gln Val Ser Ala Tyr Asp Gln Tyr
                165                 170                 175

Leu Phe Ala Gln Asp Ala Thr Ala Ala Ala Arg Asp Tyr Phe Val
            180                 185                 190
```

```
Pro Asp Asn Gln Leu Pro Pro Leu Ile Gln Ser Gly Phe Asn Pro Ser
            195                 200                 205

Phe Ile Thr Thr Leu Ser His Glu Arg Gly Lys Gly Asp Lys Ser Glu
        210                 215                 220

Phe Glu Ile Thr Tyr Gly Arg Asn Met Asp Ala Thr Tyr Ala Tyr Val
225                 230                 235                 240

Thr Arg His Arg Leu Ala Val Asp Arg Lys His Asp Ala Phe Lys Asn
                245                 250                 255

Arg Asn Val Thr Val Lys Tyr Glu Val Asn Trp Lys Thr His Glu Val
            260                 265                 270

Lys Ile Lys Ser Ile Thr Pro Lys
        275                 280

<210> SEQ ID NO 16
<211> LENGTH: 299
<212> TYPE: PRT
<213> ORGANISM: artificial
<220> FEATURE:
<223> OTHER INFORMATION: HlgB

<400> SEQUENCE: 16

Glu Gly Lys Ile Thr Pro Val Ser Val Lys Lys Val Asp Asp Lys Val
1               5                   10                  15

Thr Leu Tyr Lys Thr Thr Ala Thr Ala Asp Ser Asp Lys Phe Lys Ile
            20                  25                  30

Ser Gln Ile Leu Thr Phe Asn Phe Ile Lys Asp Lys Ser Tyr Asp Lys
        35                  40                  45

Asp Thr Leu Val Leu Lys Ala Thr Gly Asn Ile Asn Ser Gly Phe Val
    50                  55                  60

Lys Pro Asn Pro Asn Asp Tyr Asp Phe Ser Lys Leu Tyr Trp Gly Ala
65                  70                  75                  80

Lys Tyr Asn Val Ser Ile Ser Ser Gln Ser Asn Asp Ser Val Asn Val
            85                  90                  95

Val Asp Tyr Ala Pro Lys Asn Gln Asn Glu Glu Phe Gln Val Gln Asn
            100                 105                 110

Thr Leu Gly Tyr Thr Phe Gly Gly Asp Ile Ser Ile Ser Asn Gly Leu
        115                 120                 125

Ser Gly Gly Leu Asn Gly Asn Thr Ala Phe Ser Glu Thr Ile Asn Tyr
    130                 135                 140

Lys Gln Glu Ser Tyr Arg Thr Thr Leu Ser Arg Asn Thr Asn Tyr Lys
145                 150                 155                 160

Asn Val Gly Trp Gly Val Glu Ala His Lys Ile Met Asn Asn Gly Trp
            165                 170                 175

Gly Pro Tyr Gly Arg Asp Ser Phe His Pro Thr Tyr Gly Asn Glu Leu
        180                 185                 190

Phe Leu Ala Gly Arg Gln Ser Ser Ala Tyr Ala Gly Gln Asn Phe Ile
    195                 200                 205

Ala Gln His Gln Met Pro Leu Leu Ser Arg Ser Asn Phe Asn Pro Glu
    210                 215                 220

Phe Leu Ser Val Leu Ser His Arg Gln Asp Gly Ala Lys Lys Ser Lys
225                 230                 235                 240

Ile Thr Val Thr Tyr Gln Arg Glu Met Asp Leu Tyr Gln Ile Arg Trp
            245                 250                 255

Asn Gly Phe Tyr Trp Ala Gly Ala Asn Tyr Lys Asn Phe Lys Thr Arg
        260                 265                 270
```

Thr Phe Lys Ser Thr Tyr Glu Ile Asp Trp Glu Asn His Lys Val Lys
             275                 280                 285

Leu Leu Asp Thr Lys Glu Thr Glu Asn Asn Lys
        290                 295

<210> SEQ ID NO 17
<211> LENGTH: 38
<212> TYPE: DNA
<213> ORGANISM: Artificial
<220> FEATURE:
<223> OTHER INFORMATION: Primer

<400> SEQUENCE: 17
cccnctcgag aatactaata ttgaaaatat tggtgatg                              38

<210> SEQ ID NO 18
<211> LENGTH: 42
<212> TYPE: DNA
<213> ORGANISM: Artificial
<220> FEATURE:
<223> OTHER INFORMATION: Primer

<400> SEQUENCE: 18
gtaataagta gtctttgaat taataaaacc ttgcatttta ac                        42

<210> SEQ ID NO 19
<211> LENGTH: 40
<212> TYPE: DNA
<213> ORGANISM: Artificial
<220> FEATURE:
<223> OTHER INFORMATION: Primer

<400> SEQUENCE: 19
catataaaag caatgaggtg gccattccaa tataatatag                           40

<210> SEQ ID NO 20
<211> LENGTH: 54
<212> TYPE: DNA
<213> ORGANISM: Artificial
<220> FEATURE:
<223> OTHER INFORMATION: Primer

<400> SEQUENCE: 20
tcaaagacta cttattacaa ttacaaaaac acagatcata taaaagcaat gagg           54

<210> SEQ ID NO 21
<211> LENGTH: 54
<212> TYPE: DNA
<213> ORGANISM: Artificial
<220> FEATURE:
<223> OTHER INFORMATION: Primer

<400> SEQUENCE: 21
cctcattgct tttatatgat ctgtgttttt gtaattgtaa taagtagtct tga            54

<210> SEQ ID NO 22
<211> LENGTH: 41
<212> TYPE: DNA
<213> ORGANISM: Artificial
<220> FEATURE:
<223> OTHER INFORMATION: Primer

<400> SEQUENCE: 22
gttttgttga ttataactaa ttgttttaga ataattaaat g                         41

<210> SEQ ID NO 23
<211> LENGTH: 34
<212> TYPE: DNA
<213> ORGANISM: Artificial
<220> FEATURE:
<223> OTHER INFORMATION: Primer

<400> SEQUENCE: 23
gaacgtcaaa attcaaaatc tgttaaatgg ggtg                        34

<210> SEQ ID NO 24
<211> LENGTH: 48
<212> TYPE: DNA
<213> ORGANISM: Artificial
<220> FEATURE:
<223> OTHER INFORMATION: Primer

<400> SEQUENCE: 24
agttataatc aacaaaacta tatcagtgaa gtagaacgtc aaaattca         48

<210> SEQ ID NO 25
<211> LENGTH: 48
<212> TYPE: DNA
<213> ORGANISM: Artificial
<220> FEATURE:
<223> OTHER INFORMATION: Primer

<400> SEQUENCE: 25
tgaattttga cgttctactt cactgatata gttttgttga ttataact         48

<210> SEQ ID NO 26
<211> LENGTH: 35
<212> TYPE: DNA
<213> ORGANISM: Artificial
<220> FEATURE:
<223> OTHER INFORMATION: Primer

<400> SEQUENCE: 26
gtgataaatg aattagcttt aacaccccat ttaac                       35

<210> SEQ ID NO 27
<211> LENGTH: 37
<212> TYPE: DNA
<213> ORGANISM: Artificial
<220> FEATURE:
<223> OTHER INFORMATION: Primer

<400> SEQUENCE: 27
gtaaaatgtc tggacatgat ccaaatttat ttgttgg                     37

<210> SEQ ID NO 28
<211> LENGTH: 45
<212> TYPE: DNA
<213> ORGANISM: Artificial
<220> FEATURE:
<223> OTHER INFORMATION: Primer

<400> SEQUENCE: 28
gctaattcat ttatcacatc attaggtaaa atgtctggac atgat            45

<210> SEQ ID NO 29
<211> LENGTH: 45
<212> TYPE: DNA
<213> ORGANISM: Artificial
<220> FEATURE:
<223> OTHER INFORMATION: Primer

```
<400> SEQUENCE: 29
atcatgtcca gacattttac ctaatgatgt gataaatgaa ttagc                    45

<210> SEQ ID NO 30
<211> LENGTH: 44
<212> TYPE: DNA
<213> ORGANISM: Artificial
<220> FEATURE:
<223> OTHER INFORMATION: Primer

<400> SEQUENCE: 30
ctatatggtt tatatccaac aaataaatat ctatcatgcg caga                     44

<210> SEQ ID NO 31
<211> LENGTH: 44
<212> TYPE: DNA
<213> ORGANISM: Artificial
<220> FEATURE:
<223> OTHER INFORMATION: Primer

<400> SEQUENCE: 31
gactattttg ttccagacaa tcaattgcca cctttagttc aaag                     44

<210> SEQ ID NO 32
<211> LENGTH: 52
<212> TYPE: DNA
<213> ORGANISM: Artificial
<220> FEATURE:
<223> OTHER INFORMATION: Primer

<400> SEQUENCE: 32
tgttggatat aaaccatata gtcaaaatcc gagagactat tttgttccag ac            52

<210> SEQ ID NO 33
<211> LENGTH: 52
<212> TYPE: DNA
<213> ORGANISM: Artificial
<220> FEATURE:
<223> OTHER INFORMATION: Primer

<400> SEQUENCE: 33
gtctggaaca aaatagtctc tcggattttg actatatggt ttatatccaa ca            52

<210> SEQ ID NO 34
<211> LENGTH: 43
<212> TYPE: DNA
<213> ORGANISM: Artificial
<220> FEATURE:
<223> OTHER INFORMATION: Primer

<400> SEQUENCE: 34
catgagtaac atccatattt ctaccatatg aaatttcaaa ttc                      43

<210> SEQ ID NO 35
<211> LENGTH: 39
<212> TYPE: DNA
<213> ORGANISM: Artificial
<220> FEATURE:
<223> OTHER INFORMATION: Primer

<400> SEQUENCE: 35
gagactattt tgttccagat aatcaattgc cacctttag                           39
```

<210> SEQ ID NO 36
<211> LENGTH: 43
<212> TYPE: DNA
<213> ORGANISM: Artificial
<220> FEATURE:
<223> OTHER INFORMATION: Primer

<400> SEQUENCE: 36
gaatttgaaa tttcatatgg tagaaatatg gatgttactc atg         43

<210> SEQ ID NO 37
<211> LENGTH: 43
<212> TYPE: DNA
<213> ORGANISM: Artificial
<220> FEATURE:
<223> OTHER INFORMATION: Primer

<400> SEQUENCE: 37
caaagtttct atttacaaat gcattgtgta ttctagatcc ttc         43

<210> SEQ ID NO 38
<211> LENGTH: 38
<212> TYPE: DNA
<213> ORGANISM: Artificial
<220> FEATURE:
<223> OTHER INFORMATION: Primer

<400> SEQUENCE: 38
ccccggatcc ttaattatgt cctttcactt taatttcg              38

<210> SEQ ID NO 39
<211> LENGTH: 33
<212> TYPE: DNA
<213> ORGANISM: Artificial
<220> FEATURE:
<223> OTHER INFORMATION: Primer

<400> SEQUENCE: 39
ccccctgcag gataggtgag atgcatacac aac                    33

<210> SEQ ID NO 40
<211> LENGTH: 36
<212> TYPE: DNA
<213> ORGANISM: Artificial
<220> FEATURE:
<223> OTHER INFORMATION: Primer

<400> SEQUENCE: 40
ccccggatcc ttatactcca ggattagttt ctttag                 36

<210> SEQ ID NO 41
<211> LENGTH: 46
<212> TYPE: DNA
<213> ORGANISM: Artificial
<220> FEATURE:
<223> OTHER INFORMATION: Primer

<400> SEQUENCE: 41
caatattttc aatattagta tttgctctag attcttgaat cggaga      46

<210> SEQ ID NO 42
<211> LENGTH: 46
<212> TYPE: DNA
<213> ORGANISM: Artificial
<220> FEATURE:
<223> OTHER INFORMATION: Primer

<400> SEQUENCE: 42
tctccgattc aagaatctag agcaaatact aatattgaaa atattg                46

<210> SEQ ID NO 43
<211> LENGTH: 41
<212> TYPE: DNA
<213> ORGANISM: Artificial
<220> FEATURE:
<223> OTHER INFORMATION: Primer

<400> SEQUENCE: 43
actaattttt tcattttcat attaattatg tcctttcact t                     41

<210> SEQ ID NO 44
<211> LENGTH: 41
<212> TYPE: DNA
<213> ORGANISM: Artificial
<220> FEATURE:
<223> OTHER INFORMATION: Primer

<400> SEQUENCE: 44
aagtgaaagg acataattaa tatgaaaatg aaaaaattag t                     41

<210> SEQ ID NO 45
<211> LENGTH: 37
<212> TYPE: DNA
<213> ORGANISM: Artificial
<220> FEATURE:
<223> OTHER INFORMATION: Primer

<400> SEQUENCE: 45
cccggatcca atactaatat tgaaaatatt ggtgatg                          37

<210> SEQ ID NO 46
<211> LENGTH: 35
<212> TYPE: DNA
<213> ORGANISM: Artificial
<220> FEATURE:
<223> OTHER INFORMATION: Primer

<400> SEQUENCE: 46
cccctgcagt tatactccag gattagtttc tttag                            35

<210> SEQ ID NO 47
<211> LENGTH: 37
<212> TYPE: DNA
<213> ORGANISM: Artificial
<220> FEATURE:
<223> OTHER INFORMATION: Primer

<400> SEQUENCE: 47
cccggatcca atactaatat tgaaaatatt ggtgatg                          37

<210> SEQ ID NO 48
<211> LENGTH: 34
<212> TYPE: DNA
<213> ORGANISM: Artificial
<220> FEATURE:
<223> OTHER INFORMATION: Primer

<400> SEQUENCE: 48
cccggatccg aaaataagat agaagatatc ggcc                             34

```
<210> SEQ ID NO 49
<211> LENGTH: 37
<212> TYPE: DNA
<213> ORGANISM: Artificial
<220> FEATURE:
<223> OTHER INFORMATION: Primer

<400> SEQUENCE: 49
cccctgcagt taattatgtc ctttcacttt aatttcg                           37

<210> SEQ ID NO 50
<211> LENGTH: 58
<212> TYPE: DNA
<213> ORGANISM: Artificial
<220> FEATURE:
<223> OTHER INFORMATION: Primer

<400> SEQUENCE: 50
gcaaaatatt ctcttgctga tgctgttgct gcatttgcac tttgtacgaa taaatatc   58

<210> SEQ ID NO 51
<211> LENGTH: 58
<212> TYPE: DNA
<213> ORGANISM: Artificial
<220> FEATURE:
<223> OTHER INFORMATION: Primer

<400> SEQUENCE: 51
gatatttatt cgtacaaagt gcaaatgcag caacagcatc agcaagagaa tattttgc   58

<210> SEQ ID NO 52
<211> LENGTH: 39
<212> TYPE: DNA
<213> ORGANISM: Artificial
<220> FEATURE:
<223> OTHER INFORMATION: Primer

<400> SEQUENCE: 52
cccctgcagt tacttaggtg tgatgctttt aatttttac                        39

<210> SEQ ID NO 53
<211> LENGTH: 62
<212> TYPE: DNA
<213> ORGANISM: Artificial
<220> FEATURE:
<223> OTHER INFORMATION: Primer

<400> SEQUENCE: 53
ggatataaac catatagtca aaatccgaga gactattttg ttccagataa tcaactacct  60
cc                                                                 62

<210> SEQ ID NO 54
<211> LENGTH: 66
<212> TYPE: DNA
<213> ORGANISM: Artificial
<220> FEATURE:
<223> OTHER INFORMATION: Primer

<400> SEQUENCE: 54
aacaaaatag tctctcggat tttgactata tggtttatat cctgcaaata agtattgatc  60
atatgc                                                             66
```

```
<210> SEQ ID NO 55
<211> LENGTH: 65
<212> TYPE: DNA
<213> ORGANISM: Artificial
<220> FEATURE:
<223> OTHER INFORMATION: Primer

<400> SEQUENCE: 55
caaagtccaa atggtccaac aggttcagca agagaatatt ttgctccaga taatcaacta    60
cctcc                                                                65

<210> SEQ ID NO 56
<211> LENGTH: 69
<212> TYPE: DNA
<213> ORGANISM: Artificial
<220> FEATURE:
<223> OTHER INFORMATION: Primer

<400> SEQUENCE: 56
agcaaaatat tctcttgctg aacctgttgg accatttgga ctttgtgcaa ataagtattg    60
atcatatgc                                                            69

<210> SEQ ID NO 57
<211> LENGTH: 284
<212> TYPE: PRT
<213> ORGANISM: Staphylococcus aureus

<400> SEQUENCE: 57

Asp Asn Asn Ile Glu Asn Ile Gly Asp Gly Ala Glu Val Val Lys Arg
1               5                   10                  15

Thr Glu Asp Thr Ser Ser Asp Lys Trp Gly Val Thr Gln Asn Ile Gln
            20                  25                  30

Phe Asp Phe Val Lys Asp Lys Lys Tyr Asn Lys Asp Ala Leu Ile Leu
        35                  40                  45

Lys Met Gln Gly Phe Ile Asn Ser Lys Thr Thr Tyr Tyr Asn Tyr Lys
    50                  55                  60

Asn Thr Asp His Ile Lys Ala Met Arg Trp Pro Phe Gln Tyr Asn Ile
65                  70                  75                  80

Gly Leu Lys Thr Asn Asp Pro Asn Val Asp Leu Ile Asn Tyr Leu Pro
                85                  90                  95

Lys Asn Lys Ile Asp Ser Val Asn Val Ser Gln Thr Leu Gly Tyr Asn
            100                 105                 110

Ile Gly Gly Asn Phe Asn Ser Gly Pro Ser Thr Gly Gly Asn Gly Ser
        115                 120                 125

Phe Asn Tyr Ser Lys Thr Ile Ser Tyr Asn Gln Gln Asn Tyr Ile Ser
    130                 135                 140

Glu Val Glu Arg Gln Asn Ser Lys Ser Val Gln Trp Gly Ile Lys Ala
145                 150                 155                 160

Asn Ser Phe Ile Thr Ser Leu Gly Lys Met Ser Gly His Asp Pro Asn
                165                 170                 175

Leu Phe Val Gly Tyr Lys Pro Tyr Ser Gln Asn Pro Arg Asp Tyr Phe
            180                 185                 190

Val Pro Asp Asn Glu Leu Pro Pro Leu Val His Ser Gly Phe Asn Pro
        195                 200                 205

Ser Phe Ile Ala Thr Val Ser His Glu Lys Gly Ser Gly Asp Thr Ser
    210                 215                 220

Glu Phe Glu Ile Thr Tyr Gly Arg Asn Met Asp Val Thr His Ala Thr
225                 230                 235                 240
```

-continued

```
Arg Arg Thr Thr His Tyr Gly Asn Ser Tyr Leu Glu Gly Ser Arg Ile
            245                 250                 255

His Asn Ala Phe Val Asn Arg Asn Tyr Thr Val Lys Tyr Glu Val Asn
        260                 265                 270

Trp Lys Thr His Glu Ile Lys Val Lys Gly His Asn
        275                 280

<210> SEQ ID NO 58
<211> LENGTH: 287
<212> TYPE: PRT
<213> ORGANISM: Artificial Sequence
<220> FEATURE:
<223> OTHER INFORMATION: Leukocidin consensus sequence
<220> FEATURE:
<221> NAME/KEY: MISC_FEATURE
<222> LOCATION: (1)..(1)
<223> OTHER INFORMATION: Xaa at position 1 can be D or N
<220> FEATURE:
<221> NAME/KEY: MISC_FEATURE
<222> LOCATION: (2)..(2)
<223> OTHER INFORMATION: Xaa at position 2 can be N or T
<220> FEATURE:
<221> NAME/KEY: MISC_FEATURE
<222> LOCATION: (14)..(14)
<223> OTHER INFORMATION: Xaa at position 14 can be V or I
<220> FEATURE:
<221> NAME/KEY: MISC_FEATURE
<222> LOCATION: (20)..(20)
<223> OTHER INFORMATION: Xaa at position 20 can be T or V
<220> FEATURE:
<221> NAME/KEY: MISC_FEATURE
<222> LOCATION: (23)..(23)
<223> OTHER INFORMATION: Xaa at position 23 can be D or K
<220> FEATURE:
<221> NAME/KEY: MISC_FEATURE
<222> LOCATION: (31)..(31)
<223> OTHER INFORMATION: Xaa at position 31 can be I or V
<220> FEATURE:
<221> NAME/KEY: MISC_FEATURE
<222> LOCATION: (48)..(48)
<223> OTHER INFORMATION: Xaa at position 48 can be L or V
<220> FEATURE:
<221> NAME/KEY: MISC_FEATURE
<222> LOCATION: (57)..(57)
<223> OTHER INFORMATION: Xaa at position 57 can be K or R
<220> FEATURE:
<221> NAME/KEY: MISC_FEATURE
<222> LOCATION: (59)..(59)
<223> OTHER INFORMATION: Xaa at position 59 can be T or S
<220> FEATURE:
<221> NAME/KEY: MISC_FEATURE
<222> LOCATION: (60)..(60)
<223> OTHER INFORMATION: Xaa at position 60 can be Y or F
<220> FEATURE:
<221> NAME/KEY: MISC_FEATURE
<222> LOCATION: (61)..(61)
<223> OTHER INFORMATION: Xaa at position 61 can be Y or S
<220> FEATURE:
<221> NAME/KEY: MISC_FEATURE
<222> LOCATION: (62)..(62)
<223> OTHER INFORMATION: Xaa at position 62 can be N or D
<220> FEATURE:
<221> NAME/KEY: MISC_FEATURE
<222> LOCATION: (63)..(63)
<223> OTHER INFORMATION: Xaa at position 63 can be Y or V
<220> FEATURE:
<221> NAME/KEY: MISC_FEATURE
<222> LOCATION: (65)..(65)
<223> OTHER INFORMATION: Xaa at position 65 can be N or G
<220> FEATURE:
<221> NAME/KEY: MISC_FEATURE
<222> LOCATION: (66)..(66)
<223> OTHER INFORMATION: Xaa at position 66 can be T or S
```

```
<220> FEATURE:
<221> NAME/KEY: MISC_FEATURE
<222> LOCATION: (67)..(67)
<223> OTHER INFORMATION: Xaa at position 67 can be D or G
<220> FEATURE:
<221> NAME/KEY: MISC_FEATURE
<222> LOCATION: (68)..(68)
<223> OTHER INFORMATION: Xaa at position 68 can be H or Y
<220> FEATURE:
<221> NAME/KEY: MISC_FEATURE
<222> LOCATION: (69)..(69)
<223> OTHER INFORMATION: Xaa at position 69 can be E
<220> FEATURE:
<221> NAME/KEY: MISC_FEATURE
<222> LOCATION: (70)..(70)
<223> OTHER INFORMATION: Xaa at position 70 can be L
<220> FEATURE:
<221> NAME/KEY: MISC_FEATURE
<222> LOCATION: (71)..(71)
<223> OTHER INFORMATION: Xaa at position 71 can be I or T
<220> FEATURE:
<221> NAME/KEY: MISC_FEATURE
<222> LOCATION: (73)..(73)
<223> OTHER INFORMATION: Xaa at position 73 can be A or R
<220> FEATURE:
<221> NAME/KEY: MISC_FEATURE
<222> LOCATION: (75)..(75)
<223> OTHER INFORMATION: Xaa at position 75 can be R or I
<220> FEATURE:
<221> NAME/KEY: MISC_FEATURE
<222> LOCATION: (85)..(85)
<223> OTHER INFORMATION: Xaa at position 85 can be K or T
<220> FEATURE:
<221> NAME/KEY: MISC_FEATURE
<222> LOCATION: (87)..(87)
<223> OTHER INFORMATION: Xaa at position 87 can be N or K
<220> FEATURE:
<221> NAME/KEY: MISC_FEATURE
<222> LOCATION: (92)..(92)
<223> OTHER INFORMATION: Xaa at position 92 can be S or D
<220> FEATURE:
<221> NAME/KEY: MISC_FEATURE
<222> LOCATION: (103)..(103)
<223> OTHER INFORMATION: Xaa at position 103 can be D or E
<220> FEATURE:
<221> NAME/KEY: MISC_FEATURE
<222> LOCATION: (104)..(104)
<223> OTHER INFORMATION: Xaa at position 104 can be S or T
<220> FEATURE:
<221> NAME/KEY: MISC_FEATURE
<222> LOCATION: (105)..(105)
<223> OTHER INFORMATION: Xaa at position 105 can be V or T
<220> FEATURE:
<221> NAME/KEY: MISC_FEATURE
<222> LOCATION: (106)..(106)
<223> OTHER INFORMATION: Xaa at position 106 can be N or D
<220> FEATURE:
<221> NAME/KEY: MISC_FEATURE
<222> LOCATION: (108)..(108)
<223> OTHER INFORMATION: Xaa at position 108 can be S or G
<220> FEATURE:
<221> NAME/KEY: MISC_FEATURE
<222> LOCATION: (120)..(120)
<223> OTHER INFORMATION: Xaa at position 120 can be N or Q
<220> FEATURE:
<221> NAME/KEY: MISC_FEATURE
<222> LOCATION: (122)..(122)
<223> OTHER INFORMATION: Xaa at position 122 can be G or A
<220> FEATURE:
<221> NAME/KEY: MISC_FEATURE
<222> LOCATION: (125)..(125)
<223> OTHER INFORMATION: Xaa at position 125 can be T or I
<220> FEATURE:
<221> NAME/KEY: MISC_FEATURE
<222> LOCATION: (140)..(140)
<223> OTHER INFORMATION: Xaa at position 140 can be N or T
```

```
<220> FEATURE:
<221> NAME/KEY: MISC_FEATURE
<222> LOCATION: (142)..(142)
<223> OTHER INFORMATION: Xaa at position 142 can be Q or K
<220> FEATURE:
<221> NAME/KEY: MISC_FEATURE
<222> LOCATION: (143)..(143)
<223> OTHER INFORMATION: Xaa at position 143 can be N or S
<220> FEATURE:
<221> NAME/KEY: MISC_FEATURE
<222> LOCATION: (145)..(145)
<223> OTHER INFORMATION: Xaa at position 145 can be I or V
<220> FEATURE:
<221> NAME/KEY: MISC_FEATURE
<222> LOCATION: (149)..(149)
<223> OTHER INFORMATION: Xaa at position 149 can be E or D
<220> FEATURE:
<221> NAME/KEY: MISC_FEATURE
<222> LOCATION: (150)..(150)
<223> OTHER INFORMATION: Xaa at position 150 can be R or K
<220> FEATURE:
<221> NAME/KEY: MISC_FEATURE
<222> LOCATION: (157)..(157)
<223> OTHER INFORMATION: Xaa at position 157 can be Q or K
<220> FEATURE:
<221> NAME/KEY: MISC_FEATURE
<222> LOCATION: (160)..(160)
<223> OTHER INFORMATION: Xaa at position 160 can be I or V
<220> FEATURE:
<221> NAME/KEY: MISC_FEATURE
<222> LOCATION: (164)..(164)
<223> OTHER INFORMATION: Xaa at position 164 can be S or E
<220> FEATURE:
<221> NAME/KEY: MISC_FEATURE
<222> LOCATION: (166)..(166)
<223> OTHER INFORMATION: Xaa at position 166 can be I or V
<220> FEATURE:
<221> NAME/KEY: MISC_FEATURE
<222> LOCATION: (168)..(168)
<223> OTHER INFORMATION: Xaa at position 168 can be S or P
<220> FEATURE:
<221> NAME/KEY: MISC_FEATURE
<222> LOCATION: (169)..(169)
<223> OTHER INFORMATION: Xaa at position 169 can be L or D
<220> FEATURE:
<221> NAME/KEY: MISC_FEATURE
<222> LOCATION: (172)..(172)
<223> OTHER INFORMATION: Xaa at position 172 can be M or K
<220> FEATURE:
<221> NAME/KEY: MISC_FEATURE
<222> LOCATION: (174)..(174)
<223> OTHER INFORMATION: Xaa at position 174 can be G or A
<220> FEATURE:
<221> NAME/KEY: MISC_FEATURE
<222> LOCATION: (177)..(177)
<223> OTHER INFORMATION: Xaa at position 177 can be P or R
<220> FEATURE:
<221> NAME/KEY: MISC_FEATURE
<222> LOCATION: (178)..(178)
<223> OTHER INFORMATION: Xaa at position 178 can be N or Y
<220> FEATURE:
<221> NAME/KEY: MISC_FEATURE
<222> LOCATION: (182)..(182)
<223> OTHER INFORMATION: Xaa at position 182 can be Q
<220> FEATURE:
<221> NAME/KEY: MISC_FEATURE
<222> LOCATION: (183)..(183)
<223> OTHER INFORMATION: Xaa at position 183 can be G or S
<220> FEATURE:
<221> NAME/KEY: MISC_FEATURE
<222> LOCATION: (184)..(184)
<223> OTHER INFORMATION: Xaa at position 184 can be Y or P
<220> FEATURE:
<221> NAME/KEY: MISC_FEATURE
<222> LOCATION: (185)..(185)
<223> OTHER INFORMATION: Xaa at position 185 can be K or N
```

```
<220> FEATURE:
<221> NAME/KEY: MISC_FEATURE
<222> LOCATION: (186)..(186)
<223> OTHER INFORMATION: Xaa at position 186 can be P or G
<220> FEATURE:
<221> NAME/KEY: MISC_FEATURE
<222> LOCATION: (187)..(187)
<223> OTHER INFORMATION: Xaa at position 187 can be Y or P
<220> FEATURE:
<221> NAME/KEY: MISC_FEATURE
<222> LOCATION: (188)..(188)
<223> OTHER INFORMATION: Xaa at position 188 can be S or T
<220> FEATURE:
<221> NAME/KEY: MISC_FEATURE
<222> LOCATION: (189)..(189)
<223> OTHER INFORMATION: Xaa at position 189 can be Q or G
<220> FEATURE:
<221> NAME/KEY: MISC_FEATURE
<222> LOCATION: (190)..(190)
<223> OTHER INFORMATION: Xaa at position 190 can be N or S
<220> FEATURE:
<221> NAME/KEY: MISC_FEATURE
<222> LOCATION: (191)..(191)
<223> OTHER INFORMATION: Xaa at position 191 can be P or A
<220> FEATURE:
<221> NAME/KEY: MISC_FEATURE
<222> LOCATION: (193)..(193)
<223> OTHER INFORMATION: Xaa at position 193 can be D or E
<220> FEATURE:
<221> NAME/KEY: MISC_FEATURE
<222> LOCATION: (196)..(196)
<223> OTHER INFORMATION: Xaa at position 196 can be V or A
<220> FEATURE:
<221> NAME/KEY: MISC_FEATURE
<222> LOCATION: (200)..(200)
<223> OTHER INFORMATION: Xaa at position 200 can be E or Q
<220> FEATURE:
<221> NAME/KEY: MISC_FEATURE
<222> LOCATION: (206)..(206)
<223> OTHER INFORMATION: Xaa at position 206 can be Q or H
<220> FEATURE:
<221> NAME/KEY: MISC_FEATURE
<222> LOCATION: (215)..(215)
<223> OTHER INFORMATION: Xaa at position 215 can be A or T
<220> FEATURE:
<221> NAME/KEY: MISC_FEATURE
<222> LOCATION: (217)..(217)
<223> OTHER INFORMATION: Xaa at position 217 can be V or L
<220> FEATURE:
<221> NAME/KEY: MISC_FEATURE
<222> LOCATION: (224)..(224)
<223> OTHER INFORMATION: Xaa at position 224 can be G or S
<220> FEATURE:
<221> NAME/KEY: MISC_FEATURE
<222> LOCATION: (232)..(232)
<223> OTHER INFORMATION: Xaa at position 232 can be T or S
<220> FEATURE:
<221> NAME/KEY: MISC_FEATURE
<222> LOCATION: (237)..(237)
<223> OTHER INFORMATION: Xaa at position 237 can be M or L
<220> FEATURE:
<221> NAME/KEY: MISC_FEATURE
<222> LOCATION: (239)..(239)
<223> OTHER INFORMATION: Xaa at position 239 can be V or I
<220> FEATURE:
<221> NAME/KEY: MISC_FEATURE
<222> LOCATION: (241)..(241)
<223> OTHER INFORMATION: Xaa at position 241 can be H or Y
<220> FEATURE:
<221> NAME/KEY: MISC_FEATURE
<222> LOCATION: (244)..(244)
<223> OTHER INFORMATION: Xaa at position 244 can be R or L
<220> FEATURE:
<221> NAME/KEY: MISC_FEATURE
<222> LOCATION: (245)..(245)
<223> OTHER INFORMATION: Xaa at position 245 can be R
```

-continued

```
<220> FEATURE:
<221> NAME/KEY: MISC_FEATURE
<222> LOCATION: (246)..(246)
<223> OTHER INFORMATION: Xaa at position 246 can be T
<220> FEATURE:
<221> NAME/KEY: MISC_FEATURE
<222> LOCATION: (247)..(247)
<223> OTHER INFORMATION: Xaa at position 247 can be T
<220> FEATURE:
<221> NAME/KEY: MISC_FEATURE
<222> LOCATION: (248)..(248)
<223> OTHER INFORMATION: Xaa at position 248 can be H
<220> FEATURE:
<221> NAME/KEY: MISC_FEATURE
<222> LOCATION: (249)..(249)
<223> OTHER INFORMATION: Xaa at position 249 can be Y or F
<220> FEATURE:
<221> NAME/KEY: MISC_FEATURE
<222> LOCATION: (250)..(250)
<223> OTHER INFORMATION: Xaa at position 250 can be G or P
<220> FEATURE:
<221> NAME/KEY: MISC_FEATURE
<222> LOCATION: (251)..(251)
<223> OTHER INFORMATION: Xaa at position 251 can be N or R
<220> FEATURE:
<221> NAME/KEY: MISC_FEATURE
<222> LOCATION: (252)..(252)
<223> OTHER INFORMATION: Xaa at position 252 can be S or T
<220> FEATURE:
<221> NAME/KEY: MISC_FEATURE
<222> LOCATION: (253)..(253)
<223> OTHER INFORMATION: Xaa at position 253 can be Y or G
<220> FEATURE:
<221> NAME/KEY: MISC_FEATURE
<222> LOCATION: (254)..(254)
<223> OTHER INFORMATION: Xaa at position 254 can be L or I
<220> FEATURE:
<221> NAME/KEY: MISC_FEATURE
<222> LOCATION: (255)..(255)
<223> OTHER INFORMATION: Xaa at position 255 can be E or Y
<220> FEATURE:
<221> NAME/KEY: MISC_FEATURE
<222> LOCATION: (256)..(256)
<223> OTHER INFORMATION: Xaa at position 256 can be G or A
<220> FEATURE:
<221> NAME/KEY: MISC_FEATURE
<222> LOCATION: (257)..(257)
<223> OTHER INFORMATION: Xaa at position 257 can be S or E
<220> FEATURE:
<221> NAME/KEY: MISC_FEATURE
<222> LOCATION: (259)..(259)
<223> OTHER INFORMATION: Xaa at position 259 can be I or K
<220> FEATURE:
<221> NAME/KEY: MISC_FEATURE
<222> LOCATION: (268)..(268)
<223> OTHER INFORMATION: Xaa at position 268 can be Y or F
<220> FEATURE:
<221> NAME/KEY: MISC_FEATURE
<222> LOCATION: (269)..(269)
<223> OTHER INFORMATION: Xaa at position 269 can be T or V
<220> FEATURE:
<221> NAME/KEY: MISC_FEATURE
<222> LOCATION: (271)..(271)
<223> OTHER INFORMATION: Xaa at position 271 can be K or R

<400> SEQUENCE: 58

Xaa Xaa Asn Ile Glu Asn Ile Gly Asp Gly Ala Glu Val Xaa Lys Arg
1               5                   10                  15

Thr Glu Asp Xaa Ser Ser Xaa Lys Trp Gly Val Thr Gln Asn Xaa Gln
            20                  25                  30

Phe Asp Phe Val Lys Asp Lys Lys Tyr Asn Lys Asp Ala Leu Ile Xaa
        35                  40                  45

Lys Met Gln Gly Phe Ile Asn Ser Xaa Thr Xaa Xaa Xaa Xaa Xaa Lys
50                  55                  60
```

```
Xaa Xaa Xaa Xaa Xaa Xaa Xaa Lys Xaa Met Xaa Trp Pro Phe Gln Tyr
 65              70              75                  80

Asn Ile Gly Leu Xaa Thr Xaa Asp Pro Asn Val Xaa Leu Ile Asn Tyr
                 85              90                  95

Leu Pro Lys Asn Lys Ile Xaa Xaa Xaa Xaa Val Xaa Gln Thr Leu Gly
            100             105             110

Tyr Asn Ile Gly Gly Asn Phe Xaa Ser Xaa Pro Ser Xaa Gly Gly Asn
            115             120             125

Gly Ser Phe Asn Tyr Ser Lys Thr Ile Ser Tyr Xaa Gln Xaa Xaa Tyr
        130             135             140

Xaa Ser Glu Val Xaa Xaa Gln Asn Ser Lys Ser Val Xaa Trp Gly Xaa
145             150             155                         160

Lys Ala Asn Xaa Phe Xaa Thr Xaa Xaa Gly Lys Xaa Ser Xaa His Asp
                165             170             175

Xaa Xaa Leu Phe Val Xaa Xaa Xaa Xaa Xaa Xaa Xaa Xaa Xaa Xaa Arg
            180             185             190

Xaa Tyr Phe Xaa Pro Asp Asn Xaa Leu Pro Pro Leu Val Xaa Ser Gly
        195             200             205

Phe Asn Pro Ser Phe Ile Xaa Thr Xaa Ser His Glu Lys Gly Ser Xaa
        210             215             220

Asp Thr Ser Glu Phe Glu Ile Xaa Tyr Gly Arg Asn Xaa Asp Xaa Thr
225             230             235             240

Xaa Ala Thr Xaa Xaa Xaa Xaa Xaa Xaa Xaa Xaa Xaa Xaa Xaa Xaa Xaa
                245             250             255

Xaa Arg Xaa His Asn Ala Phe Val Asn Arg Asn Xaa Xaa Val Xaa Tyr
        260             265             270

Glu Val Asn Trp Lys Thr His Glu Ile Lys Val Lys Gly His Asn
        275             280             285
```